United States Patent
Boger

(10) Patent No.: US 8,372,823 B2
(45) Date of Patent: Feb. 12, 2013

(54) TETRACYCLIC INHIBITORS OF FATTY ACID AMIDE HYDROLASE

(75) Inventor: Dale L. Boger, La Jolla, CA (US)

(73) Assignee: The Scripps Research Institute, La Jolla, CA (US)

(*) Notice: Subject to any disclaimer, the term of this patent is extended or adjusted under 35 U.S.C. 154(b) by 286 days.

(21) Appl. No.: 12/600,728

(22) PCT Filed: May 23, 2008

(86) PCT No.: PCT/US2008/006672
§ 371 (c)(1),
(2), (4) Date: May 19, 2010

(87) PCT Pub. No.: WO2008/147553
PCT Pub. Date: Dec. 4, 2008

(65) Prior Publication Data
US 2010/0249078 A1    Sep. 30, 2010

Related U.S. Application Data

(60) Provisional application No. 60/931,747, filed on May 25, 2007.

(51) Int. Cl.
*A01N 43/00* (2006.01)
*A01N 43/42* (2006.01)
*C07D 413/00* (2006.01)
*C07D 491/02* (2006.01)
*C07D 498/02* (2006.01)
*C07D 279/10* (2006.01)
*A61K 31/44* (2006.01)
*A61K 31/535* (2006.01)
*A61K 31/54* (2006.01)

(52) U.S. Cl. .......... 514/161; 514/227.8; 514/236.8; 514/302; 544/58.6; 546/115; 546/271.4

(58) Field of Classification Search .............. None
See application file for complete search history.

(56) References Cited

U.S. PATENT DOCUMENTS

| | | | |
|---|---|---|---|
| 6,462,054 B1 * | 10/2002 | Boger | 514/302 |
| 2003/0236293 A1 * | 12/2003 | Seibert | 514/406 |
| 2006/0111359 A1 | 5/2006 | Boger | |
| 2006/0167075 A1 | 7/2006 | Pearson et al. | |

FOREIGN PATENT DOCUMENTS

| | | | |
|---|---|---|---|
| WO | WO 00/34254 | * | 6/2000 |
| WO | WO-2004/033422 A2 | | 4/2004 |
| WO | WO-2008/147553 A1 | | 12/2008 |

OTHER PUBLICATIONS

"European Application Serial No. 08754724.6, Response filed Dec. 6, 2011 to Communication and European Search Report mailed Jun. 15, 2011", 75 pgs.

"European Application Serial No. 08754724.6, Supplemental European Search Report mailed Jun. 15, 2011", 5 pgs.

Boger, D. L., et al., "Discovery of a Potent, Selective, and Efficacious Class of Reversible α-Ketoheterocycle Inhibitors of Fatty Acid Amide Hydrolase Effective as Analgesics", *J. Med. Chem.*, 48(6), 1849-1856.

"International Application Serial No. PCT/US2008/006672, International Search Report and Written Opinion mailed Sep. 4, 2008," 13 pgs.

* cited by examiner

*Primary Examiner* — Brandon Fetterolf
*Assistant Examiner* — Anna Pagonakis
(74) *Attorney, Agent, or Firm* — Schwegman Lundberg, & Woessner, P.A.

(57) ABSTRACT

Certain tetracyclic compounds are described, which may be used in pharmaceutical compositions and methods for treating disease states, disorders, and conditions mediated by fatty acid amide hydrolase (FAAH) activity. Thus, the compounds may be administered to treat, e.g., anxiety, pain, inflammation, sleep disorders, eating disorders, or movement disorders (such as multiple sclerosis).

17 Claims, No Drawings

TETRACYCLIC INHIBITORS OF FATTY ACID AMIDE HYDROLASE

PRIORITY CLAIM TO RELATED APPLICATIONS

This application is a national stage application under 35 U.S.C. §371 of PCT/US2008/006672, filed May 23, 2008, and published as WO 2008/147553 A1 on Dec. 4, 2008, which claims priority to U.S. Application Ser. No. 60/931,747, filed May 25, 2007, which applications and publication are incorporated herein by reference and made a part hereof in their entirety, and the benefit of priority is claimed thereto.

STATEMENT OF GOVERNMENT SUPPORT

A portion of the work described herein was supported by grant number DA 15648 from the National Institutes of Health. The United States Government has certain rights in this invention.

This invention was made with government support on under Contract No. DA015648 awarded by the National Institutes of Health. The Government has certain rights in this invention.

FIELD OF THE INVENTION

The present invention relates to certain tetracyclic compounds, pharmaceutical compositions containing them, and methods of using them for the treatment of disease states, disorders, and conditions mediated by fatty acid amide hydrolase (FAAH) activity.

BACKGROUND OF THE INVENTION

Medicinal benefits have been attributed to the *cannabis* plant for centuries. The primary bioactive constituent of *cannabis* is $\Delta^9$-tetrahydro-cannabinol (THC). The discovery of THC eventually led to the identification of two endogenous cannabinoid receptors responsible for its pharmacological actions, namely $CB_1$ and $CB_2$ (Goya, *Exp. Opin. Ther. Patents* 2000, 10, 1529). These discoveries not only established the site of action of THC, but also inspired inquiries into the endogenous agonists of these receptors, or "endocannabinoids". The first endocannabinoid identified was the fatty acid amide anandamide (AEA). AEA itself elicits many of the pharmacological effects of exogenous cannabinoids (Piomelli, *Nat. Rev. Neurosci.* 2003, 4(11), 873).

The catabolism of AEA is primarily attributable to the integral membrane bound protein fatty acid amide hydrolase (FAAH), which hydrolyzes AEA to arachidonic acid. FAAH was characterized in 1996 by Cravatt and co-workers (Cravatt, *Nature* 1996, 384, 83). It was subsequently determined that FAAH is additionally responsible for the catabolism of a large number of important lipid signaling fatty acid amides including: another major endocannabinoid, 2-arachidonoylglycerol (2-AG) (*Science* 1992, 258, 1946-1949); the sleep-inducing substance, oleamide (OEA) (*Science* 1995, 268, 1506); the appetite-suppressing agent, N-oleoylethanolamine (Rodriguez de Fonesca, *Nature* 2001, 414, 209); and the anti-inflammatory agent, palmitoylethanolamide (PEA) (Lambert, *Curr. Med. Chem.* 2002, 9(6), 663).

Small-molecule inhibitors of FAAH should elevate the concentrations of these endogenous signaling lipids and thereby produce their associated beneficial pharmacological effects. There have been some reports of the effects of various FAAH inhibitors in pre-clinical models.

In particular, two carbamate-based inhibitors of FAAH were reported to have analgesic properties in animal models. In rats, BMS-1 (see WO 02/087569), which has the structure shown below, was reported to have an analgesic effect in the Chung spinal nerve ligation model of neuropathic pain, and the Hargraves test of acute thermal nociception. URB-597 was reported to have efficacy in the zero plus maze model of anxiety in rats, as well as analgesic efficacy in the rat hot plate and formalin tests (Kathuria, *Nat. Med.* 2003, 9(1), 76). The sulfonylfluoride AM374 was also shown to significantly reduce spasticity in chronic relapsing experimental autoimmune encephalomyelitis (CREAE) mice, an animal model of multiple sclerosis (Baker, *FASEB J* 2001, 15(2), 300).

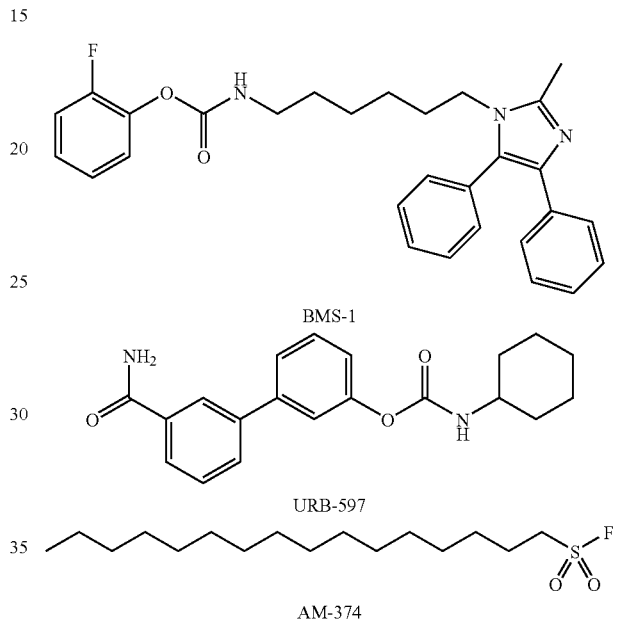

BMS-1

URB-597

AM-374

In addition, the oxazolopyridine ketone OL-135 is reported to be a potent inhibitor of FAAH, and has been reported to have analgesic activity in both the hot plate and tail emersion tests of thermal nociception in rats (WO 04/033652).

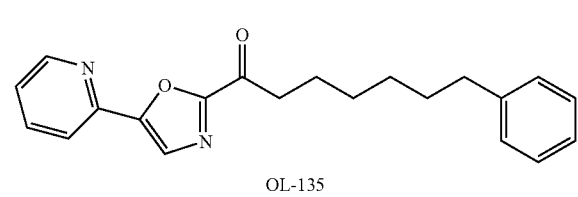 [SMILES: O=C(CCCCCCc1ccccc1)c1ncc(-c2ccccn2)o1]

OL-135

Results of research on the effects of certain exogenous cannabinoids has elucidated that a FAAH inhibitor may be useful for treating various conditions, diseases, disorders, or symptoms. These include pain, nausea/emesis, anorexia, spasticity, movement disorders, epilepsy and glaucoma. To date, approved therapeutic uses for cannabinoids include the relief of chemotherapy-induced nausea and emesis among patients with cancer and appetite enhancement in patients with HIV/AIDS who experience anorexia as a result of wasting syndrome. Two products are commercially available in some countries for these indications, namely, dronabinol (Marinol®) and nabilone.

Apart from the approved indications, a therapeutic field that has received much attention for cannabinoid use is analgesia, i.e., the treatment of pain. Five small randomized controlled trials showed that THC is superior to placebo, producing dose-related analgesia (Robson, *Br. J. Psychiatry* 2001, 178, 107-115). Atlantic Pharmaceuticals is reported to be developing a synthetic cannabinoid, CT-3, a 1,1-dimethyl heptyl derivative of the carboxylic metabolite of tetrahydrocannabinol, as an orally active analgesic and anti-inflammatory agent. A pilot phase II trial in chronic neuropathic pain with CT-3 was reported to have been initiated in Germany in May 2002.

A number of individuals with multiple sclerosis have claimed a benefit from *cannabis* for both disease-related pain and spasticity, with support from small controlled trials (Svendsen, *Br. Med. J.* 2004, 329, 253). Likewise, various victims of spinal cord injuries, such as paraplegia, have reported that their painful spasms are alleviated after smoking marijuana. A report showing that cannabinoids appear to control spasticity and tremor in the CREAE model of multiple sclerosis demonstrated that these effects are mediated by $CB_1$ and $CB_2$ receptors (Baker, *Nature* 2000, 404, 84-87). Phase 3 clinical trials have been undertaken in multiple sclerosis and spinal cord injury patients with a narrow ratio mixture of tetrahydrocannabinol/cannabidiol (THC/CBD).

Reports of small-scale controlled trials have been conducted to investigate other potential commercial uses of cannabinoids have been made. Trials in volunteers have been reported to have confirmed that oral, injected and smoked cannabinoids produced dose-related reductions in intraocular pressure (IOP) and therefore may relieve glaucoma symptoms. Ophthalmologists have prescribed *cannabis* for patients with glaucoma in whom other drugs have failed to adequately control intraocular pressure (Robson, 2001).

Inhibition of FAAH using a small-molecule inhibitor may be advantageous compared to treatment with a direct-acting $CB_1$ agonist. Administration of exogenous $CB_1$ agonists may produce a range of responses, including reduced nociception, catalepsy, hypothermia, and increased feeding behavior. These four in particular are termed the "cannabinoid tetrad." Experiments with FAAH –/– mice show reduced responses in tests of nociception, but did not show catalepsy, hypothermia, or increased feeding behavior (Cravatt, *Proc. Natl. Acad. Sci. USA* 2001, 98(16), 9371). Fasting caused levels of AEA to increase in rat limbic forebrain, but not in other brain areas, providing evidence that stimulation of AEA biosynthesis may be anatomically regionalized to targeted CNS pathways (Kirkham, *Br. J. Pharmacol.* 2002, 136, 550). The finding that AEA increases are localized within the brain, rather than systemic, suggests that FAAH inhibition with a small molecule could enhance the actions of AEA and other fatty acid amides in tissue regions where synthesis and release of these signaling molecules is occurring in a given pathophysiological condition (Piomelli, 2003).

In addition to the effects of a FAAH inhibitor on AEA and other endocannabinoids, inhibitors of FAAH's catabolism of other lipid mediators may be used in treating other therapeutic indications. For example, PEA has demonstrated biological effects in animal models of inflammation (Holt, et al. *Br. J. Pharmacol.* 2005, 146, 467-476), immunosuppression, analgesia, and neuroprotection (Ueda, *J. Biol. Chem.* 2001, 276(38), 35552). Oleamide, another substrate of FAAH, induces sleep (Boger, *Proc. Natl. Acad. Sci. USA* 2000, 97(10), 5044; Mendelson, *Neuropsychopharmacology* 2001, 25, S36). Inhibition of FAAH has also been implicated in cognition (Varvel, et al. *J. Pharmacol. Exp. Ther.* 2006, 317 (1), 251-257) and depression (Gobbi, et al. *Proc. Natl. Acad. Sci. USA* 2005, 102(51), 18620-18625).

Thus, there is evidence that small-molecule FAAH inhibitors may be useful in treating pain of various etiologies, anxiety, multiple sclerosis and other movement disorders, nausea/emesis, eating disorders, epilepsy, glaucoma, inflammation, immunosuppression, neuroprotection, depression, cognition enhancement, and sleep disorders, and potentially with fewer side effects than treatment with an exogenous cannabinoid.

Various small-molecule FAAH modulators have been described, e.g., in U.S. Patent Application Publication No. US 2006/0100212, U.S. patent application Ser. No. 11/708,788 (filed Feb. 20, 2007), and U.S. Provisional Patent Application No. 60/843,277 (filed Sep. 8, 2006). However, there remains a desire for potent FAAH modulators with suitable pharmaceutical properties.

SUMMARY OF THE INVENTION

Certain tetracyclic ketone compounds have now been found to have FAAH-modulating activity. Thus, the invention is directed to the general and preferred embodiments defined, respectively, by the independent and dependent claims appended hereto, which are incorporated by reference herein.

In one general aspect, the invention comprises a compound of Formula (I):

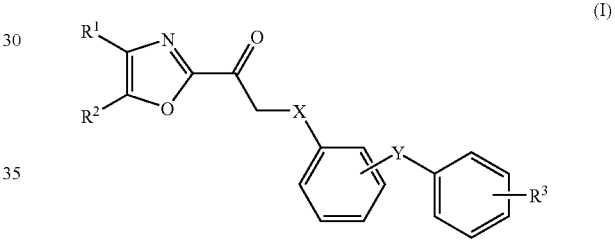

(I)

wherein
$R^1$ is H;
$R^2$ is pyridyl optionally substituted with $R^x$;
or $R^1$ and $R^2$ taken together with the oxazole to which they are attached form oxazolo[4,5-b]pyridin-2-yl;
  where $R^x$ is —$C_{1-6}$alkyl; —$C_{3-6}$cycloalkyl; —$CF_3$; —CN;
  —$C(O)C_{1-4}$alkyl optionally substituted with one, two, or three fluoro substituents; —$CO_2C_{1-4}$alkyl; —$CO_2H$;
  —$C(O)N(R^a)R^b$; —OH; —$OC_{1-6}$alkyl; halo; —$NO_2$;
  —$NR^aR^b$; —$N(R^a)C(O)R^b$; —$N(R^a)SO_2R^b$; —$SO_2N(R^a)R^b$; —$S(O)_{0-2}R^f$; or tetrazolyl;
    where $R^a$ and $R^b$ are each independently —H, —$C_{1-6}$alkyl, or —$C_{3-6}$cycloalkyl; and
    $R^f$ is —$C_{1-4}$alkyl optionally substituted with one, two, or three fluoro substituents;
$R^3$ is —H; —$C_{1-6}$alkyl; $C_{3-6}$cycloalkyl; —$CF_3$; —CN;
  —$C(O)C_{1-4}$alkyl optionally substituted with one, two, or three fluoro substituents; —$CO_2C_{1-4}$alkyl; —$CO_2H$;
  —$C(O)N(R^c)R^d$; —OH; —$OC_{1-6}$alkyl; -halo; —$NO_2$;
  —$NR^cR^d$; —$N(R^c)C(O)R^d$; —$N(R^c)SO_2R^d$; —$SO_2N(R^c)R^d$; —$S(O)_{0-2}R^f$; or —$CH_2N(R^g)R^h$;
    where $R^c$ and $R^d$ are each independently —H, —$C_{1-6}$alkyl, or —$C_{3-6}$cycloalkyl; $R^f$ is —$C_{1-4}$alkyl optionally substituted with one, two, or three fluoro substituents; and
    $R^g$ and $R^h$ are each independently H or $C_{1-4}$alkyl; or $R^g$ and $R^h$ taken together with the nitrogen to which they are attached form a monocyclic saturated heterocycloalkyl group;

X is —CH$_2$—, —O—, —S—, —S(O)—, —S(O)$_2$—, —N(R$^i$)—, or —CH(OH)—; and

Y is absent or is —CH$_2$—, —O—, —S—, —S(O)—, —S(O)$_2$—, —NR$^i$—, —CH$_2$O—, or —OCH$_2$—;

wherein R$^i$ is —H or —C$_{1-6}$alkyl;

as well as a pharmaceutically acceptable salt of a compound of Formula (I), a pharmaceutically acceptable prodrug of a compound of Formula (I), or a pharmaceutically active metabolite of Formula (I) or any combination thereof. When Y is absent, a single bond is present between the two phenyl rings of Formula I such that they form an ortho, meta or para biphenyl group. The absence of Y does not mean that the phenyl ring with the R$^3$ substitutent is also absent.

In certain preferred embodiments, the compound of Formula (I) is a compound described or exemplified in the detailed description below.

In a further general aspect, the invention relates to a pharmaceutical composition comprising: (a) an effective amount of at least one compound of Formula (I), a pharmaceutically acceptable salt of a compound of Formula (I), a pharmaceutically acceptable prodrug of a compound of Formula (I), or a pharmaceutically active metabolite of Formula (I), or any combination thereof; and (b) a pharmaceutically acceptable excipient.

In another general aspect, the invention is directed to a method of treating a subject suffering from or diagnosed with a disease, disorder, or medical condition mediated by FAAH activity, comprising administering to the subject in need of such treatment an effective amount of at least one compound of Formula (I), a pharmaceutically acceptable salt of a compound of Formula (I), a pharmaceutically acceptable prodrug of a compound of Formula (I), or a pharmaceutically active metabolite of a compound of Formula (I) or any combination thereof.

In certain preferred embodiments of the inventive method, the disease, disorder, or medical condition is selected from: anxiety, depression, pain, sleep disorders, eating disorders, inflammation, multiple sclerosis and other movement disorders, HIV wasting syndrome, closed head injury, stroke, learning and memory disorders, Alzheimer's disease, epilepsy, Tourette's syndrome, Niemann-Pick disease, Parkinson's disease, Huntington's chorea, optic neuritis, autoimmune uveitis, symptoms of drug withdrawal, nausea, emesis, sexual dysfunction, post-traumatic stress disorder, cerebral vasospasm, glaucoma, irritable bowel syndrome, inflammatory bowel disease, immunosuppression, gastroesophageal reflux disease, paralytic ileus, secretory diarrhea, gastric ulcer, rheumatoid arthritis, unwanted pregnancy, hypertension, cancer, hepatitis, allergic airway disease, auto-immune diabetes, intractable pruritis, and neuroinflammation.

Additional embodiments, features, and advantages of the invention will be apparent from the following detailed description and through practice of the invention.

DETAILED DESCRIPTION OF INVENTION AND EMBODIMENTS

The invention may be more fully appreciated by reference to the following description, including the following glossary of terms and the concluding examples. For the sake of brevity, the disclosures of the publications, including patents, cited in this specification are herein incorporated by reference. Reference is herein made to the subject matter recited by certain claims, examples of which are illustrated in the accompanying structures and formulas. While the exemplary subject matter will be described, it will be understood that the exemplary descriptions are not intended to limit the claims. On the contrary, the inventive subject matter is intended to cover all alternatives, modifications, and equivalents, which may be included within the scope of the presently disclosed subject matter as defined by the claims.

References in the specification to "one embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is within the knowledge of one skilled in the art to affect such feature, structure, or characteristic in connection with other embodiments whether or not explicitly described.

Unless otherwise indicated, the words and phrases presented in this document have their ordinary meanings to one of skill in the art. Such ordinary meanings can be obtained by reference to their use in the art and by reference to general and scientific dictionaries, for example, *Webster's New World Dictionary*, Simon & Schuster, New York, N.Y., 1995, *The American Heritage Dictionary of the English Language*, Houghton Mifflin, Boston Mass., 1981, and *Hawley's Condensed Chemical Dictionary*, 14$^{th}$ edition, Wiley Europe, 2002.

The following explanations of certain terms are meant to be illustrative rather than exhaustive. These terms have their ordinary meanings given by usage in the art and in addition include the following explanations.

As used herein, the term "about" refers to a variation of 10 percent of the value specified; for example about 50 percent carries a variation from 45 to 55 percent.

As used herein, the term "and/or" refers to any one of the items, any combination of the items, or all of the items with which this term is associated.

As used herein, the singular article of speech forms "a," "an," and "the" include plural reference such as but not limited to multiples of the element, term, feature, compound, composition, method and the like to which the article of speech refers unless the context clearly dictates otherwise.

As to any of the groups described herein, which contain one or more substituents, it is understood, of course, that such groups do not contain any substitution or substitution patterns which are sterically impractical and/or synthetically non-feasible.

The terms "comprising," "including," "having," "composed of," are open-ended terms as used herein.

The term "alkyl" refers to a straight- or branched-chain alkyl group having from 1 to 12 carbon atoms in the chain. Examples of alkyl groups include methyl (Me, which also may be structurally depicted by a/symbol), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkenyl" refers to a straight- or branched-chain alkenyl group having from 2 to 12 carbon atoms in the chain. (The double bond of the alkenyl group is formed by two sp$^2$ hybridized carbon atoms.) Illustrative alkenyl groups include prop-2-enyl, but-2-enyl, but-3-enyl, 2-methylprop-2-enyl, hex-2-enyl, and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

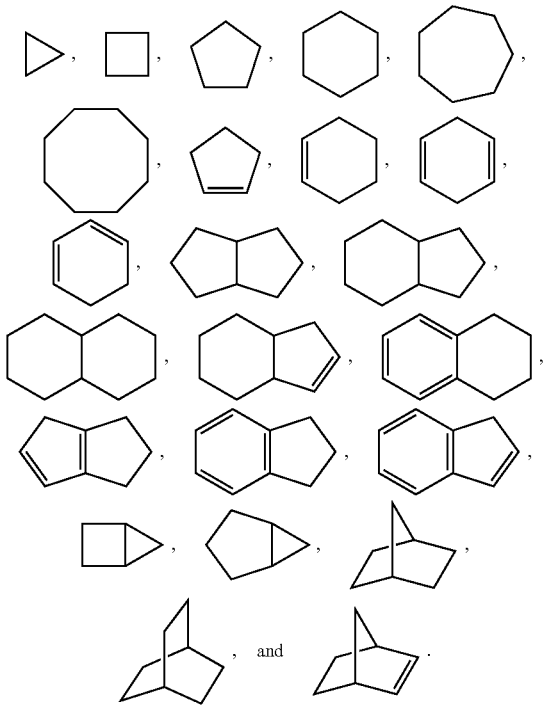

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative examples of heterocycloalkyl groups include the following entities, in the form of properly bonded moieties:

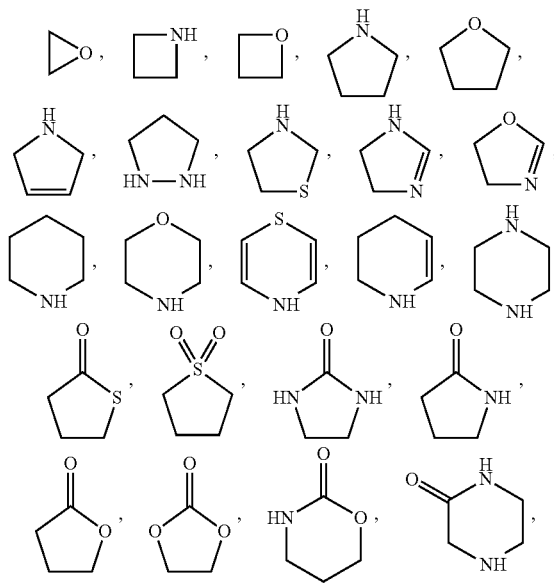

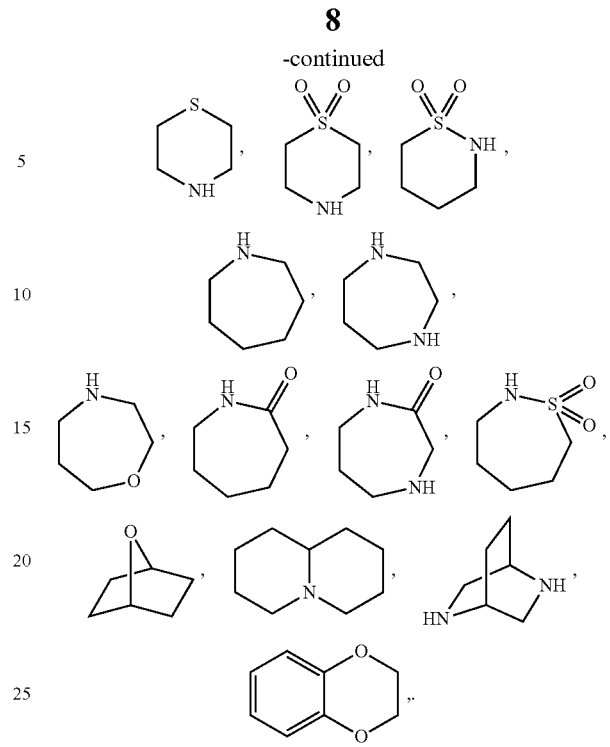

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

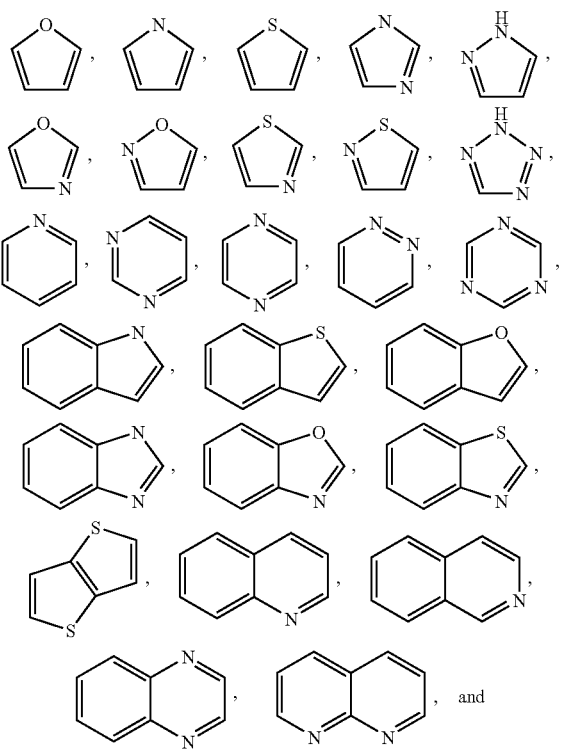

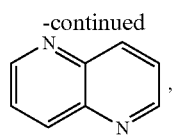

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively. Such isotopically labeled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula.

In preferred embodiments of Formula (I), $R^2$ is unsubstituted 2-pyridyl. In other preferred embodiments, $R^2$ is 2-pyridyl substituted with —CN, —CO$_2$Me, —CO$_2$Et, —CO$_2$H, or —CONH$_2$.

In preferred embodiments, $R^3$ is —H. In other preferred embodiments, $R^3$ is —CH$_2$N(R$^g$)R$^h$.

In preferred embodiments, $R^g$ and $R^h$ are both methyl. In other preferred embodiments, $R^g$ and $R^h$ are taken together with the nitrogen to which they are attached to form piperidine, morpholine, thiomorpholine, pyrrolidine, or N-methylpiperazine.

In preferred embodiments, X is —CH$_2$— or —O—. In other preferred embodiments, X is —O—. In other preferred embodiments, X is —CH$_2$—.

In preferred embodiments, Y is absent (so as to provide a biphenyl ring) or is —CH$_2$—, —O—, —S—, —NH—, or —CH$_2$O—.

The invention includes also pharmaceutically acceptable salts of the compounds represented by Formula (I), preferably of those described above and of the specific compounds exemplified herein, and methods of treatment using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to a pharmaceutically acceptable prodrug of a compound of Formula (I), and treatment methods employing such a pharmaceutically acceptable prodrug. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of a prodrug include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of a prodrug may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

The present invention also relates to a pharmaceutically active metabolite of a compound of Formula (I), and use(s) of such a metabolite in the methods of the invention. A "pharmaceutically active metabolite" means a pharmacologically active product of metabolism in the body of a compound of Formula (I) or salt thereof. A prodrug or an active metabolite of a compound may be determined using routine techniques known or available in the art. See, e.g., Bertolini, et al., *J. Med. Chem.* 1997, 40, 2011-2016; Shan, et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

A compound of Formula (I) and its pharmaceutically acceptable salt, its pharmaceutically acceptable prodrug, and its pharmaceutically active metabolite (collectively, "active agents") of the present invention are useful as FAAH inhibitors in the methods of the invention. The active agents may be used in the inventive methods for the treatment or prevention of medical conditions, diseases, or disorders mediated through inhibition or modulation of FAAH, such as those described herein. Active agents according to the invention may therefore be used as an analgesic, anti-depressant, cognition enhancer, neuroprotectant, sedative, appetite stimulant, or contraceptive.

As used herein, the term "therapeutically effective amount" and the term "effective amount" are intended to include an amount of a compound described herein, or an amount of the combination of compounds described herein, e.g., to treat or prevent the disease or disorder, or to treat the symptoms of the disease or disorder, in a host.

As used herein, the terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition.

Exemplary medical conditions, diseases, and disorders include anxiety, depression, pain, sleep disorders, eating disorders, inflammation, multiple sclerosis and other movement disorders, HIV wasting syndrome, closed head injury, stroke, learning and memory disorders, Alzheimer's disease, epilepsy, Tourette's syndrome, epilepsy, Niemann-Pick disease, Parkinson's disease, Huntington's chorea, optic neuritis, autoimmune uveitis, symptoms of drug withdrawal, nausea, emesis, sexual dysfunction, post-traumatic stress disorder, or cerebral vasospasm.

Thus, the active agents may be used to treat subjects (patients) diagnosed with or suffering from a disease, disorder, or condition mediated through FAAH activity. The term "treat" or "treating" as used herein is intended to refer to administration of an agent or composition of the invention to a subject for the purpose of effecting a therapeutic or prophylactic benefit through modulation of FAAH activity. Treating includes reversing, ameliorating, alleviating, inhibiting the progress of, lessening the severity of, or preventing a disease, disorder, or condition, or one or more symptoms of such disease, disorder or condition mediated through modulation of FAAH activity. The term "subject" refers to a mammalian patient in need of such treatment, such as a human. "Modulators" include both inhibitors and activators, where "inhibitors" refer to compounds that decrease, prevent, inactivate, desensitize or down-regulate FAAH expression or activity, and "activators" are compounds that increase, activate, facilitate, sensitize, or up-regulate FAAH expression or activity.

Accordingly, the invention relates to methods of using the active agents described herein to treat subjects diagnosed with or suffering from a disease, disorder, or condition mediated through FAAH activity, such as: anxiety, pain, sleep disorders, eating disorders, inflammation, or movement disorders (e.g., multiple sclerosis).

Symptoms or disease states are intended to be included within the scope of "medical conditions, disorders, or diseases." For example, pain may be associated with various diseases, disorders, or conditions, and may include various etiologies. Illustrative types of pain treatable with a FAAH-modulating agent according to the invention include cancer pain, postoperative pain, GI tract pain, spinal cord injury pain, visceral hyperalgesia, thalamic pain, headache (including stress headache and migraine), low back pain, neck pain, musculoskeletal pain, peripheral neuropathic pain, central neuropathic pain, neurogenerative disorder related pain, and menstrual pain. HIV wasting syndrome includes associated symptoms such as appetite loss and nausea. Parkinson's disease includes, for example, levodopa-induced dyskinesia. Treatment of multiple sclerosis may include treatment of symptoms such as spasticity, neurogenic pain, central pain, or bladder dysfunction. Symptoms of drug withdrawal may be caused by, for example, addiction to opiates or nicotine. Nausea or emesis may be due to chemotherapy, postoperative, or opioid related causes. Treatment of sexual dysfunction may include improving libido or delaying ejaculation. Treatment of cancer may include treatment of glioma. Sleep disorders include, for example, sleep apnea, insomnia, and disorders calling for treatment with an agent having a sedative or narcotic-type effect. Eating disorders include, for example, anorexia or appetite loss associated with a disease such as cancer or HIV infection/AIDS.

In treatment methods according to the invention, an effective amount of at least one active agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.001 to about 200 mg of active agent per kg of subject's body weight per day, preferably about 0.05 to 100 mg/kg/day, or about 1 to 35 mg/kg/day, or about 0.1 to 10 mg/kg daily in single or divided dosage units (e.g., BID, TID, QID). For a 70-kg human, an illustrative range for a suitable dosage amount is from about 0.05 to about 7 g/day, or about 0.2 to about 2.5 g/day. Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of Formula (I) or included with such an agent in a pharmaceutical composition according to the invention. In an exemplary embodiment, additional active ingredients are those that are known or discovered to be effective in the treatment of conditions, disorders, or diseases mediated by FAAH activity, such as another FAAH modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention. In one illustrative embodiment, a composition according to the invention may contain one or more additional active ingredients selected from opioids, NSAIDs (e.g., ibuprofen, cyclooxygenase-2 (COX-2) inhibitors, and naproxen), gabapentin, pregabalin, tramadol, acetaminophen, and aspirin.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the active agents of the invention can be provided in the form of tablets or capsules, or as a solution, emulsion, or suspension. To prepare the oral compositions, the active agents may be formulated to yield a dosage of, e.g., from about 0.05 to about 50 mg/kg daily, or from about 0.05 to about 20 mg/kg daily, or from about 0.1 to about 10 mg/kg daily. These dosages may be orally administered using any of the foregoing preparations and the administration will be accomplished according to the wisdom and judgment of the patient's attending physician.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days. Administration will be accomplished according to the wisdom and judgment of the patient's attending physician.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I).

SCHEME A

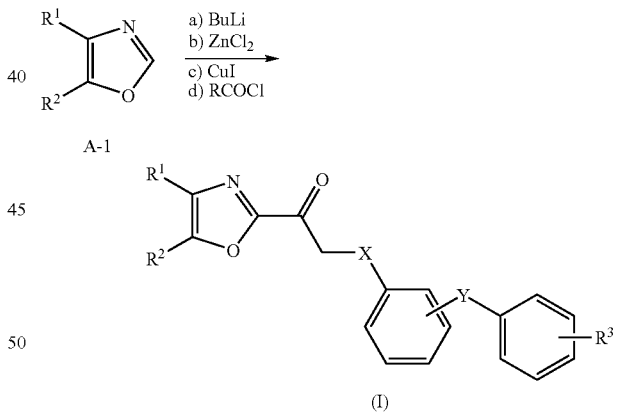

Compounds of Formula (I) are prepared by metallation of the 2-position of substituted oxazoles A-1 and reaction with suitable acid chlorides (See: Harn, N. K. et al. *Tetrahedron Lett.* 1995, 36, 9453-9456).

SCHEME B

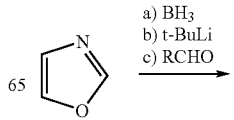

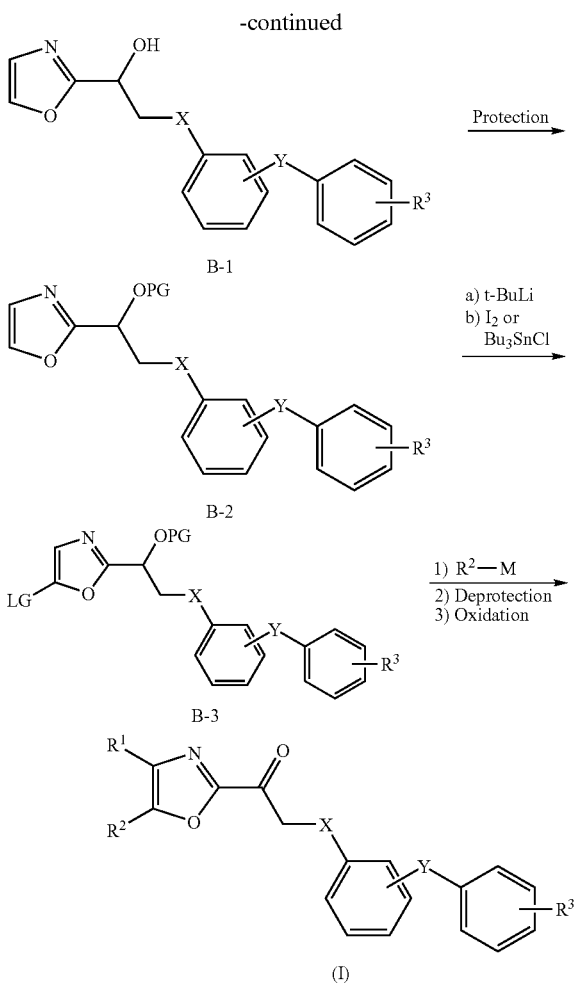

Alternatively, compounds of Formula (I) are prepared by metallation of oxazole and reaction with suitable aldehydes to form alcohols B-1. Protection of the alcohol functionality with a suitable protecting group, PG (such as a silyl protecting group) gives compounds B-2. Metallation of the 5-position of the oxazole and quenching with iodine or tri-butyltin chloride gives compounds B-3, where LG is iodine or —SnBu$_3$. Palladium-mediated coupling with suitable reagents R$^2$—M, where M is —SnBu$_3$, —B(OH)$_2$, I, or Br, followed by deprotection of the alcohol protecting group and oxidation under standard conditions, provides compounds of Formula (I). (See: Boger, D. L. et al. *J. Med. Chem.* 2005, 48, 1849-1856).

Compounds of Formula (I) may be converted to their corresponding salts using methods described in the art. In particular, an amine-containing compound of Formula (I) may be treated with trifluoroacetic acid, HCl, or citric acid in a solvent such as Et$_2$O, CH$_2$Cl$_2$, THF, and MeOH to provide the corresponding salt form.

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following specific examples are provided to further illustrate the invention and various preferred embodiments.

EXAMPLES

General Procedure A. Synthesis of 5-Aryl or heteroaryl oxazole compounds using the stannane route of scheme B.

The stannane intermediate (1 equiv), Pd(PPh$_3$)$_4$ (0.1 equiv), and aryl halide (2 equiv) can be dissolved in anhydrous 1,4-dioxane (8 mL/0.150 mmol of stannane) and the mixture can be warmed to reflux for 24 h under Ar. The mixture is diluted with EtOAc, washed with saturated aqueous NaCl and dried over Na$_2$SO$_4$. Evaporation in vacuo will yield the crude coupling product that may be purified by flash chromatography (SiO$_2$). The resulting product will be, for example the 5-aryl or heteroaryl oxazole having a silyl protected alcohol chain at the 2 position of the oxazole.

General Procedure B. Cleavage of the silyl protecting group and oxidation of the alcohol to produce a 5-aryl or heteroaryl oxazole having a α-keto group at the oxazole 2 position.

The TBS ether (1 equiv) of General Procedure A may be dissolved in THF (3 mL/0.163 mmol of TBS ether), treated with Bu$_4$NF (1 M in THF, 1.2 equiv) and stirred at room temperature for 2 h under Ar. The reaction mixture can be diluted with EtOAc, washed with saturated aqueous NaCl and dried over Na$_2$SO$_4$. Evaporation in vacuo yielded the crude alcohol which can be filtered through a short silica gel pad. The silica gel pad can be washed with 10% EtOAc/hexanes followed by 60% EtOAc/hexanes to afford the alcohol which required no further purification. The alcohol (1 equiv) can be dissolved in CH$_2$Cl$_2$ (3 mL/0.068 mmol of alcohol) or THF (3 mL) and Dess-Martin periodinane (1.5 equiv) may be added. The mixture can be stirred at room temperature for 2 h before silica gel is added and the reaction mixture can be evaporated in vacuo to afford the crude ketone absorbed on silica gel. This mixture can be subsequently purified by flash chromatography (SiO$_2$) yielding the pure α-ketoheterocycle.

General Procedure C. Formation of the acid from the ester of general procedure B.

The ester (1 equiv) was dissolved in a mixture of 3:2 THF/H$_2$O and LiOH (3 equiv) was added. The reaction mixture stirred for 2 h at room temperature before the mixture was made acidic with the addition of aqueous 1 N HCl. The solution was diluted with EtOAc and the organic layer was separated from the aqueous layer. The aqueous layer was extracted with EtOAc. The combined organic extracts were washed with saturated aqueous NaCl and dried over Na$_2$SO$_4$. Evaporation in vacuo yielded the crude acid which was purified by chromatography (SiO$_2$).

General Procedure D. General preparation of a 2-substituted pyridyloxazole.

A solution of 5-(2-pyridyl)oxazole (1.0 equiv) in anhydrous THF (3 mL/0.34 mmol) at −78° C. may be treated dropwise with a solution of n-BuLi in hexanes (2.5 M, 1.2 equiv) under N$_2$ and the resulting solution may be stirred at −78° C. for 35 min. A solution of ZnCl$_2$ in THF (0.5 M, 2 equiv) can be added to the mixture and the mixture is allowed to warm to 0° C. After stirring at 0° C. for 45 min, CuI (1.2 equiv) can be added to the mixture. After the mixture is stirred at 0° C. for 15 min, a solution of the acid chloride (1.2 equiv) in anhydrous THF (2 mL) can be added dropwise, and the mixture can be stirred for an additional 1 h. The reaction mixture may be quenched with addition of saturated aqueous NaHCO$_3$ and extracted with EtOAc. The organic layer can be filtered through diatomaceous earth, dried over anhydrous Na$_2$SO$_4$, filtered and evaporated to yield the crude product, which may be purified by flash chromatography (SiO$_2$).

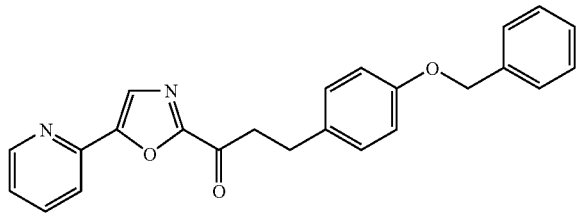

Example 1

1-Oxo-1-[5-(2-pyridyl)oxazol-2-yl]-3-(4-(benzyloxy)phenyl)propane (11a)

3-(4-(Benzyloxy)phenyl)propanoic acid. 4-Hydroxycinnamic acid (700 mg, 4.26 mmol) was dissolved in EtOAc (15 mL) and 10% Pd/C (51 mg, 0.479 mmol) was added. The reaction mixture was stirred under an atmosphere of H$_2$ overnight at room temperature before it was filtered through diatomaceous earth and concentrated in vacuo. No further purification was needed to yield 3-(4-hydroxyphenyl)propanoic acid (700 mg, 99%). A solution of 3-(4-hydroxyphenyl)propanoic acid (700 mg, 4.21 mmol) in anhydrous DMF (16 mL) at 0° C. was treated with a solution of 60% NaH (450 mg, 18.75 mmol) in DMF dropwise. The reaction mixture was stirred for 10 min before benzyl bromide (0.675 mL, 5.68 mmol) was added. The reaction mixture was stirred overnight at room temperature, quenched with aqueous 1 N HCl and extracted with EtOAc. The combined organic layers were washed with saturated aqueous NH$_4$Cl, saturated aqueous NaCl and dried over Na$_2$SO$_4$. Column chromatography (SiO$_2$, 4×9 cm, 20-40% EtOAc-hexanes gradient) afforded 3-(4-(benzyloxy)phenyl)propanoic acid (780 mg, 72%) as a white solid: $^1$H NMR (CDCl$_3$, 500 MHz) 7.44 (d, 2H, J=7.4 Hz), 7.40 (t, 2H, J=7.4 Hz), 7.35-7.32 (m, 1H), 7.14 (d, 2H, J=8.8 Hz), 6.92 (d, 2H, J=8.4 Hz), 5.06 (s, 2H), 2.92 (t, 2H, J=7.7 Hz), 2.66 (t, 2H, J=7.7 Hz); $^{13}$C NMR (CDCl$_3$, 125 MHz) 179.0, 157.3, 137.0, 132.5, 129.2, 128.5, 127.9, 127.4, 114.9, 70.0, 35.8, 29.7. (See: Xue, C.-B.; He, X.; et al. *J. Med. Chem.* 2001, 44, 3351-3354)

1-Oxo-1-[5-(2-pyridyl)oxazol-2-yl]-3-(4-(benzyloxy)phenyl)propane. A solution of 5-(2-pyridyl)oxazole (Saikachi, H., et al. *Chem. Pharm. Bull.* 1969, 27, 793-796; 116 mg, 0.794 mmol) in anhydrous THF (4 mL) at −78° C. was treated dropwise with a solution of n-BuLi in hexanes (1.6 M, 0.64 mL, 0.953 mmol) under N$_2$ and the resulting solution was stirred at −78° C. for 35 min. A solution of ZnCl$_2$ in THF (0.5 M, 1.9 mL, 1.56 mmol) was added and the mixture was allowed to warm to 0° C. After stirring at 0° C. for 45 min, CuI (160 mg, 0.840 mmol) was added. After the mixture was stirred at 0° C. for 15 min, a solution of 3-(4-hydroxyphenyl)propanoyl chloride (1.2 equiv; prepared from 3-(4-(benzyloxy)phenyl)propanoic acid and oxalyl chloride) in anhydrous THF (1.5 mL) was added dropwise, and the mixture was stirred for an additional 1 h. The reaction mixture was quenched with addition of saturated aqueous NaHCO$_3$ and extracted with EtOAc. The organic layer was filtered through diatomaceous earth, dried over anhydrous Na$_2$SO$_4$, filtered and evaporated to yield the crude product. Column chromatography (SiO$_2$, 2.5×5 cm, 10-30% EtOAc-hexanes gradient) followed by PTLC (SiO$_2$, 50% EtOAc-hexanes) afforded the title compound (33%) as a white solid: mp 99-100° C. $^1$H NMR (CDCl$_3$, 400 MHz) 8.67 (app d, J=4.4 Hz, 1H), 7.88 (s, 1H), 7.87-7.85 (m, 1H), 7.81 (td, 1H, J=7.8, 1.8 Hz), 7.44 (d, 2H, J=7.0 Hz), 7.39 (t, 2H, J=7.5 Hz), 7.32 (t, 2H, J=6.8 Hz), 7.19 (d, 2H, J=8.5 Hz), 6.91 (d, 2H, J=8.5 Hz), 5.04 (s, 2H), 3.44 (t, 2H, J=7.4 Hz), 3.06 (t, 2H, J=7.4 Hz); $^{13}$C NMR (CDCl$_3$, 100 MHz) 187.4, 157.2 (2C), 153.2, 150.1, 146.2, 137.1, 137.0, 132.7, 129.4, 128.5, 127.9, 127.4, 126.9, 124.2, 120.4, 114.9, 70.0, 40.9, 28.9; IR (film) $\nu_{max}$ 3097, 2919, 1693, 1602, 1582, 1514, 1470, 1427, 1382, 1253, 1177, 1042, 963, 938, 785, 741, 697 cm$^{-1}$; ESI-TOF m/z 385.1549 (C$_{24}$H$_{20}$N$_2$O$_3$+H$^+$ requires 385.1547).

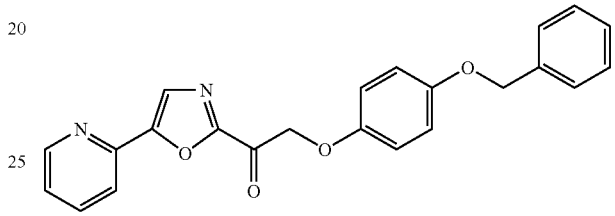

Example 2

2-(4-(Benzyloxy)phenoxy)-1-(5-(pyridin-2-yl)oxazol-2-yl)ethanone (11b)

The title compound was prepared from 5-(2-pyridyl)oxazole and 2-(4-(benzyloxy)phenoxy)acetic acid (commercially available) using General Procedure B. Column chromatography (SiO$_2$, 2.5×6 cm, 20-40% EtOAc-hexanes gradient) followed by PTLC (SiO$_2$, 50% EtOAc-hexanes) afforded 11b (35 mg, 0.09 mmol, 10%) as a pale yellow solid: $^1$H NMR (CDCl$_3$, 500 MHz) 8.70 (app d, 1H, J=4.0 Hz), 8.04 (d, 1H, J=8.1 Hz), 7.86 (td, 1H, J=7.7, 1.5 Hz), 7.55-7.52 (m, 1H), 7.44-7.33 (m, 6H), 6.94-6.89 (m, 4H), 5.45 (s, 2H), 5.03 (s, 2H); ESI-TOF m/z 387.1343 (C$_{23}$H$_{19}$N$_2$O$_4$+H$^+$ requires 387.1345).

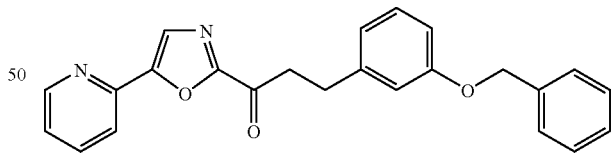

Example 3

1-Oxo-1-[5-(2-pyridyl)oxazol-2-yl]-3-(3-(benzyloxy)phenyl)-propane (11c)

The title compound was prepared from 5-(2-pyridyl)oxazole and 3-(3-(benzyloxy)phenyl)propanoic acid (Bänteli, R.; Brun, I.; et al. *Tetrahedron Lett.* 1999, 40, 2109-2112) using General Procedure B. Column chromatography (SiO$_2$, 2.5×6 cm, 10-20% EtOAc-hexanes gradient) followed by PTLC (SiO$_2$, 50% EtOAc-hexanes) afforded 11c (46 mg, 0.12 mmol, 18%) as a yellow solid: $^1$H NMR (CDCl$_3$, 400

MHz) 8.67 (m, 1H), 7.88 (s, 1H), 7.87-7.85 (m, 1H), 7.81 (td, 1H, J=7.8, 1.8 Hz), 7.45 (d, 2H, J=8.5 Hz), 7.38 (t, 2H, J=7.3 Hz), 7.32 (t, 2H, J=6.8 Hz), 7.22 (t, 2H, J=7.9 Hz), 6.92 (d, 2H, J=2.1 Hz), 6.88 (d, 2H, J=7.6 Hz), 6.83 (dd, 2H, J=7.9, 2.4 Hz), 5.06 (s, 2H), 3.47 (t, 2H, J=7.4 Hz), 3.10 (t, 2H, J=7.4 Hz); $^{13}$C NMR (CDCl$_3$, 100 MHz) 187.2, 158.9, 157.2, 153.4, 150.1, 146.2, 142.0, 137.1, 137.0, 129.5, 128.5, 127.9, 127.5, 127.0, 124.2, 121.0, 120.4, 115.1, 112.5, 69.9, 40.5, 29.7; IR (film) $v_{max}$ 3073, 3032, 2929, 1697, 1601, 1582, 1499, 1468, 1452, 1425, 1380, 1256, 1154, 1027, 784, 737, 695 cm$^{-1}$; ESI-TOF m/z 385.1549 (C$_{24}$H$_{20}$N$_2$O$_3$+H$^+$ requires 385.1547).

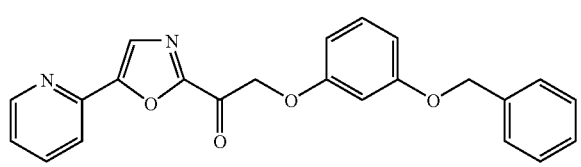 [SMILES: O=C(COc1cccc(OCc2ccccc2)c1)c1ncc(-c2ccccn2)o1]

Example 4

2-(3-(Benzyloxy)phenoxy)-1-(5-(pyridin-2-yl)oxazol-2-yl)ethanone (11d)

The title compound was prepared from 5-(2-pyridyl)oxazole and 2-(3-(benzyloxy)phenoxy)acetic acid (Baker, B. R.; Neenan, J. P. *J. Med. Chem.* 1972, 15, 940-944) using General Procedure B. Column chromatography (SiO$_2$, 2.5×6 cm, 20-40% EtOAc-hexanes gradient) followed by PTLC (SiO$_2$, 50% EtOAc-hexanes) afforded 11d (26 mg, 0.07 mmol, 7%) as a pale yellow solid: $^1$H NMR (CDCl$_3$, 500 MHz) 8.70 (app d, 1H, J=4.0 Hz), 8.03 (d, 1H, J=8.1 Hz), 7.86 (td, 1H, J=7.7, 1.5 Hz), 7.55-7.52 (m, 1H), 7.45-7.32 (m, 6H), 7.22 (t, 1H, J=8.2 Hz), 6.68 (dd, 1H, J=8.2, 2.4 Hz), 6.61 (t, 1H, J=2.2 Hz), 6.54 (dd, 1H, J=7.8, 2.5 Hz), 5.45 (s, 2H), 5.06 (s, 2H); $^{13}$C NMR (CDCl$_3$, 100 MHz) 192.7, 169.7, 162.1 (2C), 158.3, 151.5, 149.2, 137.0, 136.7, 130.3, 128.6, 128.0, 127.5, 122.2, 106.9 (2C), 102.1, 70.1, 67.9; ESI-TOF m/z 387.1349 (C$_{23}$H$_{19}$N$_2$O$_4$+H$^+$ requires 387.1345).

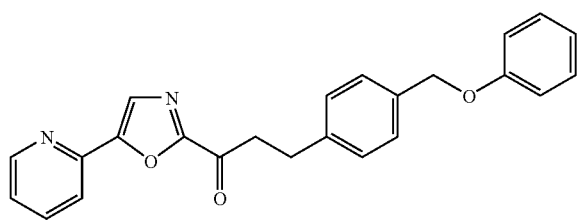 [SMILES: O=C(CCc1ccc(COc2ccccc2)cc1)c1ncc(-c2ccccn2)o1]

Example 5

3-(4-(Phenoxymethyl)phenyl)-1-(5-(pyridin-2-yl)oxazol-2-yl)propan-1-one (11e)

1-Iodo-4-(phenoxymethyl)benzene (S25). A solution of (4-iodophenyl)methanol (2.34 g, 10.0 mmol, 1 equiv) in anhydrous THF (30 mL) at 0° C. was treated with Ph$_3$P (3.4 g, 13.0 mmol, 1.3 equiv) and phenol (1.0 g, 11.0 mmol, 1.1 equiv). After stirring for 5 min, diethyl azodicarboxylate (2.26 g, 13.0 mmol, 1.3 equiv) in 5 mL of anhydrous THF was added dropwise. The reaction mixture was allowed to warm at 25° C. and was stirred for 2 days. Concentration followed by column chromatography (SiO$_2$, 4×10 cm, 5% EtOAc-hexanes) afforded S25 (1.45 g, 4.47 mmol, 45%) as a yellow oil: $^1$H NMR (CDCl$_3$, 400 MHz) 7.74 (d, 2H, J=7.6 Hz), 7.32 (d, 2H, J=7.4 Hz), 7.21 (d, 2H, J=7.4 Hz), 7.01-6.95 (m, 3H), 5.04 (s, 2H); $^{13}$C NMR (CDCl$_3$, 100 MHz) 158.4, 137.6, 136.7, 129.5, 129.2, 121.1, 114.7, 93.4, 69.1.

Ethyl 3-(4-(phenoxymethyl)phenyl)propanoate (S26). A suspension of zinc (150 mg, 2.30 mmol, 2.3 equiv) in anhydrous THF (5 mL) was treated with NiCl$_2$(H$_2$O)$_6$ (45 mg, 0.19 mmol, 0.19 equiv) and ethyl acrylate (206 μL, 1.90 mmol, 1.9 equiv). The reaction mixture was warmed at 65° C. and pyridine (115 μL, 1.42 mmol, 1.42 equiv) was added. After 15 min, 1-iodo-4-(phenoxymethyl)benzene (S25, 324 mg, 1.0 mmol, 1 equiv) in 5 mL of anhydrous THF was added and the reaction mixture was stirred at 65° C. for 56 h. The reaction mixture was quenched with saturated aqueous NaHCO$_3$ and extracted with EtOAc. The organic layer was dried over Na$_2$SO$_4$, filtered and concentrated. Column chromatography (SiO$_2$, 4×10 cm, 5% EtOAc-hexanes) afforded S26 (200 mg, 0.70 mmol, 70%) as a yellow oil: $^1$H NMR (CDCl$_3$, 400 MHz) 7.38 (d, 2H, J=7.9 Hz), 7.30 (t, 2H, J=7.3 Hz), 7.25 (d, 2H, J=7.9 Hz), 7.00-6.96 (m, 3H), 5.04 (s, 2H), 4.15 (q, 2H, J=7.1 Hz), 2.98 (t, 2H, J=7.7 Hz), 2.64 (t, 2H, J=7.7 Hz), 1.26 (t, 3H, J=7.1 Hz); $^{13}$C NMR (CDCl$_3$, 100 MHz) 178.8, 158.7, 139.9, 135.1, 129.5, 128.5, 127.8, 120.9, 114.7, 69.7, 35.4, 30.2.

3-(4-(Phenoxymethyl)phenyl)propanoic acid (S27). A solution of ethyl 3-(4-(phenoxymethyl)phenyl)propanoate (S26, 185 mg, 0.65 mmol) in a THF/MeOH (1/1, 10 mL) was treated with aqueous 4 N NaOH (1 mL) and was stirred overnight at 25° C. The reaction mixture was concentrated, diluted with aqueous 1 N HCl and extracted with CH$_2$Cl$_2$. The organic layer was dried over Na$_2$SO$_4$, filtered and concentrated to afford S27 (115 mg, 0.45 mmol, 69%) as a pale yellow solid: $^1$H NMR (CDCl$_3$, 500 MHz) 7.39 (d, 2H, J=7.7 Hz), 7.30 (t, 2H, J=7.4 Hz), 7.25 (d, 2H, J=7.7 Hz), 7.00-6.96 (m, 3H), 5.05 (s, 2H), 2.99 (t, 2H, J=7.7 Hz), 2.71 (t, 2H, J=7.7 Hz); $^{13}$C NMR (CDCl$_3$, 125 MHz) 178.8, 158.7, 139.9, 135.1, 129.5, 128.5, 127.8, 120.9, 114.7, 69.7, 35.4, 30.2.

3-(4-(Phenoxymethyl)phenyl)-1-(5-(pyridin-2-yl)oxazol-2-yl)propan-1-one. The title compound (11e) was prepared from 5-(2-pyridyl)oxazole and 3-(4-(phenoxymethyl)phenyl)propanoic acid (S27) using General Procedure B. PTLC (SiO$_2$, 50% EtOAc-hexanes) afforded 11e (40 mg, 0.10 mmol, 32%) as a pale yellow solid: $^1$H NMR (CDCl$_3$, 400 MHz) 8.68-8.66 (m, 1H), 7.89 (s, 1H), 7.88-7.85 (m, 1H), 7.81 (td, 1H, J=7.9, 1.5 Hz), 7.38 (d, 2H, J=8.2 Hz), 7.34-7.27 (m, 5H), 6.99-6.94 (m, 3H), 5.03 (s, 2H), 3.48 (t, 2H, J=7.4 Hz), 3.13 (t, 2H, J=7.5 Hz); $^{13}$C NMR (CDCl$_3$, 100 MHz) 187.2, 158.7, 157.1, 153.3, 150.1, 146.2, 140.1, 137.1, 137.0, 129.4, 128.6, 127.8, 126.9, 124.1, 120.8, 120.3, 114.7, 69.6, 40.5, 29.3; IR (film) $v_{max}$ 2923, 1694, 1601, 1504, 1470, 1428, 1380, 1241, 1171, 1125, 1080, 1032, 1017, 989, 962, 911, 869, 815, 788, 760, 693 cm$^{-1}$; ESI-TOF m/z 385.1550 (C$_{24}$H$_{20}$N$_2$O$_3$+H$^+$ requires 385.1547).

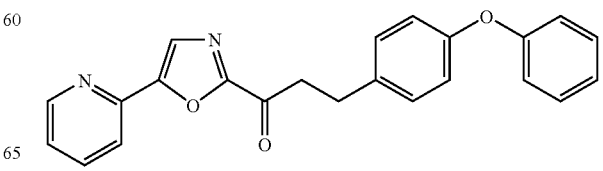

Example 6

1-Oxo-1-[5-(2-pyridyl)oxazol-2-yl]-3-(4-phenoxyphenyl)propane (11f)

Ethyl (E)-3-(4-phenoxyphenyl)acrylate (S28). A solution of triethylphosphonoacetate (1.40 g, 6.25 mmol, 1.25 equiv) in 20 mL of anhydrous THF at −78° C. was treated with n-BuLi (2.4 M in hexanes, 3.26 mL, 7.82 mmol, 1.5 equiv). After stirring for 35 min, 4-phenoxybenzaldehyde (990 mg, 5.0 mmol, 1 equiv) in anhydrous THF (15 mL) was added dropwise. The reaction mixture was allowed to warm at 25° C. and was stirred overnight. The reaction was quenched with saturated aqueous $NH_4Cl$ and extracted with EtOAc. The organic layer was dried over $Na_2SO_4$, filtered and concentrated. Column chromatography ($SiO_2$, 4×8 cm, 10% EtOAc-hexanes) afforded S28 (540 mg, 2.03 mmol, 67%) as a colorless oil: $^1$H NMR ($CDCl_3$, 500 MHz) 7.66 (d, 1H, J=16.2 Hz), 7.50 (d, 2H, J=8.8 Hz), 7.38 (dd, 2H, J=8.8, 7.6 Hz), 7.17 (t, 1H, J=7.4 Hz), 7.07-7.05 (m, 2H), 6.98 (d, 2H, J=8.8 Hz), 6.35 (d, 1H, J=16.2 Hz), 4.26 (q, 2H, J=7.0 Hz), 1.35 (t, 3H, J=7.1 Hz).

Ethyl 3-(4-phenoxyphenyl)propanoate (S29). A solution of ethyl (E)-3-(4-benzylphenyl)acrylate (S28, 500 mg, 1.97 mmol) in EtOH (20 mL) was treated with 10% Pd/C (45 mg) and purged with $H_2$. The reaction mixture was stirred overnight at 25° C., filtered through Celite and concentrated to afford S29 (502 mg, 1.96 mmol, 99%) as a yellow oil: $^1$H NMR ($CDCl_3$, 500 MHz) 7.34 (dd, 2H, J=8.4, 7.4 Hz), 7.17 (d, 2H, J=8.4 Hz), 7.09 (dt, 1H, J=7.7, 1.1 Hz), 7.00 (dd, 2H, J=8.8, 1.1 Hz), 6.95 (d, 2H, J=8.8 Hz), 4.14 (q, 2H, J=7.0 Hz), 2.94 (t, 2H, J=7.7 Hz), 2.63 (t, 2H, J=7.7 Hz), 1.25 (t, 3H, J=7.0 Hz).

3-(4-Phenoxyphenyl)propanoic acid (S30). A solution of ethyl 3-(4-phenoxyphenyl)propanoate (S29, 500 mg, 1.95 mmol) in THF/MeOH (1/1, 8 mL) was treated with aqueous 4 N NaOH (0.5 mL) and was stirred for 20 h at 25° C. The reaction mixture was concentrated, diluted with aqueous 1 N HCl and extracted with $CH_2Cl_2$. The organic layer was dried over $Na_2SO_4$, filtered and concentrated to afford S30 (390 mg, 1.61 mmol, 82%) as a white solid: $^1$H NMR ($CDCl_3$, 500 MHz) 7.34 (dd, 2H, J=8.4, 7.4 Hz), 7.18 (d, 2H, J=8.4 Hz), 7.10 (dt, 1H, J=7.7, 1.1 Hz), 7.00 (dd, 2H, J=8.8, 1.1 Hz), 6.95 (d, 2H, J=8.4 Hz), 2.96 (t, 2H, J=7.7 Hz), 2.70 (t, 2H, J=7.7 Hz); $^{13}$C NMR ($CDCl_3$, 125 MHz) 179.2, 157.3, 155.6, 135.0, 129.7, 129.5, 123.1, 119.0, 118.7, 35.7, 29.8.

1-Oxo-1-[5-(2-pyridyl)oxazol-2-yl]-3-(4-phenoxyphenyl)propane. The title compound (11f) was prepared from 5-(2-pyridyl)oxazole and 3-(4-phenoxyphenyl)propanoic acid (S30) using General Procedure B. PTLC ($SiO_2$, 50% EtOAc-hexanes) afforded 11f (83 mg, 0.22 mmol, 37%) as a pale yellow solid: $^1$H NMR ($CDCl_3$, 500 MHz) 8.69 (m, 1H), 7.89-7.86 (m, 2H), 7.82 (td, 1H, J=7.8, 1.8 Hz), 7.34-7.30 (m, 3H), 7.24 (d, 2H, J=8.5 Hz), 7.10-7.07 (m, 1H), 6.98 (d, 2H, J=12.1 Hz), 6.94 (d, 2H, J=8.6 Hz), 3.47 (t, 2H, J=7.4 Hz), 3.10 (t, 2H, J=7.4 Hz); $^{13}$C NMR ($CDCl_3$, 100 MHz) 187.2, 157.4, 157.1, 155.5, 153.3, 150.1, 146.2, 137.1, 135.2, 129.7, 129.6, 126.9, 124.1, 123.0, 120.4, 119.1, 118.6, 40.7, 29.0; IR (film) $v_{max}$ 3055, 2930, 1698, 1589, 1504, 1488, 1425, 1380, 1237, 1167, 1065, 871, 784, 692 cm$^{-1}$; ESI-TOF m/z 371.1388 ($C_{23}H_{18}N_2O_3$+H$^+$ requires 371.1396).

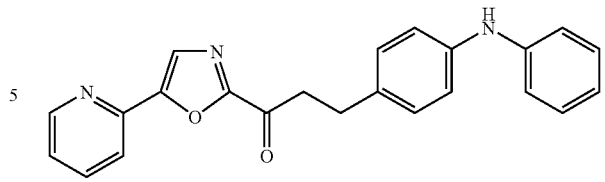

Example 7

1-Oxo-1-[5-(2-pyridyl)oxazol-2-yl]-3-(4-(phenylamino)phenyl)-propane (11g)

Methyl (E)-3-(4-nitrophenyl)acrylate (S31). A solution of p-nitrocinnamic acid (3.86 g, 20.0 mmol) in MeOH (50 mL) was treated with $H_2SO_4$ (2 mL) and was stirred at 25° C. for 24 h. Concentration afforded S31 (4.10 g, 19.8 mmol, 99%) as a yellow solid: $^1$H NMR ($CDCl_3$, 500 MHz) 8.26 (d, 2H, J=8.4 Hz), 7.12 (d, 1H, J=16.1 Hz), 7.68 (d, 2H, J=8.8 Hz), 6.58 (d, 1H, J=16.1 Hz), 3.85 (s, 3H).

Methyl 3-(4-aminophenyl)propanoate (S32). A solution of methyl (E)-3-(4-nitrophenyl)acrylate (S31, 4.10 g, 19.8 mmol) in MeOH (30 mL) and THF (30 mL) was treated with 10% Pd/C (400 mg). The reaction mixture was purged with $H_2$ and was stirred at 25° C. for 10 h. The suspension was filtered through diatomaceous earth and concentrated to afford S32 (3.40 g, 19.0 mmol, 95%) as a yellow solid: $^1$H NMR ($CDCl_3$, 500 MHz) 6.99 (d, 2H, J=8.2 Hz), 6.63 (d, 2H, J=8.4 Hz), 3.60 (s, 3H), 2.85 (t, 2H, J=7.7 Hz), 2.58 (t, 2H, J=7.7 Hz); $^{13}$C NMR ($CDCl_3$, 125 MHz) 173.5, 144.6, 130.5, 129.1, 115.3, 51.5, 36.1, 30.1.

Methyl 3-(4-(phenylamino)phenyl)propanoate (S33). A solution of PhB(OH)$_2$ (550 mg, 4.51 mmol, 1.5 equiv), Cu(OAc)$_2$ (110 mg, 0.61 mmol, 0.2 equiv) and myristic acid (137 mg, 0.60 mmol, 0.2 equiv) in anhydrous toluene (6 mL) was treated with 2,6-lutidine (0.35 mL, 3.0 mmol, 1 equiv) and methyl 3-(4-aminophenyl)propanoate (S32, 537 mg, 3.0 mmol, 1 equiv). The reaction mixture was stirred for 24 h at 25° C. and was concentrated. Column chromatography ($SiO_2$, 4×5 cm, 20% EtOAc-hexanes) afforded S33 (660 mg, 2.59 mmol, 87%) as a yellow oil: $^1$H NMR ($CDCl_3$, 500 MHz) 7.28-7.25 (m, 2H), 7.12 (d, 2H, J=8.4 Hz), 7.05 (dd, 2H, J=7.7, 1.1 Hz), 7.03 (d, 2H, J=8.4 Hz), 6.95-6.90 (m, 1H), 3.70 (s, 3H), 2.92 (t, 2H, J=7.7 Hz), 2.66 (t, 2H, J=7.7 Hz); $^{13}$C NMR ($CDCl_3$, 125 MHz) 173.5, 143.9, 141.2, 133.2, 129.3, 129.1, 120.6, 118.3, 117.2, 51.6, 35.9, 30.2.

Methyl 3-(4-(tert-butoxycarbonyl(phenyl)amino)phenyl)propanoate (S34). A solution of methyl 3-(4-(phenylamino)phenyl)propanoate (S33, 560 mg, 2.20 mmol, 1 equiv) in anhydrous THF (6 mL) was treated with DMAP (54 mg, 0.44 mmol, 0.2 equiv) and (BOC)$_2$O (671 mg, 3.07 mmol, 1.4 equiv). The reaction mixture was warmed at 70° C. for 48 h and (BOC)$_2$O (800 mg, 3.66 mmol, 1.6 equiv) was added. The reaction mixture was warmed at 65° C. for 10 h and (BOC)$_2$O (800 mg, 3.66 mmol, 1.6 equiv) was added. After stirring for 8 h, the reaction mixture was concentrated. Column chromatography ($SiO_2$, pretreated with 1% $Et_3$N-hexanes, 4×8 cm, 10-20% EtOAc-hexanes gradient) afforded S34 (760 mg, 2.14 mmol, 97%) as a yellow oil: $^1$H NMR ($CDCl_3$, 400 MHz) 7.33-7.29 (m, 2H), 7.22-7.14 (m, 7H), 3.67 (s, 3H), 2.93 (t, 2H, J=7.6 Hz), 2.62 (t, 2H, J=7.6 Hz), 1.45 (s, 9H); $^{13}$C NMR ($CDCl_3$, 100 MHz) 173.2, 153.8, 143.0, 141.2, 137.8, 128.6, 128.5, 126.9 (2C), 125.6, 81.1, 51.6, 35.6, 30.3, 28.2.

3-(4-(tert-Butoxycarbonyl(phenyl)amino)phenyl)propanoic acid (S35). A solution of methyl 3-(4-(tert-butoxycarbonyl(phenyl)amino)phenyl)propanoate (S34, 390 mg, 1.10 mmol) in a mixture of THF/H$_2$O/MeOH (3/1/0.4, 4 mL), was treated with NaOH (100 mg, 2.5 mmol) and was stirred for 4 h at 25° C. The reaction mixture was concentrated, diluted with aqueous 1 N HCl and extracted with CH$_2$Cl$_2$. The organic layer was washed with saturated aqueous NaCl, dried over Na$_2$SO$_4$, filtered and concentrated to afford S35 (370 mg, 1.08 mmol, 99%) as a yellow oil: $^1$H NMR (CDCl$_3$, 400 MHz) 7.34-7.29 (m, 2H), 7.23-7.15 (m, 7H), 2.94 (t, 2H, J=7.6 Hz), 2.66 (t, 2H, J=7.6 Hz), 1.46 (s, 9H); $^{13}$C NMR (CDCl$_3$, 100 MHz) 178.7, 153.9, 142.9, 141.2, 137.6, 128.6, 128.5, 126.9 (2C), 125.6, 81.1, 35.5, 30.0, 28.2.

tert-Butyl 4-(3-oxo-3-(5-(pyridin-2-yl)oxazol-2-yl)propyl)phenyl(phenyl)-carbamate (S36). The title compound was prepared from 5-(2-pyridyl)oxazole and 3-(4-(tent-butoxycarbonyl(phenyl)amino)phenyl)propanoic acid (S35) using general procedure B. PTLC (SiO$_2$, 50% EtOAc-hexanes +1% Et$_3$N) afforded S36 (87 mg, 0.185 mmol, 40%) as a yellow oil: $^1$H NMR (CDCl$_3$, 600 MHz) 8.67 (app d, 1H, J=4.8 Hz), 7.87-7.85 (m, 2H), 7.81 (td, 1H, J=7.8, 1.8 Hz), 7.33-7.28 (m, 3H), 7.22-7.13 (m, 7H), 3.45 (t, 2H, J=7.7 Hz), 3.09 (t, 2H, J=7.4 Hz), 1.44 (s, 9H); $^{13}$C NMR (CDCl$_3$, 150 MHz) 187.2, 157.2, 153.8, 153.3, 150.1, 146.2, 143.0, 141.2, 137.7, 137.1, 128.7, 128.6, 127.0, 126.9, 125.5, 124.1, 120.4, 81.1, 40.5, 29.1, 28.2; IR (film) v$_{max}$ 2977, 1709, 1595, 1575, 1512, 1469, 1425, 1367, 1337, 1161, 1056, 1019, 914, 850, 785, 735, 695 cm$^{-1}$; ESI-TOF m/z 492.1897 (C$_{28}$H$_{27}$N$_3$O$_4$+ Na$^+$ requires 492.1894).

1-Oxo-1-[5-(2-pyridyl)oxazol-2-yl]-3-(4-(phenylamino)phenyl)propane (11g). A solution of tert-butyl 4-(3-oxo-3-(5-(pyridin-2-yl)oxazol-2-yl)propyl)phenyl-(phenyl)carbamate (S36, 26 mg, 0.055 mmol) in anhydrous CH$_2$Cl$_2$ (0.8 mL) was treated with TFA (0.2 mL) and was stirred for 1 h at 0° C. The reaction mixture was allowed to warm at 25° C. and was stirred for 2 h. The reaction mixture was concentrated, diluted with saturated aqueous NaHCO$_3$ and extracted with CH$_2$Cl$_2$. The organic layer was dried over Na$_2$SO$_4$, filtered and concentrated. Column chromatography (SiO$_2$, 1×3 cm, pretreated with 1% Et$_3$N-hexanes, 10-25% EtOAc-hexanes gradient) afforded 11g (14 mg, 0.038 mmol, 70%) as a pale yellow solid: $^1$H NMR (CDCl$_3$, 500 MHz) 8.67 (app d, 1H, J=4.0 Hz), 7.89-7.86 (m, 2H), 7.81 (td, 1H, J=7.7, 1.8 Hz), 7.33-7.31 (m, 1H), 7.25 (dd, 2H, J=8.4, 7.3 Hz), 7.18 (d, 2H, J=8.4 Hz), 7.04-7.01 (m, 4H), 6.90 (t, 1H, J=7.3 Hz), 5.68 (br s, 1H), 3.45 (t, 2H, J=7.7 Hz), 3.07 (t, 2H, J=7.7 Hz); $^{13}$C NMR (CDCl$_3$, 150 MHz) 187.5, 157.3, 153.3, 150.1, 146.3, 143.5, 141.3, 137.1, 133.1, 129.3 (2C), 126.9, 124.1, 120.6, 120.4, 118.4, 117.3, 40.9, 29.1, 28.2; IR (film) v$_{max}$ 3389, 3053, 2925, 1698, 1598, 1519, 1495, 1469, 1425, 1380, 1311, 1176, 1152, 1118, 1064, 991, 911, 784, 738, 694 cm$^{-1}$; ESI-TOF m/z 369.1475 (C$_{23}$H$_{19}$N$_3$O$_2$+ requires 369.1477).

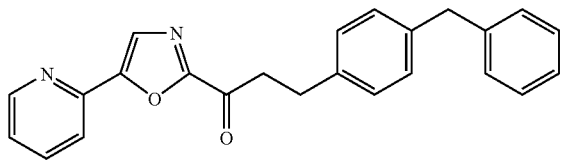 [SMILES: O=C(CCc1ccc(Cc2ccccc2)cc1)c1ncc(-c2ccccn2)o1]

Example 8

1-Oxo-1-[5-(2-pyridyl)oxazol-2-yl]-3-(4-benzylphenyl)propane (11h)

1-Benzyl-4-bromobenzene (S37). A solution of 4-bromobenzophenone (2.62 g, 10.0 mmol, 1 equiv) in anhydrous CH$_2$Cl$_2$ (25 mL) was treated with triflic acid (0.27 mL, 3.0 mmol, 0.3 equiv) and Et$_3$SiH (3.60 g, 31.0 mmol, 3.1 equiv) in 8 mL of anhydrous CH$_2$Cl$_2$. After stirring for 12 h at 25° C., the reaction mixture was quenched with NaHCO$_3$ and extracted with CH$_2$Cl$_2$. The organic layer was dried over Na$_2$SO$_4$, filtered and concentrated. Column chromatography (SiO$_2$, 4×13 cm, 2% EtOAc-hexanes) afforded S37 (2.43 g, 9.83 mmol, 98%) as a pale yellow oil: $^1$H NMR (CDCl$_3$, 500 MHz) 7.43 (d, 2H, J=8.4 Hz), 7.33 (t, 2H, J=7.3 Hz), 7.26 (t, 1H, J=7.3 Hz), 7.24 (d, 2H, J=8.2 Hz), 7.19 (t, 2H, J=7.0 Hz), 7.09 (t, 2H, J=8.4 Hz); $^{13}$C NMR (CDCl$_3$, 125 MHz) 140.4, 140.1, 131.5, 130.6, 128.8, 128.5, 126.3, 119.9, 41.3.

Ethyl (E)-3-(4-benzylphenyl)acrylate (S38). A solution of 1-benzyl-4-bromobenzene (S37, 740 mg, 3.0 mmol, 1 equiv) in Bu$_3$N (0.7 mL) was treated with Ph$_3$P (15 mg, 0.06 mmol, 0.02 equiv) and Pd(OAc)$_2$ (8 mg). After 5 min stirring at 25° C., ethyl acrylate (620 mg, 5.7 mmol, 1.9 equiv) in Bu$_3$N (0.4 mL) was added. The reaction mixture was warmed at 110° C. for 3 h. Pd(OAc)$_2$ (18 mg) was added and the reaction was warmed for 24 h at 110° C. The reaction was quenched with H$_2$O and extracted with CH$_2$Cl$_2$. The organic layer was washed with aqueous 1 N HCl, dried over Na$_2$SO$_4$, filtered and concentrated. Column chromatography (SiO$_2$, 4×6 cm, 2% EtOAc-hexanes) afforded S38 (540 mg, 2.03 mmol, 67%) as a colorless oil: $^1$H NMR (CDCl$_3$, 400 MHz) 7.67 (d, 1H, J=16.1 Hz), 7.46 (d, 2H, J=7.6 Hz), 7.33-7.29 (m, 3H), 7.25-7.19 (m, 5H), 6.40 (d, 1H, J=16.1 Hz), 4.27 (q, 2H, J=7.0 Hz), 4.01 (s, 2H), 1.35 (t, 3H, J=7.0 Hz).

Ethyl 3-(4-benzylphenyl)propanoate (S39). A solution of ethyl (E)-3-(4-benzylphenyl)acrylate (S38, 500 mg, 1.88 mmol) in EtOAc (15 mL) was treated with 10% Pd/C (45 mg) and was purged with H$_2$. After stirring for 10 h at 25° C., the reaction mixture was concentrated. Column chromatography (SiO$_2$, 4×6 cm, 2% EtOAc-hexanes) afforded S39 (350 mg, 1.31 mmol, 70%) as a colorless oil: $^1$H NMR (CDCl$_3$, 400 MHz) 7.30 (t, 2H, J=7.3 Hz), 7.23-7.19 (m, 3H), 7.14 (s, 4H), 4.15 (q, 2H, J=7.0 Hz), 3.97 (s, 2H), 2.94 (t, 2H, J=7.6 Hz), 2.63 (t, 2H, J=7.4 Hz), 1.25 (t, 3H, J=7.0 Hz); $^{13}$C NMR (CDCl$_3$, 100 MHz) 172.9, 141.2, 139.0, 138.2, 129.0, 128.9, 128.4 (2C), 126.0, 60.4, 41.5, 35.9, 30.5, 14.2.

3-(4-Benzylphenyl)propanoic acid (S40). A solution of ethyl 3-(4-benzylphenyl)propanoate (S39, 320 mg, 1.19 mmol) in THF/MeOH (1/1, 10 mL) was treated with aqueous 4 N NaOH (1 mL) and stirred for 3 h at 25° C. The reaction mixture was concentrated, diluted with aqueous 1 N HCl and extracted with CH$_2$Cl$_2$. The organic layer was dried over Na$_2$SO$_4$, filtered and concentrated to afford S40 (260 mg, 1.08 mmol, 91%) as a white solid: $^1$H NMR (CDCl$_3$, 500 MHz) 7.27-7.06 (m, 9H), 3.91 (s, 2H), 2.86 (br s, 2H), 2.59 (br s, 2H); $^{13}$C NMR (CDCl$_3$, 100 MHz) 179.9, 141.1, 138.8, 138.4, 128.9, 128.8, 128.4, 128.2, 126.0, 41.4, 36.9, 30.7.

1-Oxo-1-[5-(2-pyridyl)oxazol-2-yl]-3-(4-benzylphenyl)propane (11h). This material was prepared from 5-(2-pyridyl)oxazole and 3-(4-benzylphenyl)propanoic acid (S40) using General Procedure B. PTLC (SiO$_2$, 50% EtOAc-hexanes) afforded 11h (95 mg, 0.59 mmol, 59%) as a light tan oil: $^1$H NMR (CDCl$_3$, 500 MHz) 8.68 (app d, 1H, J=4.8 Hz), 7.88 (s, 1H), 7.84 (d, 1H, J=7.7 Hz), 7.81 (td, 1H, J=7.7, 1.8 Hz), 7.33-7.27 (m, 3H), 7.21-7.12 (m, 7H), 3.96 (s, 2H), 3.45 (t, 2H, J=7.7 Hz), 3.09 (t, 2H, J=7.7 Hz); $^{13}$C NMR (CDCl$_3$, 125 MHz) 187.3, 157.1, 153.2, 150.0, 146.1, 141.1, 139.0, 138.0, 137.0, 129.0, 128.8, 128.5, 128.3, 126.9, 125.9, 124.1, 120.3, 41.4, 40.6, 29.2; IR (film) v$_{max}$ 3025, 2920, 1694, 1601, 1574, 1516, 1494, 1468, 1426, 1381, 1283, 1151, 1118, 1064, 990, 963, 936, 913, 849, 784, 727, 696 cm$^{-1}$; ESI-TOF m/z 369.1600 (C$_{24}$H$_{20}$N$_2$O$_2$+H$^+$ requires 369.1597).

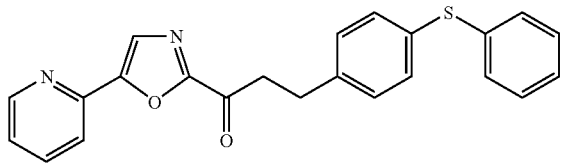 [SMILES: O=C(CCc1ccc(Sc2ccccc2)cc1)c1ncc(-c2ccccn2)o1]

Example 9

1-Oxo-1-[5-(2-pyridyl)oxazol-2-yl]-3-(4-(phenylthio)phenyl)propane (11i)

4-(Phenylthio)benzaldehyde (S41). A solution of 4-fluorobenzaldehyde (2.2 g, 17.7 mmol, 1 equiv) in anhydrous DMF (25 mL) was treated with benzenethiol (1.7 mL, 16.6 mmol, 0.93 equiv) and $K_2CO_3$ (2.8 g, 20.3 mmol, 1.14 equiv). After stirring for 5 h at 130° C., the reaction mixture was washed with saturated aqueous $NH_4Cl$ and extracted with EtOAc. The organic layer was dried over $Na_2SO_4$, filtered and concentrated. Column chromatography ($SiO_2$, 4×7 cm, 10% EtOAc-hexanes) afforded S41 (3.45 g, 16.1 mmol, 91%) as a yellow oil: $^1H$ NMR ($CDCl_3$, 400 MHz) 9.91 (s, 1H), 7.72 (d, 2H, J=8.2 Hz), 7.55-7.52 (m, 2H), 7.44-7.42 (m, 2H), 7.24 (d, 2H, J=8.2 Hz); $^{13}C$ NMR ($CDCl_3$, 100 MHz) 191.2, 147.2, 134.3, 133.6, 131.2, 130.1, 129.8, 129.1, 127.1.

Ethyl (E)-3-(4-(phenylthio)phenyl)acrylate (S42). The title compound was prepared from 4-(phenylthio)benzaldehyde (S41) and triethylphosphonoacetate using the procedure described for ethyl-(E)-3-(4-benzylphenyl)acrylate (S38). Column chromatography ($SiO_2$, 4×8 cm, 10% EtOAc-hexanes) afforded S42 (1.55 g, 5.5 mmol, 84%) as a yellow oil: $^1H$ NMR ($CDCl_3$, 400 MHz) 9.91 (s, 1H), 7.62 (d, 1H, J=15.8 Hz), 7.46-7.21 (m, 9H), 6.38 (d, 1H, J=15.8 Hz); $^{13}C$ NMR ($CDCl_3$, 100 MHz) 166.8, 143.6, 140.0, 133.4, 132.7, 132.3, 129.4, 129.1, 128.5, 128.0, 117.8, 60.4, 14.2.

Ethyl 3-(4-(phenylthio)phenyl)propanoate (S43). A solution of ethyl (E)-3-(4-(phenylthio)phenyl)acrylate (S42, 440 mg, 1.55 mmol, 1 equiv) in anhydrous EtOH (12 mL) at 0° C. was treated with $BiCl_3$ (252 mg, 0.8 mmol, 0.5 equiv) and $NaBH_4$ (243 mg, 6.4 mmol, 4 equiv). The reaction mixture was allowed to warm at 25° C. and was stirred for 2 h. The reaction was quenched with saturated aqueous $NH_4Cl$ and extracted with $CH_2Cl_2$. The organic layer was dried over $Na_2SO_4$, filtered and concentrated. Column chromatography ($SiO_2$, 4×5 cm, 5% EtOAc-hexanes) afforded S43 (390 mg, 1.36 mmol, 88%) as a pale yellow oil: $^1H$ NMR ($CDCl_3$, 400 MHz) 7.32-7.21 (m, 7H), 7.16 (d, 2H, J=8.2 Hz), 4.13 (q, 2H, J=7.1 Hz), 2.94 (t, 2H, J=7.7 Hz), 2.62 (t, 2H, J=7.7 Hz), 1.24 (t, 2H, J=7.1 Hz); $^{13}C$ NMR ($CDCl_3$, 100 MHz) 172.7, 139.9, 136.3, 132.8, 131.7, 130.4, 129.2, 129.1, 126.7, 60.4, 35.7, 30.5, 14.2.

3-(4-(Phenylthio)phenyl)propanoic (S44). The title compound was prepared from ethyl 3-(4-(phenylthio)phenyl)propanoate (S43) using the procedure described for 3-(4-phenoxyphenyl)propanoic acid (S30) to afford S44 (320 mg, 1.24 mmol, 98%) as a white solid: $^1H$ NMR ($CDCl_3$, 400 MHz) 7.35-7.29 (m, 6H), 7.27-7.24 (m, 1H), 7.17 (d, 2H, J=8.2 Hz), 2.96 (t, 2H, J=7.7 Hz), 2.70 (t, 2H, J=7.7 Hz); $^{13}C$ NMR ($CDCl_3$, 100 MHz) 179.2, 139.3, 136.1, 133.2, 131.6, 130.5, 129.2, 129.1, 126.8, 35.4, 30.0.

1-Oxo-1-[5-(2-pyridyl)oxazol-2-yl]-3-(4-(phenylthio)phenyl)propane. The title compound was prepared from 5-(2-pyridyl)oxazole and 3-(4-(phenylthio)phenyl)propanoic acid (S44) using General Procedure B. PTLC ($SiO_2$, 50% EtOAc-hexanes) afforded 11i (50 mg, 0.13 mmol, 33%) as an orange solid: $^1H$ NMR ($CDCl_3$, 500 MHz) 8.68-8.66 (m, 1H), 7.88 (s, 1H), 7.88-7.85 (m, 1H), 7.82 (td, 1H, J=7.7, 1.8 Hz), 7.34-7.28 (m, 7H), 7.24-7.20 (m, 2H), 3.46 (t, 2H, J=7.4 Hz), 3.10 (t, 2H, J=7.4 Hz); $^{13}C$ NMR ($CDCl_3$, 125 MHz) 187.1, 157.1, 153.4, 150.1, 146.2, 139.7, 137.1, 136.3, 132.9, 131.8, 130.4, 129.4, 129.1, 126.9, 126.7, 124.2, 120.4, 40.4, 29.2; IR (film) $v_{max}$ 3054, 2925, 2855, 1698, 1601, 1581, 1505, 1470, 1427, 1381, 1282, 1083, 990, 963, 913, 818, 784, 740, 691 $cm^{-1}$; ESI-TOF m/z 387.1170 ($C_{23}H_{18}N_2O_2S+H^+$ requires 387.1162).

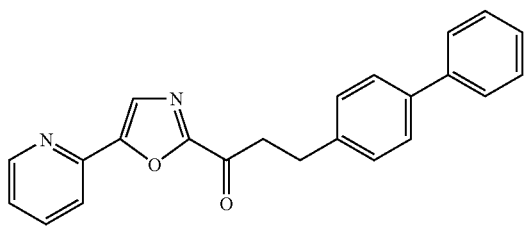 [SMILES: O=C(CCc1ccc(-c2ccccc2)cc1)c1ncc(-c2ccccn2)o1]

Example 10

1-Oxo-1-[5-(2-pyridyl)oxazol-2-yl]-3-(4-biphenyl)propane (11j)

Ethyl (E)-3-(biphenyl-4-yl)acrylate (S45). The title compound was prepared from 4-biphenylcarboxaldehyde and triethylphosphonoacetate using the procedure described for ethyl (E)-3-(4-benzylphenyl)acrylate (S38). Column chromatography ($SiO_2$, 4×12 cm, 5% EtOAc-hexanes) afforded S45 (2.90 g, 11.5 mmol, 83%) as a yellow oil: $^1H$ NMR ($CDCl_3$, 400 MHz) 166.9, 144.0, 142.8, 140.0, 133.3, 128.8, 128.4, 127.7, 127.4, 126.9, 118.0, 60.4, 14.2.

Ethyl 3-(4-biphenyl)propanoate (S46). The title compound was prepared from ethyl (E)-3-(4-biphenyl)acrylate (S45) using the procedure described for ethyl 3-(4-benzylphenyl)propanoate (S39) to afford S46 (1.0 g, 3.93 mmol, 90%) as a pale yellow oil: $^1H$ NMR ($CDCl_3$, 400 MHz) 7.60 (d, 2H, J=7.7 Hz), 7.54 (d, 2H, J=8.2 Hz), 7.45 (t, 2H, J=7.7 Hz), 7.37-7.34 (m, 1H), 7.30 (d, 2H, J=7.9 Hz), 4.16 (q, 2H, J=7.0 Hz), 3.01 (t, 2H, J=7.7 Hz), 2.68 (t, 2H, J=7.6 Hz), 1.26 (t, 3H, J=7.1 Hz); $^{13}C$ NMR ($CDCl_3$, 100 MHz) 172.9, 140.9, 139.6, 139.1, 128.7, 128.6, 127.2, 127.1, 126.9, 60.4, 35.8, 30.5, 14.2.

3-(4-Biphenyl)propanoic acid (S47). The title compound was prepared from ethyl 3-(4-biphenyl)propanoate (S46) using the procedure described for 3-(4-phenoxyphenyl)propanoic acid (S30) to afford S47 (800 mg, 3.54 mmol, 95%) as a white solid: $^1H$ NMR ($CDCl_3$, 500 MHz) 7.59 (d, 2H, J=7.0 Hz), 7.55 (d, 2H, J=7.7 Hz), 7.45 (t, 2H, J=7.0 Hz), 7.35 (t, 1H, J=7.1 Hz), 7.30 (d, 2H, J=7.7 Hz), 3.03 (t, 2H, J=7.5 Hz), 2.75 (t, 2H, J=7.5 Hz); $^{13}C$ NMR ($CDCl_3$, 125 MHz) 179.2, 140.8, 139.3, 139.2, 128.7 (2C), 127.3, 127.1, 127.0, 35.5, 30.1.

1-Oxo-1-[5-(2-pyridyl)oxazol-2-yl]-3-(4-biphenyl)propane (11j). The title compound was prepared from 5-(2-pyridyl)oxazole (6) and 3-(4-biphenyl)propanoic acid (S47) using General Procedure B. Column chromatography ($SiO_2$, 3×7 cm, 10-30% EtOAc-hexanes gradient) afforded 11j (120 mg, 0.34 mmol, 56%) as a pale yellow solid: $^1H$ NMR ($CDCl_3$, 500 MHz) 8.68 (br s, 1H), 7.90 (s, 1H), 7.86 (d, 1H, J=7.7 Hz), 7.81 (t, 1H, J=7.7 Hz), 7.58 (d, 2H, J=7.7 Hz), 7.54 (d, 2H, J=8.1 Hz), 7.43 (t, 2H, J=7.7 Hz), 7.36 (d, 2H, J=8.4

Hz), 7.32-7.30 (m, 2H), 3.52 (t, 2H, J=7.4 Hz), 3.17 (t, 2H, J=7.4 Hz); $^{13}$C NMR (CDCl$_3$, 125 MHz) 187.3, 157.2, 153.3, 150.1, 146.2, 140.9, 139.4, 139.2, 137.1, 128.9, 128.7, 127.2, 127.1, 127.0, 126.9, 124.1, 120.4, 40.5, 29.3; IR (film) v$_{max}$ 3028, 2921, 1694, 1601, 1488, 1469, 1426, 1381, 1151, 1119, 1066, 990, 927, 831, 785, 762, 697 cm$^{-1}$; ESI-TOF m/z 355.1449 (C$_{23}$H$_{18}$N$_2$O$_2$+H$^+$ requires 355.1441).

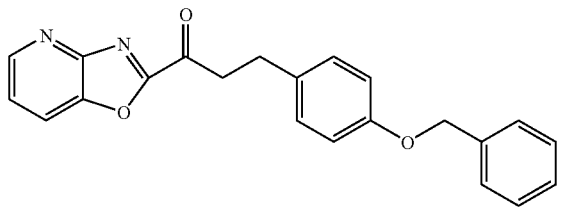 [SMILES: O=C(CCc1ccc(OCc2ccccc2)cc1)c1nc2ncccc2o1]

Example 11

3-(4-(Benzyloxy)phenyl)-1-(oxazolo[4,5-b]pyridin-2-yl)propan-1-one (11k)

3-(4-(Benzyloxy)phenyl)propan-1-ol (S48). A solution of 3-(4-(benzyloxy)-phenyl)propanoic acid (S22, 1.15 g, 4.50 mmol, 1 equiv) in anhydrous MeOH (16 mL) was treated with TMSCHN$_2$ (2.1 mL, 16.53 mmol, 3.7 equiv). After stirring at 25° C. for 16 h, the reaction mixture was concentrated to afford the corresponding methyl ester (1.15 g, 4.49 mmol, 95%). A solution of the ester (1.10 g, 4.30 mmol, 1 equiv) in anhydrous toluene (15 mL) at 0° C. was treated with DIBAL-H (1.5 M in toluene, 7.5 mL, 11.25 mmol, 2.6 equiv). After stirring for 45 min, the reaction mixture was quenched with MeOH and aqueous 1 N HCl and was extracted with CH$_2$Cl$_2$. The organic layer was dried over Na$_2$SO$_4$, filtered and concentrated. Column chromatography (SiO$_2$, 4×6 cm, 25% EtOAc-hexanes) afforded S48 (1.0 g, 4.39 mmol, 97%) as a white solid: $^1$H NMR (CDCl$_3$, 400 MHz) 7.45 (d, 2H, J=7.0 Hz), 7.40 (t, 2H, J=7.4 Hz), 7.35-7.32 (m, 1H), 7.13 (d, 2H, J=8.8 Hz), 6.92 (d, 2H, J=8.8 Hz), 5.06 (s, 2H), 3.68 (t, 2H, J=6.3 Hz), 2.67 (t, 2H, J=7.6 Hz), 1.90-1.85 (m, 2H); $^{13}$C NMR (CDCl$_3$, 100 MHz) 157.0, 137.1, 134.1, 129.3, 128.5, 127.9, 127.4, 114.7, 70.0, 62.2, 34.4, 31.1.

3-(4-(Benzyloxy)phenyl)propanal (S49). A solution of (COCl)$_2$ (0.5 mL, 5.82 mmol, 1.5 equiv) in anhydrous CH$_2$Cl$_2$ (11 mL) at −78° C. was treated with anhydrous DMSO (710 mg, 9.09 mmol, 2.3 equiv) in anhydrous CH$_2$Cl$_2$ (1.5 mL). After stirring for 10 min, a solution of 3-(4-(benzyloxy)phenyl)propan-1-ol (S48, 900 mg, 3.95 mmol, 1 equiv) in 4 mL of CH$_2$Cl$_2$ was added dropwise. After stirring for 1.5 h, Et$_3$N (3 mL) was added and the reaction mixture was allowed to warm at 25° C. The reaction was quenched with H$_2$O and extracted with CH$_2$Cl$_2$. The organic layer was washed with aqueous saturated NaCl, H$_2$O, dried over Na$_2$SO$_4$, filtered and concentrated. Column chromatography (SiO$_2$, 4×6.5 cm, 10% EtOAc-hexanes) afforded S49 (750 mg, 3.29 mmol, 84%) as a yellow solid: $^1$H NMR (CDCl$_3$, 600 MHz) 9.83 (s, 1H), 7.45 (d, 2H, J=7.0 Hz), 7.40 (t, 2H, J=7.4 Hz), 7.35-7.32 (m, 1H), 7.12 (d, 2H, J=8.4 Hz), 6.92 (d, 2H, J=8.4 Hz), 5.05 (s, 2H), 2.92 (d, 2H, J=7.4 Hz), 2.76 (d, 2H, J=7.4 Hz).

4-(4-(Benzyloxy)phenyl)-2-hydroxybutanenitrile (S50). A solution of 3-(4-(benzyloxy)phenyl)propanal (S49, 700 mg, 3.07 mmol, 1 equiv) in THF (13 mL) and H$_2$O (18 mL) was treated with KCN (2.30 g, 35.3 mmol, 11.5 equiv). After stirring for 50 h at 25° C., the reaction was quenched with H$_2$O and extracted with ether. The organic layer was washed with saturated aqueous NaCl, dried over Na$_2$SO$_4$, filtered and concentrated to afford S50 (755 mg, 2.96 mmol, 96%) as a white solid: $^1$H NMR (CDCl$_3$, 400 MHz) 7.47-7.33 (m, 5H), 7.14 (d, 2H, J=8.8 Hz), 6.95 (d, 2H, J=8.8 Hz), 5.06 (s, 2H), 4.39 (t, 1H, J=6.9 Hz), 2.82-2.77 (m, 2H), 2.17-2.10 (m, 2H); $^{13}$C NMR (CDCl$_3$, 100 MHz) 157.3, 136.9, 131.9, 129.4, 128.5, 127.9, 127.4, 119.9, 115.0, 70.0, 60.2, 36.6, 29.7; IR (film) v$_{max}$ 3444, 2927, 2865, 2250, 1611, 1583, 1514, 1454, 1382, 1246, 1177, 1079, 1024, 912, 830, 738, 695 cm$^{-1}$.

3-(4-(Benzyloxy)phenyl)-1-(oxazolo[4,5-b]pyridin-2-yl)propan-1-ol (S51). A mixture of anhydrous EtOH (3.6 mL) and CHCl$_3$ (4.0 mL) at 0° C. was treated with acetyl chloride (3.4 mL, 47.6 mmol, 16.2 equiv) and was stirred for 20 min. A solution of 4-(4-(benzyloxy)phenyl)-2-hydroxybutanenitrile (S50, 750 mg, 2.94 mmol, 1 equiv) in 9 mL of CHCl$_3$ was added dropwise and the reaction was stirred for 20 h at 25° C. The reaction mixture was concentrated and the crude product was dissolved in anhydrous EtOH. 2-Amino-3-hydroxypyridine (370 mg, 3.36 mmol, 1.1 equiv) was added and the reaction mixture was warmed at reflux overnight. Concentration followed by column chromatography (SiO$_2$, 2.5×8 cm, 0-4% MeOH—CHCl$_3$ gradient) afforded S51 (130 mg, 0.36 mmol, 13%) as a tan oil: $^1$H NMR (CDCl$_3$, 600 MHz) 8.52 (d, 1H, J=4.8 Hz), 7.78 (d, 1H, J=7.9 Hz), 7.43 (d, 2H, J=7.0 Hz), 7.39 (t, 2H, J=7.9 Hz), 7.34-7.31 (m, 1H), 7.28-7.26 (m, 1H), 7.14 (d, 2H, J=8.3 Hz), 6.87 (d, 2H, J=8.3 Hz), 5.07-5.00 (m, 1H), 5.00 (s, 2H), 2.84-2.81 (m, 2H), 2.36-2.30 (m, 2H); $^{13}$C NMR (CDCl$_3$, 150 MHz) 157.0, 154.6, 146.1, 143.0, 137.0, 133.0 (2C), 129.4, 128.5, 127.8, 127.4, 120.2, 118.8, 114.7, 69.9, 67.0, 36.9, 30.1; IR (film) v$_{max}$ 3380, 2926, 1665, 1612, 1557, 1511, 1454, 1410, 1382, 1239, 1177, 1092, 1026, 831, 785, 737, 700 cm$^{-1}$.

3-(4-(Benzyloxy)phenyl)-1-(oxazolo[4,5-b]pyridin-2-yl)propan-1-one (11k). A solution of 3-(4-(benzyloxy)phenyl)-1-(oxazolo[4,5-b]pyridin-2-yl)propan-1-ol (S51, 50 mg, 0.139 mmol, 1.0 equiv) in anhydrous CH$_2$Cl$_2$ (8 mL) at 0° C. was treated with Dess-Martin reagent (118 mg, 0.278 mmol, 2.1 equiv). The reaction mixture was allowed to warm at 25° C. and was stirred overnight. The reaction was quenched with aqueous saturated NaHCO$_3$ followed by saturated Na$_2$S$_2$O$_3$ and was extracted with CH$_2$Cl$_2$. The organic layer was dried over Na$_2$SO$_4$, filtered and concentrated. Column chromatography (SiO$_2$, 1.5×4 cm, 0-4% MeOH—CHCl$_3$ gradient) afforded S51 (24 mg, 0.067 mmol, 50%) as a pale yellow solid: $^1$H NMR (CDCl$_3$, 600 MHz) 8.76 (dd, 1H, J=4.9, 1.3 Hz), 8.00 (dd, 1H, J=8.3, 1.8 Hz), 7.50 (dd, 1H, J=8.3, 4.9 Hz), 7.43 (d, 2H, J=7.4 Hz), 7.38 (t, 2H, J=7.5 Hz), 7.32 (t, 1H, J=7.3 Hz), 7.20 (d, 2H, J=8.3 Hz), 6.92 (d, 2H, J=8.3 Hz), 5.04 (s, 3H), 3.60 (t, 2H, J=7.7 Hz), 2.62 (t, 2H, J=7.4 Hz); $^{13}$C NMR (CDCl$_3$, 150 MHz) 189.4, 158.4, 157.4, 154.1, 148.8, 143.6, 137.0, 132.3, 129.4, 128.5, 127.9, 127.4, 123.2, 120.3, 114.9, 70.0, 41.5, 28.7; IR (film) v$_{max}$ 2924, 2858, 1698, 1712, 1610, 1584, 1537, 1512, 1455, 1404, 1380, 1239, 1178, 1111, 1026, 990, 828, 786, 747 cm$^{-1}$; ESI-TOF m/z 359.1387 (C$_{28}$H$_{18}$N$_2$O$_3$+H$^+$ requires 359.1396).

The compounds in Examples 12-47 are prepared using methods analogous to those described in the preceding examples. The final preparation step and the physical and spectrographic characterization data for each example are provided.

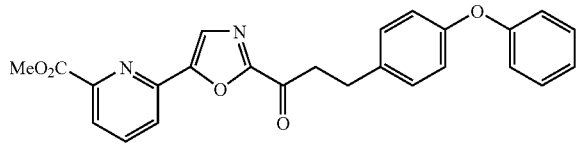 [SMILES: COC(=O)c1cccc(-c2cnc(C(=O)CCc3ccc(Oc4ccccc4)cc3)o2)n1]

Example 12

6-{2-[3-(4-Phenoxy-phenyl)-propionyl]-oxazol-5-yl}-pyridine-2-carboxylic acid methyl ester, i.e., Methyl 6-(2-(3-(4-phenoxyphenyl) propanoyl)oxazol-5-yl)pyridine-2-carboxylate (12)

Methyl 6-(2-(1-Hydroxy-3-(4-phenoxyphenyl)propyl)oxazol-5-yl)pyridine-2-carboxylate (779 mg, 1.81 mmol) was dissolved in anhydrous $CH_2Cl_2$ (26 mL) and Dess-Martin periodinane (1.151 g, 2.715 mmol) was added. The reaction solution was stirred at room temperature under an atmosphere of Ar for 90 min. The addition of saturated aqueous $NaHCO_3$ quenched the reaction and the organic layer was washed with saturated aqueous $Na_2S_2O_3$ then saturated aqueous NaCl. The organic layer was dried over $Na_2SO_4$ and the solvent was removed in vacuo. The crude product was purified by flash chromatography ($SiO_2$, 0-50% EtOAc/hexanes) to provide methyl 6-(2-(3-(4-phenoxyphenyl)propanoyl)oxazol-5-yl)pyridine-2-carboxylate as a yellow oil (711 mg, 92%): $^1$H NMR ($CDCl_3$, 500 MHz) δ 8.10 (d, 1H, J=7.5 Hz), 8.01-8.00 (m, 2H), 7.95 (t, 1H, J=7.5 Hz), 7.30 (t, 2H, J=7.5 Hz), 7.22 (d, 2H, J=8.5 Hz), 7.06 (t, 1H, J=7.0 Hz), 6.97 (d, 2H, J=7.5 Hz), 6.93 (d, 2H, J=8.5 Hz), 4.02 (s, 3H), 3.46 (t, 2H, J=7.5 Hz), 3.08 (t, 2H, J=7.5 Hz); $^{13}$C NMR ($CDCl_3$, 125 MHz) δ 187.2, 165.0, 157.4, 157.3, 155.5, 152.3, 148.5, 146.4, 138.2, 135.2, 129.7, 129.6, 127.9, 125.1, 123.2, 123.0, 119.1, 118.5, 53.0, 40.8, 28.9; HR ESI-TOF m/z 429.1444 (M+H$^+$, $C_{25}H_{20}N_2O_5$, requires 429.1445).

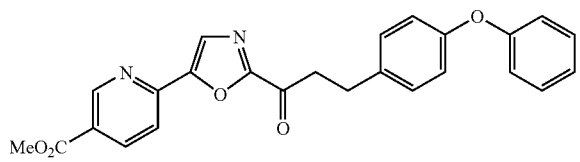 [SMILES: COC(=O)c1ccc(-c2cnc(C(=O)CCc3ccc(Oc4ccccc4)cc3)o2)nc1]

Example 13

6-{2-[3-(4-Phenoxy-phenyl)-propionyl]-oxazol-5-yl}-nicotinic acid methyl ester, i.e., Methyl 6-(2-(3-(4-Phenoxyphenyl)propanoyl)oxazol-5-yl)pyridine-3-carboxylate (13)

Methyl 6-(2-(1-Hydroxy-3-(4-phenoxyphenyl)propyl)oxazol-5-yl)pyridine-3-carboxylate (77 mg, 0.18 mmol) was dissolved in anhydrous $CH_2Cl_2$ (2.5 mL) and Dess-Martin periodinane (113 mg, 0.268 mmol) was added. The reaction solution was stirred at room temperature under an atmosphere of Ar for 90 min. The addition of saturated aqueous $NaHCO_3$ quenched the reaction and the organic layer was washed with saturated aqueous $Na_2S_2O_3$ then saturated aqueous NaCl. The organic layer was dried over $Na_2SO_4$ and the solvent was removed in vacuo. The crude product was purified by flash chromatography ($SiO_2$, 0-50% EtOAc/hexanes) to provide methyl 6-(2-(3-(4-phenoxyphenyl)propanoyl)oxazol-5-yl)pyridine-3-carboxylate as a white solid (63 mg, 82%): $^1$H NMR ($CDCl_3$, 500 MHz) δ 9.22 (d, 1H, J=1.0 Hz), 8.39 (dd, 1H, J=8.0, 2.0 Hz), 7.97 (s, 1H), 7.91 (d, 1H, J=8.0 Hz), 7.30 (t, 2H, J=7.5 Hz), 7.22 (d, 2H, J=8.5 Hz), 6.93 (d, 2H, J=8.5 Hz), 3.97 (s, 3H), 3.46 (t, 2H, J=7.0 Hz), 3.09 (t, 2H, J=7.0 Hz); $^{13}$C NMR ($CDCl_3$, 125 MHz) δ 187.2, 165.0, 157.6, 157.4, 155.5, 152.5, 151.2, 149.2, 138.2, 135.1, 129.7, 129.6, 128.7, 125.8, 123.0, 119.6, 119.1, 118.6, 52.6, 40.8, 28.9; HR ESI-TOF m/z 429.1440 (M+H$^+$, $C_{25}H_{20}N_2O_5$, requires 429.1445).

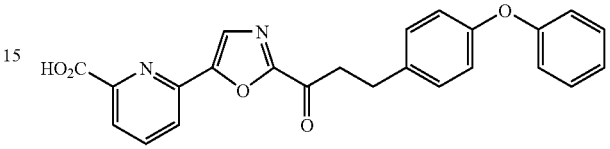

Example 14

6-{2-[3-(4-Phenoxy-phenyl)-propionyl]-oxazol-5-yl}-pyridine-2-carboxylic acid, i.e., 6-(2-(3-(4-Phenoxyphenyl)propanoyl)oxazol-5-yl)pyridine-2-carboxylic acid (14)

Methyl 6-(2-(3-(4-phenoxyphenyl)propanoyl)oxazol-5-yl)pyridine-2-carboxylate (356 mg, 0.831 mmol) was dissolved in THF/$H_2O$ (3:2, 75 mL) and LiOH (59 mg, 2.5 mmol) was added. The reaction solution was stirred at room temperature under an atmosphere of Ar for 2 h before the addition of 1 N HCl to adjust the solution to an acidic pH to quench the reaction. The reaction solution was diluted with EtOAc and the organic and aqueous layers were separated. The aqueous layer was extracted with EtOAc (3×). The organic phases were combined and washed with saturated aqueous NaCl, dried over $Na_2SO_4$, and concentrated in vacuo. The crude product was purified by flash chromatography ($SiO_2$, 1% AcOH/EtOAc) to provide 6-(2-(3-(4-phenoxyphenyl)propanoyl)oxazol-5-yl)pyridine-2-carboxylic acid as a light yellow solid (314 mg, 91%): $^1$H NMR (THF-$d_8$, 500 MHz) δ 8.11-8.03 (m, 4H), 7.30-7.25 (m, 4H), 7.03 (t, 1H, J=8.0 Hz), 6.94 (d, 2H, J=8 Hz), 6.91 (d, 2H, J=8.5 Hz), 3.43 (t, 2H, J=7.5 Hz), 3.04 (t, 2H, J=7.5 Hz); $^{13}$C NMR (THF-$d_8$, 500 MHz) δ 187.3, 165.7, 158.9, 156.7, 153.6, 150.1, 147.2, 139.7, 137.1, 130.7, 130.6, 128.7, 125.5, 123.8, 123.7, 120.0, 119.4, 41.7, 29.8; HR ESI-TOF m/z 415.1284 (M+H$^+$, $C_{24}H_{18}N_2O_5$, requires 415.1288).

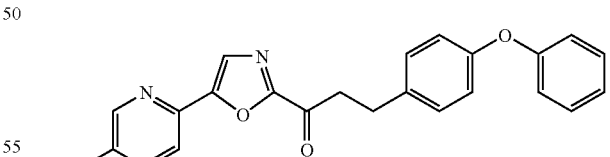

Example 15

6-{2-[3-(4-Phenoxy-phenyl)-propionyl]-oxazol-5-yl}-nicotinic acid, i.e., 6-(2-(3-(4-Phenoxyphenyl)propanoyl)oxazol-5-yl)pyridine-3-carboxylic acid (15)

Methyl 6-(2-(3-(4-phenoxyphenyl)propanoyl)oxazol-5-yl)pyridine-3-carboxylate (57 mg, 0.13 mmol) was dissolved in THF/H₂O (3:2, 7.5 mL) and LiOH (10 mg, 0.40 mmol) was added. The reaction solution was stirred at room temperature under an atmosphere of Ar for 2 h before the addition of 1 N HCl to adjust the solution to an acidic pH to quench the reaction. The reaction solution was diluted with EtOAc and the organic and aqueous layers were separated. The aqueous layer was extracted with EtOAc (3×). The organic phases were combined and washed with saturated aqueous NaCl, dried over Na₂SO₄, and concentrated in vacuo. The crude product was purified by flash chromatography (SiO₂, 1% AcOH/EtOAc) to provide 6-(2-(3-(4-phenoxyphenyl)propanoyl)oxazol-5-yl)pyridine-3-carboxylic acid as a light tan solid (31 mg, 56%): $^1$H NMR (THF-d₈, 600 MHz) δ 9.18 (s, 1H), 8.41 (dd, 1H, J=8.4, 1.8 Hz), 7.98 (s, 1H), 7.97 (d, 1H, J=8.4 Hz), 7.30-7.25 (m, 4H), 7.03 (t, 1H, J=7.8 Hz), 6.94 (d, 2H, J=7.8 Hz), 6.91 (d, 2H, J=8.4 Hz), 3.42 (t, 2H, J=7.8 Hz), 3.04 (t, 2H, J=7.8 Hz); $^{13}$C NMR (CDCl₃, 150 MHz) δ 187.3, 166.2, 159.7, 158.9, 156.7, 153.7, 152.4, 150.5, 139.4, 137.1, 130.7, 130.6, 129.3, 127.6, 123.8, 120.3, 120.0, 119.4, 41.7, 29.8; HR ESI-TOF m/z 415.1284 (M+H⁺, C₂₄H₁₈N₂O₅, requires 415.1288).

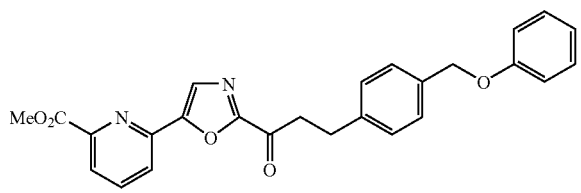 [SMILES: COC(=O)c1cccc(-c2cnc(C(=O)CCc3ccc(COc4ccccc4)cc3)o2)n1]

Example 16

6-{2-[3-(4-Phenoxymethyl-phenyl)-propionyl]-oxazol-5-yl}-pyridine-2-carboxylic acid methyl ester, i.e., Methyl 6-(2-(3-(4(Phenoxymethyl)phenyl)propanoyl)oxazol-5-yl)pyridine-2-carboxylate (16)

Methyl 6-(2-(1-hydroxy-3-(4-(phenoxymethyl)phenyl)propyl)oxazol-5-yl)pyridine-2-carboxylate (121 mg, 0.272 mmol) was dissolved in anhydrous CH₂Cl₂ (3 mL) and Dess-Martin periodinane (173 mg, 0.408 mmol) was added. The reaction solution was stirred at room temperature under an atmosphere of Ar for 2.5 h. The addition of saturated aqueous NaHCO₃ quenched the reaction and the organic layer was washed with saturated aqueous Na₂S₂O₃ then saturated aqueous NaCl. The organic layer was dried over Na₂SO₄ and the solvent was removed in vacuo. The crude product was purified by flash chromatography (SiO₂, 0-1% MeOH/CH₂Cl₂) to provide methyl 6-(2-(3-(4-(phenoxymethyl)phenyl)propanoyl)oxazol-5-yl)pyridine-2-carboxylate as a yellow oil (109 mg, 91%): $^1$H NMR (CDCl₃, 600 MHz) δ 8.10 (d, 1H, J=7.8 Hz), 8.00 (d, 2H, J=6.6 Hz), 7.95 (t, 1H, J=7.8 Hz), 7.36 (d, 2H, J=7.9 Hz), 7.29-7.27 (m, 4H), 6.97-6.93 (m, 3H), 5.02 (s, 2H), 4.02 (s, 3H), 3.47 (t, 2H, J=7.6 Hz), 3.11 (t, 2H, J=7.6 Hz); $^{13}$C NMR (CDCl₃, 150 MHz) δ 187.2, 165.0, 158.7, 157.9, 152.3, 148.4, 146.4, 140.0, 138.2, 135.0, 129.4, 128.6, 127.9, 127.7, 125.1, 123.2, 120.8, 114.7, 69.6, 53.0, 40.5, 29.3; HR ESI-TOF m/z 443.1606 (M+H⁺, C₂₆H₂₂N₂O₃, requires 443.1601).

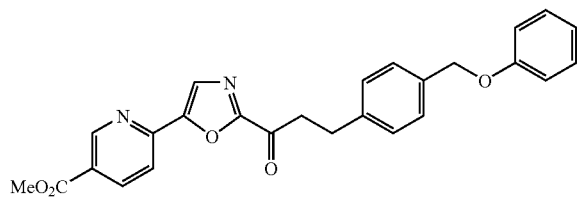 [SMILES: COC(=O)c1ccc(-c2cnc(C(=O)CCc3ccc(COc4ccccc4)cc3)o2)nc1]

Example 17

6-{2-3-(4-Phenoxymethyl-phenyl)-propionyl]-oxazol-5-yl}-nicotinic acid methyl ester, i.e., Methyl 6-(2-(3-(4-(Phenoxymethyl)phenyl) propanoyl)oxazol-5-yl)pyridine-3-carboxylate (17)

Methyl 6-(2-(1-hydroxy-3-(4-(phenoxymethyl)phenyl)propyl)oxazol-5-yl)pyridine-3-carboxylate (77 mg, 0.17 mmol) was dissolved in anhydrous CH₂Cl₂ (6 mL) and Dess-Martin periodinane (110 mg, 0.260 mmol) was added. The reaction solution was stirred at room temperature under an atmosphere of Ar for 2.5 h. The addition of saturated aqueous NaHCO₃ quenched the reaction and the organic layer was washed with saturated aqueous Na₂S₂O₃ and saturated aqueous NaCl. The organic layer was dried over Na₂SO₄ and the solvent was removed in vacuo. The crude product was purified by flash chromatography (SiO₂, 0-15% EtOAc/benzene) to provide methyl 6-(2-(3-(4-(phenoxymethyl)phenyl)propanoyl)oxazol-5-yl)pyridine-3-carboxylate as a white solid (60 mg, 78%): $^1$H NMR (CDCl₃, 600 MHz) δ 9.22 (dd, 1H, J=2.0, 0.7 Hz), 8.39 (dd, 1H, J=8.2, 2.1 Hz), 7.96 (s, 1H), 7.90 (d, 1H, J=8.2 Hz), 7.36 (d, 2H, J=8.0 Hz), 7.29-7.25 (m, 4H), 6.96-6.93 (m, 3H), 5.01 (s, 2H), 3.97 (s, 3H), 3.46 (t, 2H, J=7.6 Hz), 3.11 (t, 2H, J=7.6 Hz); 187.2, 165.0, 158.7, 157.6, 152.5, 151.2, 149.3, 140.0, 138.3, 135.1, 129.4, 128.7, 128.7, 127.8, 125.8, 120.8, 119.6, 114.8, 69.6, 52.6, 40.6, 29.3; HR ESI-TOF m/z 443.1600 (M+H⁺, C₂₆H₂₂N₂O₅, requires 443.1601).

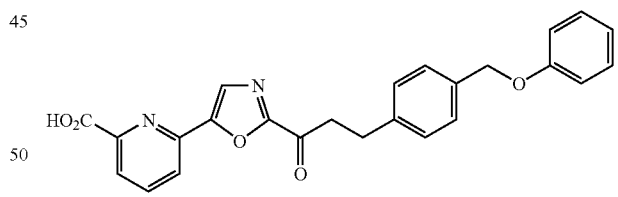

Example 18

6-{2-[3-(4-Phenoxymethyl-phenyl)-propionyl]-oxazol-5-yl}-pyridine-2-carboxylic acid, i.e., 6-(2-(3-(4-(Phenoxymethyl)phenyl) propanoyl)oxazol-5-yl) pyridine-2-carboxylic acid (18)

Methyl 6-(2-(3-(4-(phenoxymethyl)phenyl)propanoyl)oxazol-5-yl)pyridine-2-carboxylate (109 mg, 0.246 mmol) was dissolved in THF/H₂O (3:2, 15 mL) and LiOH (18 mg, 0.75 mmol) was added. The reaction solution was stirred at room temperature under an atmosphere of Ar for 15 min before the addition of 1 N HCl to adjust the solution to an acidic pH to quench the reaction. The reaction solution was diluted with EtOAc and the organic and aqueous layers were separated. The aqueous layer was extracted with EtOAc (3×). The organic phases were combined and washed with saturated aqueous NaCl, dried over Na₂SO₄, and concentrated in vacuo. The crude product was purified by tritration in ether to provide 6-(2-(3-(4-(phenoxymethyl)phenyl)propanoyl)oxazol-5-yl)pyridine-2-carboxylic acid as a pale yellow solid (85 mg, 81%): $^1$H NMR (THF-d$_8$, 600 MHz) δ 8.11-8.04 (m, 4H), 7.35 (d, 2H, J=7.9 Hz), 7.29 (d, 2H, J=7.9 Hz), 7.22 (dd, 2H, J=8.5, 7.5 Hz), 6.95 (d, 2H, J=7.8 Hz), 6.87 (t, 1H, J=7.3 Hz), 5.02 (s, 2H), 3.43 (t, 2H, J=7.6 Hz), 3.06 (t, 2H, J=7.6 Hz); $^{13}$C NMR (THF-d$_8$, 150 MHz) δ 187.1, 165.6, 160.1, 158.7, 153.4, 150.0, 147.0, 141.4, 139.6, 136.4, 130.0, 129.3, 128.6, 128.4, 125.3, 123.5, 121.3, 115.5, 70.2, 41.3, 30.0; HR ESI-TOF m/z 429.1444 (M+H$^+$, C$_{25}$H$_{20}$N$_2$O$_5$, requires 429.1445).

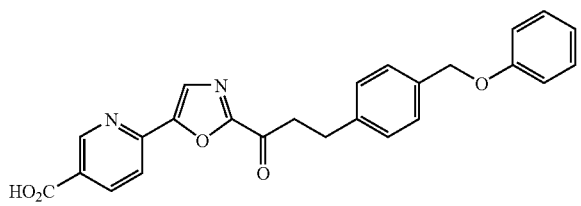 [SMILES: O=C(O)c1ccc(-c2cnc(C(=O)CCc3ccc(COc4ccccc4)cc3)o2)nc1]

Example 19

6-{2-[3-(4-Phenoxymethyl-phenyl)-propionyl]-oxazol-5-yl}-nicotinic acid, i.e, 6-(2-(3-(4-(Phenoxymethyl)phenyl)propanoyl)oxazol-5-yl)pyridine-3-carboxylic acid (19)

Methyl 6-(2-(3-(4-(phenoxymethyl)phenyl)propanoyl)oxazol-5-yl)pyridine-3-carboxylate (46 mg, 0.10 mmol) was dissolved in THF/H₂O (3:2, 10 mL) and LiOH (7 mg, 0.3 mmol) was added. The reaction solution was stirred at room temperature under an atmosphere of Ar for 15 min before the addition of 1 N HCl to adjust the solution to an acidic pH to quench the reaction. The reaction solution was diluted with EtOAc and the organic and aqueous layers were separated. The aqueous layer was extracted with EtOAc (3×). The organic phases were combined and washed with saturated aqueous NaCl, dried over Na₂SO₄, and concentrated in vacuo. The crude product was purified by tritration in ether to provide 6-(2-(3-(4-(phenoxymethyl)phenyl)propanoyl)oxazol-5-yl)pyridine-3-carboxylic acid as a white solid (35 mg, 79%): $^1$H NMR (THF-d$_8$, 600 MHz) δ 9.18 (d, 1H, J=1.3 Hz), 8.41 (dd, 1H, J=8.2, 2.0 Hz), 7.97 (s, 1H), 7.94 (d, 1H, J=8.2 Hz), 7.35 (d, 2H, J=7.9 Hz), 7.28 (d, 2H, J=7.8 Hz), 7.22 (t, 2H, J=8.0 Hz), 6.95 (d, 2H, J=8.1 Hz), 6.87 (t, 1H, J=7.3 Hz), 2.09 (s, 2H), 3.43 (t, 2H, J=7.6 Hz), 3.06 (t, 2H, J=7.6 Hz); $^{13}$C NMR (THF-d$_8$, 150 MHz) δ 187.1, 166.1, 160.1, 158.9, 153.5, 152.2, 150.3, 141.5, 139.2, 136.4, 130.0, 129.3, 129.1, 128.4, 127.5, 121.3, 120.1, 115.5, 70.6, 41.4, 30.1; HR ESI-TOF m/z 429.1443 (M+H$^+$, C$_{25}$H$_{20}$N$_2$O$_5$, requires 429.1445).

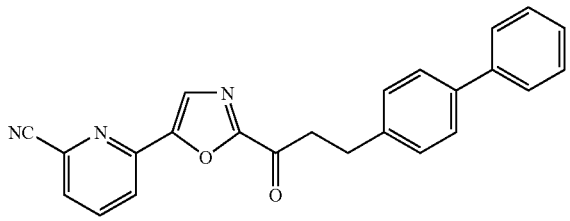

Example 20

6-[2-(3-Biphenyl-4-yl-propionyl)-oxazol-5-yl]-pyridine-2-carbonitrile, i.e., 2-Cyano-6-(2-(3-(biphenyl-4-yl)propanoyl)oxazol-5-yl)pyridine (20)

The title compound was prepared from 2-cyano-6-(2-(3-(biphenyl-4-yl)-1-(tert-butyldimethylsilyloxy)propyl)oxazol-5-yl)pyridine (87 mg, 0.176 mmol) following general procedure B. Flash chromatography (5-30% EtOAc/hexanes) yielded the title compound as a white solid (26 mg, 28%): $^1$H NMR (CDCl₃, 600 MHz) δ 8.03 (d, 1H, J=7.8 Hz), 7.97 (s, 1H), 7.95 (t, 1H, J=7.8 Hz), 7.67 (d, 1H, J=7.8 Hz), 7.56 (d, 2H, J=7.8 Hz), 7.52 (d, 2H, J=7.8 Hz), 7.42 (t, 2H, J=7.8 Hz), 7.35-7.32 (m, 3H), 3.51 (t, 2H, J=7.2 Hz), 3.15 (t, 2H, J=7.2 Hz); $^{13}$C NMR (CDCl₃, 150 MHz) δ 188.2, 158.4, 152.3, 148.7, 141.7, 140.2, 140.2, 139.3, 139.3, 135.1, 129.8, 129.6, 129.0, 128.2, 128.0, 127.8, 123.9, 117.4, 41.6, 30.1; HR ESI-TOF m/z 380.1391 (M+H$^+$, C$_{24}$H$_{18}$N$_3$O$_2$, requires 380.1393).

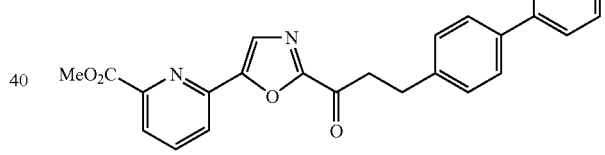

Example 21

6-[2-(3-Biphenyl-4-yl-propionyl)-oxazol-5-yl]-pyridine-2-carboxylic acid methyl ester, i.e., Methyl 6-(2-(3-(Biphenyl-4-yl)propanoyl)oxazol-5-yl)picolinate (21)

The title compound was prepared from methyl 6-(2-(3-(biphenyl-4-yl)-1-(tert-butyldimethylsilyloxy)propyl)oxazol-5-yl)picolinate (139 mg, 0.263 mmol) following general procedure B. Flash chromatography (10-40% EtOAc/hexanes) yielded the title compound as a white solid (37 mg, 75%): $^1$H NMR (CDCl₃, 600 MHz) δ 8.10 (d, 1H, J=7.5 Hz), 8.01-8.00 (m, 2H), 7.95 (t, 1H, J=7.5 Hz), 7.56 (d, 2H, J=7.8 Hz), 7.52 (d, 2H, J=7.8 Hz), 7.41 (t, 2H, J=7.8 Hz), 7.34-7.30 (m, 3H), 4.02 (s, 3H), 3.50 (t, 2H, J=7.2 Hz), 3.15 (t, 2H, J=7.2 Hz); $^{13}$C NMR (CDCl₃, 150 MHz) δ 188.2, 166.0, 158.2, 153.3, 149.4, 147.4, 141.8, 140.3, 140.1, 139.2, 129.8, 129.6, 128.9, 128.1, 128.0, 127.9, 126.1, 124.2, 54.0, 41.5, 30.1; HR ESI-TOF m/z 413.1491 (M+H$^+$, C$_{25}$H$_{21}$N$_2$O$_4$, requires 413.1496).

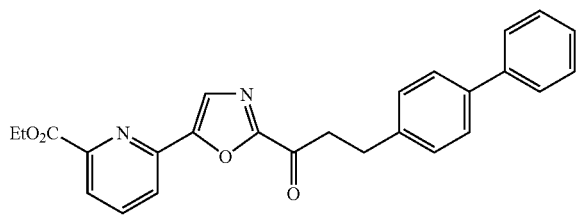 [SMILES: CCOC(=O)c1cccc(-c2cnc(C(=O)CCc3ccc(-c4ccccc4)cc3)o2)n1]

Example 22

6-[2-(3-Biphenyl-4-yl-propionyl)-oxazol-5-yl]-pyridine-2-carboxylic acid ethyl ester, i.e., Ethyl 6-(2-(3-(biphenyl-4-yl)propanoyl)oxazol-5-yl)pyridine-2-carboxylate (22)

The title compound was prepared from ethyl 6-(2-(3-(biphenyl-4-yl)-1-(tert-butyldimethylsilyloxy)propyl)oxazol-5-yl)pyridine-2-carboxylate (126 mg, 0.232 mmol) following general procedure B. Flash chromatography (10-40% EtOAc/hexanes) yielded the title compound as a white solid (71 mg, 75%): $^1$H NMR (CDCl$_3$, 600 MHz) δ 8.10 (d, 1H, J=7.8 Hz), 8.02 (s, 1H), 8.00 (d, 1H, J=7.8 Hz), 7.94 (t, 1H, J=7.5 Hz), 7.56 (d, 2H, J=7.8 Hz), 7.52 (d, 2H, J=7.8 Hz), 7.41 (t, 2H, J=7.8 Hz), 7.35-7.31 (m, 3H), 4.50 (q, 2H, J=7.2 Hz), 3.51 (t, 2H, J=7.2 Hz), 3.15 (t, 2H, J=7.2 Hz), 1.46 (t, 3H, J=7.2 Hz); $^{13}$C NMR (CDCl$_3$, 150 MHz) δ 188.2, 165.4, 158.2, 153.4, 149.7, 147.4, 141.8, 140.3, 140.1, 139.1, 129.8, 129.6, 128.9, 128.1, 128.0, 127.9, 126.0, 124.0, 63.1, 41.5, 30.2, 15.2; HR ESI-TOF m/z 427.1652 (M+H$^+$, C$_{26}$H$_{23}$N$_2$O$_4$, requires 427.1652).

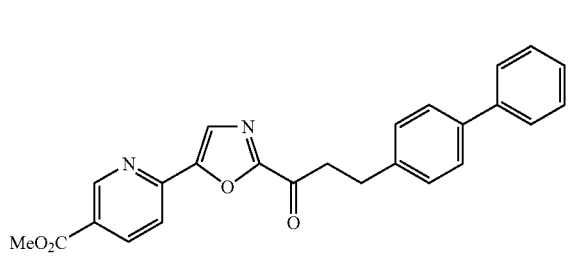 [SMILES: COC(=O)c1ccc(-c2cnc(C(=O)CCc3ccc(-c4ccccc4)cc3)o2)nc1]

Example 23

6-[2-(3-Biphenyl-4-yl-propionyl)-oxazol-5-yl]-nicotinic acid methyl ester, i.e., Methyl 6-(2-(3-(biphenyl-4-yl)propanoyl)oxazol-5-yl)pyridine-3-carboxylate (23)

The title compound was prepared from methyl 6-(2-(3-(biphenyl-4-yl)-1-(tert-butyldimethylsilyloxy)propyl)oxazol-5-yl)nicotinate (124 mg, 0.235 mmol) following general procedure B. Flash chromatography (10-80% EtOAc/hexanes) yielded the title compound as a white solid (37 mg, 49%): $^1$H NMR (CDCl$_3$, 600 MHz) δ 9.23 (d, 1H, J=1.5 Hz), 8.40 (dd, 1H, J=2.2, 8.5 Hz), 7.97 (s, 1H), 7.92 (d, 1H, J=8.5 Hz), 7.56 (d, 2H, J=8.0 Hz), 7.53 (d, 2H, J=7.8 Hz), 7.42 (t, 2H, J=7.8 Hz), 7.35-7.32 (m, 3H), 3.98 (s, 3H), 3.51 (t, 2H, J=7.2 Hz), 3.15 (t, 2H, J=7.2 Hz); $^{13}$C NMR (CDCl$_3$, 150 MHz) δ 188.2, 165.9, 158.5, 153.4, 152.2, 150.2, 141.8, 140.2, 139.2, 139.2, 129.8, 129.6, 129.6, 128.2, 128.0, 127.9, 126.7, 120.5, 53.5, 41.6, 30.2; HR ESI-TOF m/z 413.1493 (M+H$^+$, C$_{25}$H$_{21}$N$_2$O$_4$, requires 413.1496).

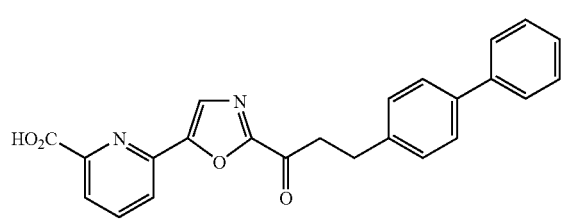 [SMILES: O=C(O)c1cccc(-c2cnc(C(=O)CCc3ccc(-c4ccccc4)cc3)o2)n1]

Example 24

6-[2-(3-Biphenyl-4-yl-propionyl)-oxazol-5-yl]-pyridine-2-carboxylic acid; i.e., 6-(2-(3-(Biphenyl-4-yl)propanoyl)oxazol-5-yl)picolinic acid (24)

The title compound was prepared from methyl 6-(2-(3-(biphenyl-4-yl)propanoyl)oxazol-5-yl)picolinate (15 mg, 0.036 mmol) following general procedure C. Flash chromatography (0-2% AcOH/EtOAc) yielded the title compound as a white solid (10 mg, 71%): $^1$H NMR (THF-d$_8$, 600 MHz) δ 8.12-8.06 (m, 4H), 7.60 (d, 2H, J=7.8 Hz), 7.55 (d, 2H, J=7.8 Hz), 7.40-7.36 (m, 4H), 7.28 (t, 1H, J=7.8 Hz), 3.47 (t, 2H, J=7.2 Hz), 3.10 (t, 2H, J=7.2 Hz); $^{13}$C NMR (THF-d$_8$, 150 MHz) δ 187.0, 165.4, 158.6, 153.3, 149.8, 146.9, 141.8, 141.0, 139.8, 139.5, 129.6, 129.3, 128.4, 127.6, 127.4, 125.2, 123.4, 41.2, 29.9; HR ESI-TOF m/z 399.1334 (M+H$^+$, C$_{24}$H$_{19}$N$_2$O$_4$, requires 399.1339).

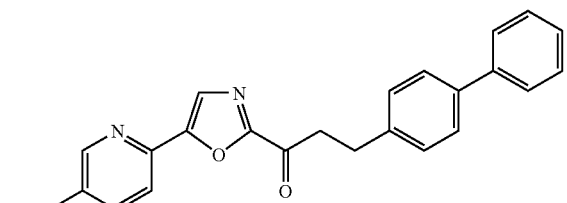

Example 25

6-[2-(3-Biphenyl-4-yl-propionyl)-oxazol-5-yl]-nicotinic acid, i.e., 6-(2-(3-(Biphenyl-4-yl)propanoyl)oxazol-5-yl)pyridine-3-carboxylic acid (25)

The title compound was prepared from methyl 6-(2-(3-(biphenyl-4-yl)propanoyl)oxazol-5-yl)pyridine-3-carboxylate (11 mg, 0.027 mmol) following general procedure C. Flash chromatography (0-2% AcOH/EtOAc) yielded the title compound as a white solid (7 mg, 66%): $^1$H NMR (THF-d$_8$, 600 MHz) δ 9.18 (s, 1H), 8.42 (d, 2H, J=7.8 Hz), 7.99-7.95 (m, 2H), 7.60 (d, 2H, J=7.8 Hz), 7.55 (d, 2H, J=7.8 Hz), 7.40-7.35 (m, 4H), 7.27 (t, 1H, J=7.8 Hz), 3.47 (t, 2H, J=7.2 Hz), 3.10 (t, 2H, J=7.2 Hz); $^{13}$C NMR (THF-d$_8$, 150 MHz) δ 187.0, 165.9, 158.9, 153.4, 152.1, 150.2, 141.8, 140.9, 139.8, 139.1, 129.6, 129.3, 129.3, 129.1, 127.6, 127.4, 127.3, 120.0, 41.3, 30.5; HR ESI-TOF m/z 399.1333 (M+H$^+$, C$_{24}$H$_{19}$N$_2$O$_4$, requires 399.1339).

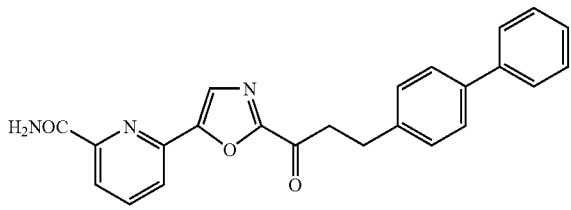 [SMILES: NC(=O)c1cccc(-c2cnc(C(=O)CCc3ccc(-c4ccccc4)cc3)o2)n1]

Example 26

6-[2-(3-Biphenyl-4-yl-propionyl)-oxazol-5-yl]-pyridine-2-carboxylic acid amide, i.e., 6-(2-(3-(Biphenyl-4-yl)propanoyl)oxazol-5-yl)pyridine-2-carboxamide (26)

The title compound was prepared from 6-(2-(3-(biphenyl-4-yl)-1-(tert-butyldimethylsilyloxy)propyl)oxazol-5-yl)pyridine-2-carboxamide (73 mg, 0.142 mmol) following general procedure B. Flash chromatography (20-60% EtOAc/hexanes) yielded the title compound as a white solid (19 mg, 39%): $^1$H NMR (DMSO-$d_6$, 600 MHz) δ 8.42 (s, 1H), 8.37 (br s, 1H), 8.13 (t, 1H, J=7.5 Hz), 8.04 (d, 1H, J=7.5 Hz), 7.99 (d, 1H, J=7.5 Hz), 7.80 (br s, 1H), 7.61 (d, 2H, J=7.8 Hz), 7.57 (d, 2H, J=7.8 Hz), 7.42 (t, 2H, J=7.8 Hz), 7.36-7.31 (m, 3H), 3.47 (t, 2H, J=7.2 Hz), 3.02 (t, 2H, J=7.2 Hz); $^{13}$C NMR (DMSO-$d_6$, 150 MHz) δ 186.9, 165.1, 157.1, 151.9, 150.4, 144.3, 140.0, 139.8, 139.4, 137.9, 128.9, 128.8, 128.8, 128.3, 127.1, 126.6, 126.4, 122.0, 40.0, 28.4; HR ESI-TOF m/z 398.1494 (M+H$^+$, $C_{24}H_{20}N_3O_3$, requires 398.1499).

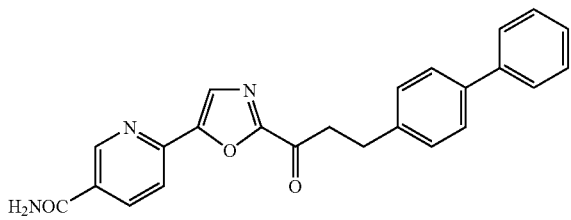

Example 27

6-[2-(3-Biphenyl-4-yl-propionyl)-oxazol-5-yl]-nicotinamide, i.e., 6-(2-(3-(Biphenyl-4-yl)propanoyl)oxazol-5-yl)pyridine-3-carboxamide (27)

The title compound was prepared from 6-(2-(3-(biphenyl-4-yl)-1-(tert-butyldimethylsilyloxy)propyl)oxazol-5-yl)pyridine-3-carboxamide (96 mg, 0.187 mmol) following general procedure B. Flash chromatography (20-90% EtOAc/hexanes) yielded the title compound as a white solid (8 mg, 17%): $^1$H NMR (CDCl$_3$, 600 MHz) δ 9.21 (d, 1H, J=1.5 Hz), 8.31 (dd, 1H, J=2.2, 8.5 Hz), 7.97-7.95 (m, 2H), 7.55 (d, 2H, J=8.0 Hz), 7.53 (d, 2H, J=7.8 Hz), 7.38 (t, 2H, J=7.8 Hz), 7.30-7.26 (m, 3H), 3.47 (t, 2H, J=7.2 Hz), 3.10 (t, 2H, J=7.2 Hz); $^{13}$C NMR (CDCl$_3$, 150 MHz) δ 187.0, 166.3, 158.7, 153.6, 150.3, 149.0, 141.9, 140.2, 139.2, 139.2, 129.8, 129.6, 128.2, 128.0, 127.9, 126.7, 120.5, 41.2, 30.5; HR ESI-TOF m/z 398.1492 (M+H$^+$, $C_{24}H_{20}N_3O_3$, requires 398.1499).

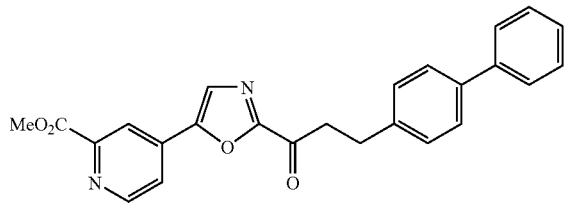 [SMILES: COC(=O)c1cc(-c2cnc(C(=O)CCc3ccc(-c4ccccc4)cc3)o2)ccn1]

Example 28

4-[2-(3-Biphenyl-4-yl-propionyl)-oxazol-5-yl]-pyridine-2-carboxylic acid methyl ester, i.e., Methyl 4-(2-(3-(Biphenyl-4-yl)propanoyl)oxazol-5-yl)pyridine-2-carboxylate (28)

The title compound was prepared from methyl 4-(2-(3-(biphenyl-4-yl)-1-(tert-butyldimethylsilyloxy)propyl)oxazol-5-yl)pyridine-2-carboxylate (66 mg, 0.125 mmol) following general procedure B. Flash chromatography (20-80% EtOAc/hexanes) yielded the title compound as a white solid (46 mg, 88%): $^1$H NMR (DMSO-$d_6$, 600 MHz) δ 8.83 (d, 1H, J=5.4 Hz), 8.41 (s, 1H), 8.37 (m, 1H), 8.03 (dd, 1H, J=1.8, 4.8 Hz), 7.61 (d, 2H, J=7.8 Hz), 7.58 (d, 2H, J=7.8 Hz), 7.42 (t, 2H, J=7.8 Hz), 7.36-7.30 (m, 3H), 3.46 (t, 2H, J=7.2 Hz), 3.02 (t, 2H, J=7.2 Hz); $^{13}$C NMR (DMSO-$d_6$, 150 MHz) δ 188.4, 166.1, 158.9, 152.3, 151.1, 149.9, 141.3, 141.2, 139.3, 136.0, 130.3, 130.2, 130.1, 128.5, 128.0, 127.8, 123.2, 120.9, 54.0, 31.7, 29.8; HR ESI-TOF m/z 413.1493 (M+H$^+$, $C_{25}H_{21}N_2O_4$, requires 413.1496).

![](pyridine-carboxylic acid structure)

Example 29

4-[2-(3-Biphenyl-4-yl-propionyl)-oxazol-5-yl]-pyridine-2-carboxylic acid, i.e., 4-(2-(3-(Biphenyl-4-yl)propanoyl)oxazol-5-yl)pyridine-2-carboxylic acid (29)

The title compound was prepared from methyl 4-(2-(3-(biphenyl-4-yl)propanoyl)oxazol-5-yl)pyridine-2-carboxylate (20 mg, 0.048 mmol) following general procedure C. Preparative thin layer chromatography (10% MeOH/CH$_2$Cl$_2$) yielded the title compound as a white solid (13 mg, 68%): $^1$H NMR (DMSO-$d_6$, 600 MHz) δ 8.83 (d, 1H, J=5.4 Hz), 8.43-8.41 (m, 2H), 8.04 (dd, 1H, J=1.8, 4.8 Hz), 7.60 (d, 2H, J=7.8 Hz), 7.56 (d, 2H, J=7.8 Hz), 7.41 (t, 2H, J=7.8 Hz), 7.35-7.30 (m, 3H), 3.45 (t, 2H, J=7.2 Hz), 3.01 (t, 2H, J=7.2 Hz); HR ESI-TOF m/z 399.1335 (M+H$^+$, $C_{24}H_{19}N_2O_4$, requires 399.1339).

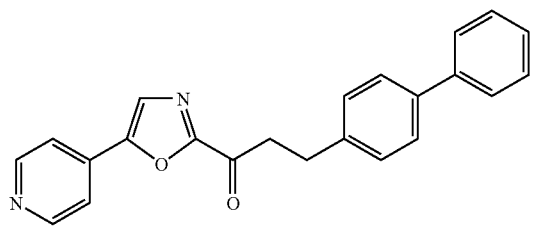 [SMILES: O=C(CCc1ccc(-c2ccccc2)cc1)c1ncc(-c2ccncc2)o1]

Example 30

3-Biphenyl-4-yl-1-(5-pyridin-4-yl-oxazol-2-yl)-propan-1-one, i.e., 3-(Biphenyl-4-yl)-1-(5-(pyridin-4-yl)oxazol-2-yl)propan-1-one (30)

The title compound was prepared from 2-(3-(biphenyl-4-yl)-1-(tert-butyldimethylsilyloxy)propyl)-5-(pyridin-4-yl)oxazole (49 mg, 0.104 mmol) following general procedure B. Flash chromatography (20-60% EtOAc/hexanes) yielded the title compound as a white solid (22 mg, 68%): $^1$H NMR (CDCl$_3$, 600 MHz) δ 8.72-8.71 (m, 2H), 7.68 (s, 1H), 7.61 (d, 2H, J=7.8 Hz), 7.56 (d, 2H, J=7.8 Hz), 7.52 (d, 2H, J=7.8 Hz), 7.42 (t, 2H, J=7.8 Hz), 7.35-7.32 (m, 2H), 3.48 (t, 2H, J=7.2 Hz), 3.14 (t, 2H, J=7.2 Hz); $^{13}$C NMR (CDCl$_3$, 150 MHz) δ 188.0, 158.6, 152.4, 151.6, 151.6, 141.7, 140.2, 134.5, 129.8, 129.6, 128.2, 128.0, 127.9, 127.5, 119.8, 41.5, 30.1; HR ESI-TOF m/z 355.1438 (M+H$^+$, C$_{23}$H$_{19}$N$_2$O$_2$, requires 355.1441).

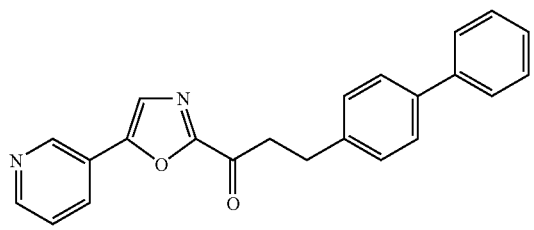 [SMILES: O=C(CCc1ccc(-c2ccccc2)cc1)c1ncc(-c2cccnc2)o1]

Example 31

3-Biphenyl-4-yl-1-(5-pyridin-3-yl-oxazol-2-yl)-propan-1-one, i.e., 3-(Biphenyl-4-yl)-1-(5-(pyridin-3-yl)oxazol-2-yl)propan-1-one (31)

The title compound was prepared from 2-(3-(biphenyl-4-yl)-1-(tert-butyldimethylsilyloxy)propyl)-5-(pyridin-3-yl)oxazole (42 mg, 0.089 mmol) following general procedure B. Flash chromatography (20-60% EtOAc/hexanes) yielded the title compound as a white solid (21 mg, 74%): $^1$H NMR (CDCl$_3$, 600 MHz) δ 9.02 (s, 1H), 8.65 (s, 1H), 8.05 (d, 1H, J=7.8 Hz), 7.60 (s, 1H), 7.56 (d, 2H, J=7.8 Hz), 7.52 (d, 2H, J=7.8 Hz), 7.43-7.39 (m, 2H), 7.35-7.31 (m, 3H), 3.48 (t, 2H, J=7.2 Hz), 3.15 (t, 2H, J=7.2 Hz); $^{13}$C NMR (CDCl$_3$, 150 MHz) δ 188.0, 158.4, 152.3, 151.6, 147.4, 141.8, 140.3, 140.2, 133.3, 129.8, 129.6, 128.1, 128.0, 127.9, 125.7, 124.7, 124.0, 41.4, 30.2; HR ESI-TOF m/z 355.1444 (M+H$^+$, C$_{23}$H$_{19}$N$_2$O$_2$, requires 355.1441).

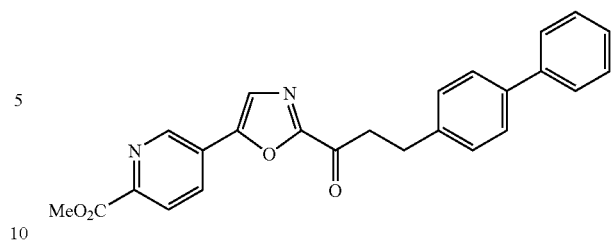

Example 32

5-[2-(3-Biphenyl-4-yl-propionyl)-oxazol-5-yl]pyridine-2-carboxylic acid methyl ester, i.e., Methyl 5-(2-(3-(Biphenyl-4-yl)propanoyl)oxazol-5-yl)pyridine-2-carboxylate (32)

The title compound was prepared from methyl 5-(2-(3-(biphenyl-4-yl)-1-(tert-butyldimethylsilyloxy)propyl)oxazol-5-yl)pyridine-2-carboxylate (49 mg, 0.093 mmol) following general procedure B. Flash chromatography (20-100% EtOAc/hexanes) yielded the title compound as a white solid (10 mg, 30%): $^1$H NMR (THF-d$_8$, 600 MHz) δ 9.13 (d, 1H, J=1.8 Hz), 8.30 (dd, 1H, J=1.8, 4.8 Hz), 8.16 (d, 1H, J=7.8 Hz), 7.68 (d, 2H, J=7.8 Hz), 7.54-7.52 (m, 3H), 7.39 (t, 2H, J=7.8 Hz), 7.37-7.30 (m, 3H), 4.94 (t, 1H, J=6.0 Hz), 3.45 (t, 2H, J=7.8 Hz), 3.09 (t, 2H, J=7.8 Hz); $^{13}$C NMR (THF-d$_8$, 150 MHz) δ 185.0, 166.0, 163.8, 147.5, 146.8, 145.0, 140.0, 139.8, 137.7, 132.8, 130.8, 130.8, 127.8, 127.4, 127.1, 127.1, 125.7, 125.5, 50.4, 39.3, 35.9; HR ESI-TOF m/z 413.1493 (M+H$^+$, C$_{25}$H$_{21}$N$_2$O$_4$, requires 413.1496).

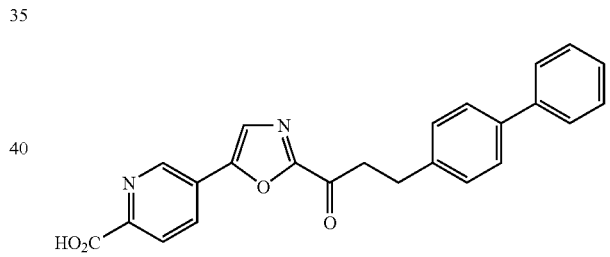

Example 33

5-[2-(3-Biphenyl-4-yl-propionyl)-oxazol-5-yl]-pyridine-2-carboxylic acid, i.e., 5-(2-(3-(Biphenyl-4-yl)propanoyl)oxazol-5-yl)pyridine-2-carboxylic acid (33)

The title compound was prepared from methyl 5-(2-(3-(biphenyl-4-yl)propanoyl)oxazol-5-yl)pyridine-2-carboxylate (5 mg, 0.012 mmol) following general procedure C. Preparative thin layer chromatography (20% MeOH/CH$_2$Cl$_2$) yielded the title compound as a white solid (3 mg, 75%): $^1$H NMR (THF-d$_8$, 600 MHz) δ 9.11 (d, 1H, J=1.8 Hz), 8.21 (dd, 1H, J=1.8, 4.8 Hz), 8.04 (d, 1H, J=7.8 Hz), 7.54 (d, 2H, J=7.8 Hz), 7.53-7.51 (m, 3H), 7.40 (t, 2H, J=7.8 Hz), 7.35-7.31 (m, 3H), 3.45 (t, 2H, J=7.8 Hz), 3.09 (t, 2H, J=7.8 Hz); $^{13}$C NMR (THF-d$_8$, 150 MHz) δ 185.2, 167.5, 162.1, 147.3, 146.1, 145.0, 140.3, 139.5, 137.2, 131.6, 131.0, 130.8, 127.8, 127.4, 127.1, 127.1, 126.1, 125.9, 39.3, 35.9; HR ESI-TOF m/z 399.1335 (M+H$^+$, C$_{24}$H$_{19}$N$_2$O$_4$, requires 399.1339).

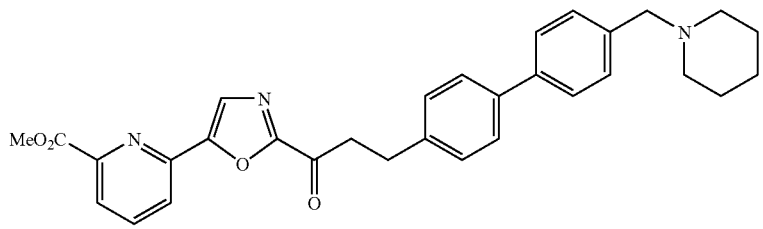 [SMILES: COC(=O)c1cccc(-c2cnc(C(=O)CCc3ccc(-c4ccc(CN5CCCCC5)cc4)cc3)o2)n1]

Example 34

6-{2-[3-(4'-Piperidin-1-ylmethyl-biphenyl-4-yl)-propionyl]-oxazol-5-yl}-pyridine-2-carboxylic acid methyl ester, i.e., Methyl 6-(2-(3-(4'-(Piperidin-1-ylmethyl)biphenyl-4-yl)propanoyl)oxazol-5-yl)pyridine-2-carboxylate (34)

Methyl 6-(2-(3-(4'-formylbiphenyl-4-yl)propanoyl)oxazol-5-yl)pyridine-2-carboxylate (19 mg, 0.043 mmol) and piperidine (0.007 mL, 0.07 mmol) were dissolved in dichloroethane (2 mL) and NaBH(OAc)$_3$ (18 mg, 0.086 mmol) was added. The reaction solution was stirred under an atmosphere of Ar at ambient temperature for 1 h and then quenched with saturated aqueous NaHCO$_3$. The crude product was extracted with EtOAc and the solvent was removed in vacuo. The crude product was purified by flash chromatography (SiO$_2$, 5% MeOH/EtOAc) to furnish methyl 6-(2-(3-(4'-(piperidin-1-ylmethyl)biphenyl-4-yl)propanoyl)oxazol-5-yl)pyridine-2-carboxylate as a clear pale yellow oil (14 mg, 64%): $^1$H NMR (CDCl$_3$, 600 MHz) δ 8.11 (d, 1H, J=7.7 Hz), 8.02 (d, 2H, J=9.0 Hz), 7.97 (t, 1H, J=7.8 Hz), 7.52 (dd, 4H, J=7.9, 6.4 Hz), 7.37 (d, 2H, J=7.9 Hz), 7.33 (d, 2H, J=7.8 Hz), 4.03 (s, 3H), 3.52-3.50 (m, 4H), 3.15 (t, 2H, J=7.6 Hz), 2.42 (bs, 4H), 1.61-1.58 (m, 4H), 1.44 (bs, 2H); $^{13}$C NMR (CDCl$_3$, 150 MHz) δ 187.3, 165.1, 157.4, 152.4, 148.5, 146.5, 139.5, 139.2, 139.1, 138.3, 129.7, 128.8, 128.0, 127.1, 126.7, 125.2, 123.3, 63.4, 54.4, 53.1, 40.6, 29.3, 25.9, 24.3; HR ESI-TOF m/z 510.2385 (M+H$^+$, C$_{31}$H$_{31}$N$_3$O$_4$, requires 510.2387).

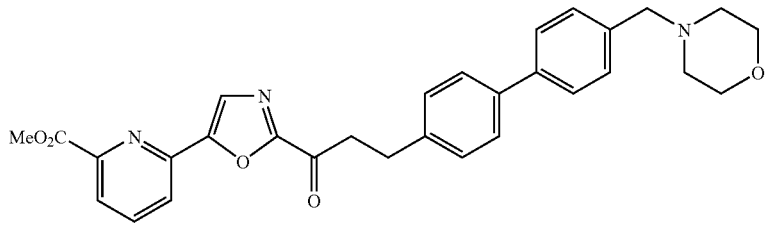 [SMILES: COC(=O)c1cccc(-c2cnc(C(=O)CCc3ccc(-c4ccc(CN5CCOCC5)cc4)cc3)o2)n1]

Example 35

6-{2-[3-(4'-Morpholin-4-ylmethyl-biphenyl-4-yl)-propionyl]-oxazol-5-yl}-pyridine-2-carboxylic acid methyl ester, i.e., Methyl 6-(2-(3-(4'-(Morpholinomethyl)biphenyl-4-yl)propanoyl)oxazol-5-yl)pyridine-2-carboxylate (35)

Methyl 6-(2-(3-(4'-formylbiphenyl-4-yl)propanoyl)oxazol-5-yl)pyridine-2-carboxylate (31 mg, 0.070 mmol) and morpholine (0.012 mL, 1.4 mmol) were dissolved in dichloroethane (2 mL) and NaBH(OAc)$_3$ (31 mg, 15 mmol) was added. The reaction solution was stirred under an atmosphere of Ar at ambient temperature for 7 h and then quenched with saturated aqueous NaHCO$_3$. The crude product was extracted with EtOAc and the solvent was removed in vacuo. The crude product was purified by flash chromatography (SiO$_2$, 50-100% EtOAc/hexanes) to furnish methyl 6-(2-(3-(4'-(morpholinomethyl)biphenyl-4-yl)propanoyl)oxazol-5-yl)pyridine-2-carboxylate as a light yellow oil (21 mg, 58%): $^1$H NMR (CDCl$_3$, 600 MHz) δ 8.12 (d, 1H, J=7.7 Hz), 8.04-8.02 (m, 2H), 7.97 (t, 1H, J=7.8 Hz), 7.52 (d, 4H, J=8.0 Hz), 7.38 (d, 2H, J=8.0 Hz), 7.34 (d, 2H, J=8.0 Hz), 4.04 (s, 3H), 3.73 (t, 4H, J=4.5 Hz), 3.54 (s, 2H), 3.51 (t, 2H, J=7.6 Hz), 3.16 (t, 2H, J=7.6 Hz), 2.48 (s, 4H); $^{13}$C NMR (CDCl$_3$, 150 MHz) δ 187.3, 165.1, 157.4, 152.4, 148.5, 146.5, 139.8, 139.3, 139.0, 138.2, 136.7, 129.6, 128.9, 128.0, 127.1, 126.8, 125.2, 123.3, 67.0, 63.1, 53.6, 53.1, 40.6, 29.3; HR ESI-TOF m/z 512.2173 (M+H$^+$, C$_{30}$H$_{29}$N$_3$O$_5$, requires 512.2180).

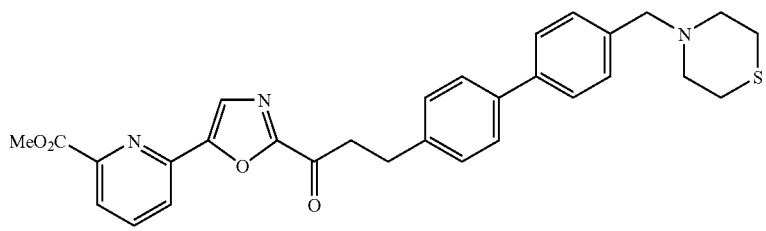 [SMILES: COC(=O)c1cccc(-c2cnc(C(=O)CCc3ccc(-c4ccc(CN5CCSCC5)cc4)cc3)o2)n1]

Example 36

6-{2-[3-(4'-Thiomorpholin-4-ylmethyl-biphenyl-4-yl)-propionyl]-oxazol-5-yl}-pyridine-2-carboxylic acid methyl ester, i.e., Methyl 6-(2-(3-(4'-(Thiomorpholinomethyl)biphenyl-4-yl)propanoyl)oxazol-5-yl)pyridine-2-carboxylate (36)

Methyl 6-(2-(3-(4'-formylbiphenyl-4-yl)propanoyl)oxazol-5-yl)pyridine-2-carboxylate (124 mg, 0.282 mmol) and thiomorpholine (0.040 mL, 0.42 mmol) were dissolved in dichloroethane (12 mL) and NaBH(OAc)$_3$ (179 mg, 0.845 mmol) was added. The reaction solution was stirred under an atmosphere of Ar at ambient temperature for 3.5 h and then quenched with saturated aqueous NaHCO$_3$. The crude product was extracted with EtOAc and the solvent was removed in vacuo. The crude product was purified by flash chromatography (SiO$_2$, 50-90% EtOAc/hexanes) to furnish methyl 6-(2-(3-(4'-(thiomorpholinomethyl)biphenyl-4-yl)propanoyl)oxazol-5-yl)pyridine-2-carboxylate as a pale tan solid (90 mg, 61%): $^1$H NMR (CDCl$_3$, 600 MHz) δ 8.12 (d, 1H, J=7.7 Hz), 8.04-8.02 (m, 2H), 7.97 (t, 1H, J=7.8 Hz), 7.52 (dd, 4H, J=8.2, 1.8 Hz), 7.35 (t, 4H, J=8.6 Hz), 4.03 (s, 3H), 3.55 (s, 2H), 3.51 (t, 2H, J=7.6 Hz), 3.16 (t, 2H, J=7.6 Hz), 2.74-2.73 (m, 4H), 2.70-2.68 (m, 4H); $^{13}$C NMR (CDCl$_3$, 150 MHz) δ 187.3, 165.1, 157.4, 152.4, 148.5, 146.5, 139.7, 139.3, 139.0, 138.3, 137.0, 129.4, 128.9, 128.0, 127.1, 126.8, 125.2, 123.3, 63.3, 54.9, 53.0, 40.6, 29.3, 28.0; HR ESI-TOF m/z 528.1950 (M+H$^+$, C$_{30}$H$_{29}$N$_3$O$_4$S, requires 528.1951).

Example 37

6-{2-3-(4'-Pyrrolidin-1-ylmethyl-biphenyl-4-yl)-propionyl]-oxazol-5-yl}-pyridine-2-carboxylic acid methyl ester, i.e., Methyl 6-(2-(3-(4'-(Pyrrolidin-1-ylmethyl)biphenyl-4-yl)propanoyl)oxazol-5-yl)pyridine-2-carboxylate (37)

Methyl 6-(2-(3-(4'-formylbiphenyl-4-yl)propanoyl)oxazol-5-yl)pyridine-2-carboxylate (19 mg, 0.043 mmol) and pyrrolidine (0.005 mL, 0.07 mmol) were dissolved in dichloroethane (2 mL) and NaBH(OAc)$_3$ (18 mg, 0.086 mmol) was added. The reaction solution was stirred under an atmosphere of Ar at ambient temperature for 3 h and then quenched with saturated aqueous NaHCO$_3$. The crude product was extracted with EtOAc and the solvent was removed in vacuo. The crude product was purified by flash chromatography (SiO$_2$, 2.5% Et$_3$N/EtOAc) to furnish methyl 6-(2-(3-(4'-(pyrrolidin-1-ylmethyl)biphenyl-4-yl)propanoyl)oxazol-5-yl)pyridine-2-carboxylate as a cloudy oil (16 mg, 75%): $^1$H NMR (CDCl$_3$, 600 MHz) δ 8.11 (d, 1H, J=7.7 Hz), 8.02 (d, 2H, J=9.0 Hz), 7.96 (t, 1H, J=7.8 Hz), 7.53-7.51 (m, 4H), 7.38 (d, 2H, J=8.0 Hz), 7.33 (d, 2H, J=8.0 Hz), 4.03 (s, 3H), 3.65 (s, 2H), 3.51 (t, 2H, J=7.6 Hz), 3.15 (t, 2H, J=7.6 Hz), 2.54 (s, 4H), 1.81-1.79 (m, 4H); $^{13}$C NMR (CDCl$_3$, 150 MHz) δ 187.3, 165.1, 157.4, 152.4, 148.5, 146.5, 139.5, 139.2, 139.1, 138.3, 138.3, 129.3, 128.8, 128.0, 127.1, 126.8, 125.2, 123.3, 60.4, 54.2, 53.1, 40.6, 29.3, 23.4; HR ESI-TOF m/z 496.2233 (M+H$^+$, C$_{30}$H$_{29}$N$_3$O$_4$, requires 496.2231).

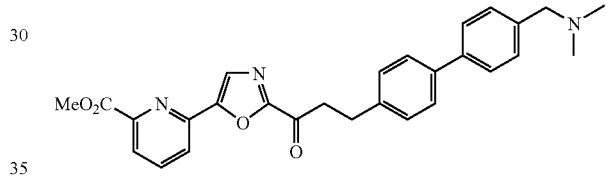

Example 38

6-{2-3-(4'-Dimethylaminomethyl-biphenyl-4-yl)-propionyl]-oxazol-5-yl}-pyridine-2-carboxylic acid methyl ester, i.e., Methyl 6-(2-(3-(4'-((Dimethylamino) methyl)biphenyl-4-yl)propanoyl)oxazol-5-yl)pyridine-2-carboxylate (38)

Methyl 6-(2-(3-(4'-formylbiphenyl-4-yl)propanoyl)oxazol-5-yl)pyridine-2-carboxylate (19 mg, 0.043 mmol) and dimethylamine (2 M in THF, 0.026 mL, 0.052 mmol) were dissolved in dichloroethane (2 mL) and NaBH(OAc)$_3$ (16 mg, 0.078 mmol) was added. The reaction solution was stirred under an atmosphere of Ar at ambient temperature for 2 h and then quenched with saturated aqueous NaHCO$_3$. The crude product was extracted with EtOAc and the solvent was removed in vacuo. The crude product was purified with preparative thin layer chromatography (SiO$_2$, 5% Et$_3$N, 5% MeOH, 90% EtOAc) to furnish methyl 6-(2-(3-(4'-((dimethylamino)methyl)biphenyl-4-yl)propanoyl)oxazol-5-yl)pyridine-2-carboxylate as a tan solid (5 mg, 25%): $^1$H NMR (CDCl$_3$, 600 MHz) δ 8.12 (d, 1H, J=7.7 Hz), 8.03 (d, 2H, J=9.6 Hz), 7.97 (t, 1H, J=7.8 Hz), 7.53 (dd, 4H, J=8.0, 4.9 Hz), 7.38 (d, 2H, J=7.9 Hz), 7.34 (d, 2H, J=8.0 Hz), 4.03 (s, 3H), 3.51 (t, 4H, J=7.6 Hz), 3.15 (t, 2H, J=7.6 Hz), 2.31 (s, 6H); $^{13}$C NMR (CDCl$_3$, 150 MHz) δ 187.3, 165.1, 157.4, 152.4, 148.5, 146.5, 139.4, 138.9, 138.3, 129.6, 128.9, 128.0, 127.2, 126.9, 125.2, 123.3, 63.8, 53.1, 45.1, 40.6, 29.3; HR ESI-TOF m/z 470.2071 (M+H$^+$, C$_{28}$H$_{27}$N$_3$O$_4$, requires 470.2074).

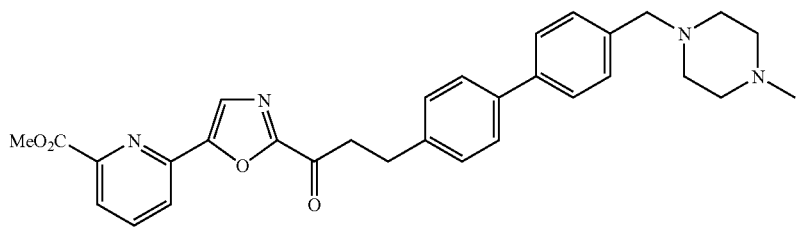 [SMILES: COC(=O)c1cccc(-c2cnc(C(=O)CCc3ccc(-c4ccc(CN5CCN(C)CC5)cc4)cc3)o2)n1]

Example 39

6-(2-{3-[4'-(4-Methyl-piperazin-1-ylmethyl)-biphenyl-4-yl]-propionyl}-oxazol-5-yl)-pyridine-2-carboxylic acid methyl ester, i.e., Methyl 6-(2-(3-(4'((4-Methylpiperazin-1-yl)methyl)biphenyl-4-yl) propanoyl)oxazol-5-yl)pyridine-2-carboxylate (39)

Methyl 6-(2-(3-(4'-formylbiphenyl-4-yl)propanoyl)oxazol-5-yl)pyridine-2-carboxylate (19 mg, 0.043 mmol) and 1-methyl piperazine (0.007 mL, 0.07 mmol) were dissolved in dichloroethane (2 mL) and NaBH(OAc)$_3$ (18 mg, 0.086 mmol) was added. The reaction solution was stirred under an atmosphere of Ar at ambient temperature for 3.5 h and then quenched with saturated aqueous NaHCO$_3$. The crude product was extracted with EtOAc and the solvent was removed in vacuo. The crude product was purified by flash chromatography (SiO$_2$, 2.5% Et$_3$N/EtOAc) to furnish methyl 6-(2-(3-(4'-((4-methylpiperazin-1-yl)methyl)biphenyl-4-yl)propanoyl) oxazol-5-yl)pyridine-2-carboxylate as a clear tan oil (13 mg, 58%): $^1$H NMR (CDCl$_3$, 600 MHz) δ 8.11 (d, 1H, J=7.7 Hz), 8.02 (d, 2H, J=9.0 Hz), 7.96 (t, 1H, J=7.8 Hz), 7.51 (dd, 4H, J=8.2, 2.2 Hz), 7.36 (d, 2H, J=8.0 Hz), 7.33 (d, 2H, J=8.0 Hz), 4.03 (s, 3H), 3.54 (s, 2H), 3.51 (t, 2H, J=7.6 Hz), 3.15 (t, 2H, J=7.6 Hz), 2.50 (bs, 8H), 2.30 (s, 3H); $^{13}$C NMR (CDCl$_3$, 150 MHz) δ 187.3, 165.1, 157.4, 152.4, 148.5, 146.5, 139.7, 139.3, 139.0, 138.3, 137.1, 129.6, 128.9, 128.0, 127.1, 126.8, 125.2, 123.3, 62.6, 55.1, 53.1, 53.0, 45.9, 40.6, 29.3; HR ESI-TOF m/z 525.2493 (M+H$^+$, C$_{31}$H$_{32}$N$_4$O$_4$, requires 525.2496).

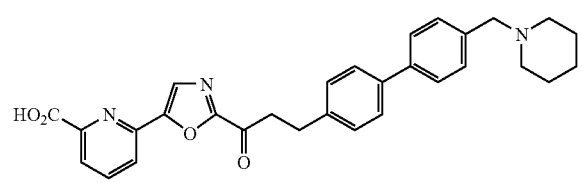 [SMILES: O=C(O)c1cccc(-c2cnc(C(=O)CCc3ccc(-c4ccc(CN5CCCCC5)cc4)cc3)o2)n1]

Example 40

6-{2-[3-(4'-Piperidin-1-ylmethyl-biphenyl-4-yl)-propionyl]-oxazol-5-yl}-pyridine-2-carboxylic acid, i.e., 6-(2-(3-(4'-(Piperidin-1-ylmethyl)biphenyl-4-yl) propanoyl)oxazol-5-yl)pyridine-2-carboxylic acid (40)

Methyl 6-(2-(3-(4'-(piperidin-1-ylmethyl)biphenyl-4-yl)propanoyl)oxazol-5-yl)pyridine-2-carboxylate (11 mg, 0.022 mmol) was dissolved in THF/H$_2$O (3:2, 2 mL) and LiOH (1.5 mg, 0.065 mmol) was added. The reaction solution was stirred at room temperature under an atmosphere of Ar for 20 min before the addition of aqueous 1 N HCl to pH 4. The reaction solution was diluted with CH$_2$Cl$_2$ and the organic and aqueous layers were separated. The aqueous layer was made basic to pH 8 with the addition of saturated aqueous NaHCO$_3$ and extracted with CH$_2$Cl$_2$. The organic phases were combined, dried over Na$_2$SO$_4$, and concentrated in vacuo. The crude product was purified by tritration in ether to provide 6-(2-(3-(4'-(piperidin-1-ylmethyl)biphenyl-4-yl) propanoyl)oxazol-5-yl)pyridine-2-carboxylic acid as a white solid (4 mg, 38%): $^1$H NMR (CDCl$_3$, 600 MHz) δ 8.22 (d, 1H, J=5.7 Hz), 8.05-8.01 (m, 3H), 7.63 (d, 2H, J=8.0 Hz), 7.58 (d, 2H, J=8.0 Hz), 7.47 (d, 2H, J=8.0 Hz), 7.33 (d, 2H, J=8.0 Hz), 4.20 (s, 2H), 3.50 (t, 21-1, J=7.5 Hz), 3.15 (t, 2H, J=7.4 Hz), 2.15-1.95 (m, 10H); $^{13}$C NMR (CDCl$_3$, 150 MHz) δ 187.2, 165.8, 157.4, 152.1, 145.4, 142.4, 140.1, 138.9, 138.0, 131.9, 129.0, 128.0, 127.6, 127.3, 127.2, 124.4, 123.2, 60.5, 52.6, 40.5, 29.4, 22.6, 22.2; HR ESI-TOF m/z 496.2227 (M+H$^+$, C$_{30}$H$_{29}$N$_3$O$_4$, requires 496.2231).

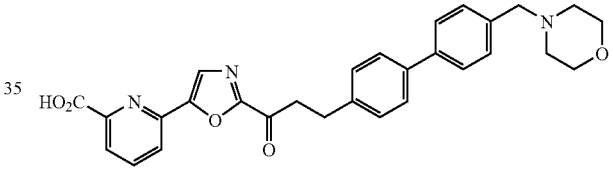

Example 41

6-{2-[3-(4'-Morpholin-4-ylmethyl-biphenyl-4-yl)-propionyl]-oxazol-5-yl}-pyridine-2-carboxylic acid, i.e., 6-(2-(3-(4'-(Morpholinomethyl) biphenyl-4-yl) propanoyl)oxazol-5-yl)pyridine-2-carboxylic acid (41)

Methyl 6-(2-(3-(4'-(morpholinomethyl)biphenyl-4-yl) propanoyl)oxazol-5-yl)pyridine-2-carboxylate (15 mg, 0.029 mmol) was dissolved in THF/H$_2$O (3:2, 2 mL) and LiOH (2 mg, 0.09 mmol) was added. The reaction solution was stirred at room temperature under an atmosphere of Ar for 25 min before the addition of aqueous 1 N HCl to pH 4. The reaction solution was diluted with CH$_2$Cl$_2$ and the organic and aqueous layers were separated. The aqueous layer was made basic to pH 8 with the addition of saturated aqueous NaHCO$_3$ and extracted with CH$_2$Cl$_2$. The organic phases were combined, dried over Na$_2$SO$_4$, and concentrated in vacuo. The crude product was purified by tritration in ether to provide 6-(2-(3-(4'-(morpholinomethyl)biphenyl-4-yl) propanoyl)oxazol-5-yl)pyridine-2-carboxylic acid as a white solid (10 mg, 69%): $^1$H NMR (CDCl$_3$, 600 MHz) δ 8.20 (d, 1H, J=7.1 Hz), 8.06 (s, 1H), 8.03-7.99 (m, 2H), 7.54 (d, 2H, J=7.7 Hz), 7.49-7.47 (m, 4H), 7.32 (d, 2H, J=7.9 Hz), 3.89 (s, 6H), 3.50 (t, 2H, J=7.4 Hz), 3.15 (t, 2H, J=7.5 Hz), 2.84 (s, 4H); $^{13}$C NMR (CDCl$_3$, 150 MHz) δ 187.3, 166.0, 157.4, 152.2, 149.4, 145.5, 141.1, 139.7, 138.9, 138.5, 130.7, 128.9, 128.0, 127.2, 127.2, 124.4, 123.2, 65.5, 61.9, 52.5, 40.6, 29.3; HR ESI-TOF m/z 498.2020 (M+H$^+$, C$_{29}$H$_{27}$N$_3$O$_5$, requires 498.2023).

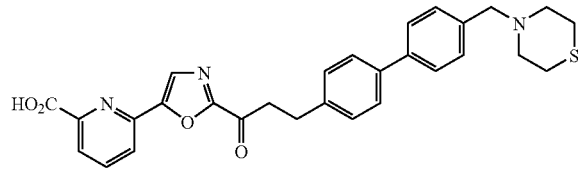 [SMILES: O=C(O)c1cccc(-c2cnc(C(=O)CCc3ccc(-c4ccc(CN5CCSCC5)cc4)cc3)o2)n1]

Example 42

6-{2-[3-(4'-Thiomorpholin-4-ylmethyl-biphenyl-4-yl)-propionyl]-oxazol-5-yl}-pyridine-2-carboxylic acid, i.e., 6-(2-(3-(4'-(Thiomorpholino methyl)biphenyl-4-yl)propanoyl)oxazol-5-yl)pyridine-2-carboxylic acid (42)

Methyl 6-(2-(3-(4'-(thiomorpholinomethyl)biphenyl-4-yl)propanoyl)oxazol-5-yl)pyridine-2-carboxylate (105 mg, 0.199 mmol) was dissolved in THF/H$_2$O (3:2, 15 mL) and LiOH (14 mg, 0.60 mmol) was added. The reaction solution was stirred at room temperature under an atmosphere of Ar for 40 min before the addition of aqueous 1 N HCl to pH 4. The reaction solution was diluted with CH$_2$Cl$_2$ and the organic and aqueous layers were separated. The aqueous layer was made basic to pH 8 with the addition of saturated aqueous NaHCO$_3$ and extracted with CH$_2$Cl$_2$. The organic phases were combined, dried over Na$_2$SO$_4$, and concentrated in vacuo. The crude product was purified by tritration in ether to provide 6-(2-(3-(4'-(thiomorpholinomethyl)biphenyl-4-yl)propanoyl)oxazol-5-yl)pyridine-2-carboxylic acid (89 mg, 87%): $^1$H NMR (CDCl$_3$, 600 MHz) δ 8.21 (d, 1H, J=6.9 Hz), 8.05-8.00 (m, 3H), 7.52 (d, 2H, J=8.1 Hz), 7.49 (d, 2H, J=8.1 Hz), 7.40 (d, 2H, J=8.0 Hz), 7.32 (d, 2H, J=8.0 Hz), 3.83 (s, 2H), 3.50 (t, 2H, J=7.5 Hz), 3.15 (t, 2H, J=7.5 Hz), 2.99 (s, 4H), 2.83-2.82 (m, 4H); $^{13}$C NMR (CDCl$_3$, 150 MHz) δ 187.3, 157.4, 152.2, 149.6, 145.5, 140.7, 139.6, 138.9, 138.6, 130.4, 128.9, 128.0, 127.2, 127.1, 124.5, 123.2, 62.4, 54.2, 40.6, 29.3, 26.9; HR ESI-TOF m/z 514.1784 (M+H$^+$, C$_{29}$H$_{27}$N$_3$O$_4$S, requires 514.1795).

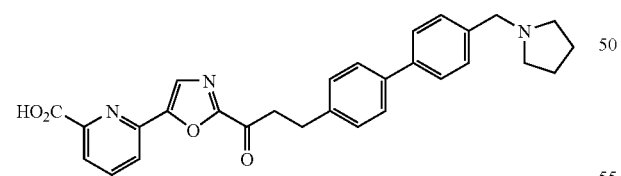

Example 43

6-{2-[3-(4'-Pyrrolidin-1-ylmethyl-biphenyl-4-yl)-propionyl]-oxazol-5-yl}-pyridine-2-carboxylic acid, i.e., 6-(2-(3-(4'-(Pyrrolidin-1-ylmethyl)biphenyl-4-yl)propanoyl)oxazol-5-yl)pyridine-2-carboxylic acid (43)

Methyl 6-(2-(3-(4'-(pyrrolidin-1-ylmethyl)biphenyl-4-yl)propanoyl)oxazol-5-yl)pyridine-2-carboxylate (13 mg, 0.026 mmol) was dissolved in THF/H$_2$O (3:2, 2 mL) and LiOH (1.8 mg, 0.079 mmol) was added. The reaction solution was stirred at room temperature under an atmosphere of Ar for 25 min before the addition of aqueous 1 N HCl to pH 4. The reaction solution was diluted with CH$_2$Cl$_2$ and the organic and aqueous layers were separated. The aqueous layer was made basic to pH 8 with the addition of saturated aqueous NaHCO$_3$ and extracted with CH$_2$Cl$_2$. The organic phases were combined, dried over Na$_2$SO$_4$, and concentrated in vacuo. The crude product was purified by tritration in ether to provide 6-(2-(3-(4'-(pyrrolidin-1-ylmethyl)biphenyl-4-yl)propanoyl)oxazol-5-yl)pyridine-2-carboxylic acid as a white solid (7 mg, 55%): $^1$H NMR (CDCl$_3$, 600 MHz) δ 8.22 (d, 1H, J=6.5 Hz), 8.04-8.02 (m, 3H), 7.67 (d, 2H, J=7.9 Hz), 7.58 (d, 2H, J=7.9 Hz), 7.47 (d, 2H, J=8.1 Hz), 7.33 (d, 2H, J=8.0 Hz), 4.26 (s, 2H), 3.50 (t, 2H, J=7.5 Hz), 3.16 (t, 2H, J=7.5 Hz), 2.45-1.90 (m, 8H); $^{13}$C NMR (CDCl$_3$, 150 MHz) δ 187.3, 164.8, 157.5, 151.8, 145.3, 142.3, 140.0, 139.2, 138.0, 131.0, 129.0, 128.6, 128.1, 127.7, 127.2, 124.3, 123.6, 58.0, 52.8, 40.6, 29.4, 23.1; HR ESI-TOF m/z 482.2071 (M+H$^+$, C$_{29}$H$_{27}$N$_3$O$_4$, requires 482.2074.

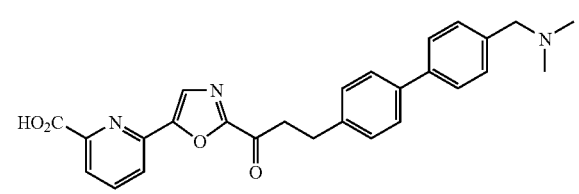 [SMILES: CN(C)Cc1ccc(-c2ccc(CCC(=O)c3ncc(-c4cccc(C(=O)O)n4)o3)cc2)cc1]

Example 44

6-{2-[3-(4'-Dimethylaminomethyl-biphenyl-4-yl)-propionyl]-oxazol-5-yl}-pyridine-2-carboxylic acid (44)

Methyl 6-(2-(3-(4'-((Dimethylamino)methyl)biphenyl-4-yl)propanoyl)oxazol-5-yl)pyridine-2-carboxylate was dissolved in THF/H$_2$O (3:2, 2 mL) and LiOH was added. The reaction solution was stirred at room temperature under an atmosphere of Ar for 25 min before the addition of aqueous 1 N HCl to pH 4. The reaction solution was diluted with CH$_2$Cl$_2$ and the organic and aqueous layers were separated. The aqueous layer was made basic to pH 8 with the addition of saturated aqueous NaHCO$_3$ and extracted with CH$_2$Cl$_2$. The organic phases were combined, dried over Na$_2$SO$_4$, and concentrated in vacuo. The crude product was purified by tritration in ether to provide 6-{2-[3-(4'-Dimethylaminomethyl-biphenyl-4-yl)-propionyl]oxazol-5-yl}-pyridine-2-carboxylic acid.

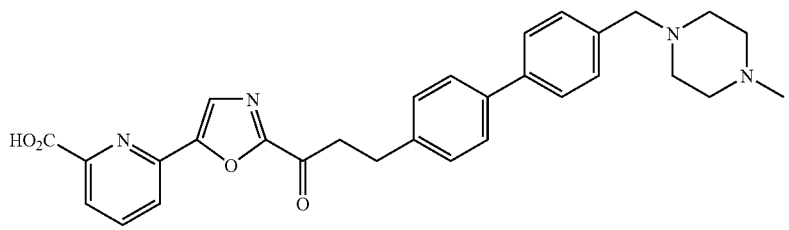 [SMILES: CN1CCN(Cc2ccc(-c3ccc(CCC(=O)c4ncc(-c5cccc(C(=O)O)n5)o4)cc3)cc2)CC1]

Example 45

6-(2-{3-[4'-(4-Methyl-piperazin-1-ylmethyl)-biphenyl-4-yl]-propionyl}-oxazol-5-yl)-pyridine-2-carboxylic acid, i.e., 6-(2-(3-(4'-((4-Methylpiperazin-1-yl)methyl)biphenyl-4-yl)propanoyl)oxazol-5-yl)pyridine-2-carboxylic acid (45)

Methyl 6-(2-(3-(4'-((4-methylpiperazin-1-yl)methyl)biphenyl-4-yl)propanoyl)oxazol-5-yl)pyridine-2-carboxylate (10 mg, 0.019 mmol) was dissolved in THF/H$_2$O (3:2, 2 mL) and LiOH (1 mg, 0.06 mmol) was added. The reaction solution was stirred at room temperature under an atmosphere of Ar for 40 min before the addition of aqueous 1 N HCl to pH 4. The reaction solution was diluted with CH$_2$Cl$_2$ and the organic and aqueous layers were separated. The aqueous layer was made basic to pH 8 with the addition of saturated aqueous NaHCO$_3$ and extracted with CH$_2$Cl$_2$. The organic phases were combined, dried over Na$_2$SO$_4$, and concentrated in vacuo. The crude product was purified by tritration in ether to provide 6-(2-(3-(4'-((4-methylpiperazin-1-yl)methyl)biphenyl-4-yl)propanoyl)oxazol-5-yl)pyridine-2-carboxylic acid as a white solid (2 mg, 21%): $^1$H NMR (CDCl$_3$, 600 MHz) δ 8.17 (s, 1H), 7.93 (s, 3H), 7.48 (d, 2H, J=7.8 Hz), 7.44 (d, 2H, J=7.8 Hz), 7.31-7.27 (m, 4H), 3.68 (s, 2H), 3.47 (t, 2H, J=6.9 Hz), 3.15 (t, 2H, J=6.9 Hz), 2.82 (bs, 4H), 2.69 (s, 3H), 2.10-2.00 (m, 4H); HR ESI-TOF m/z 511.2334 (M+H$^+$, C$_{30}$H$_{30}$N$_4$O$_4$, requires 511.2340).

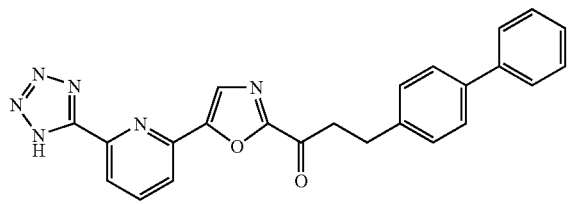 [SMILES: O=C(CCc1ccc(-c2ccccc2)cc1)c1ncc(-c2cccc(-c3nnn[nH]3)n2)o1]

Example 46

3-Biphenyl-4-yl-1-{5-[6-(1H-tetrazol-5-yl)-pyridin-2-yl]-oxazol-2-yl}-propan-1-one, i.e., 1-(5-(6-(1H-Tetrazol-5-yl)pyridin-2-yl)oxazol-2-yl)-3-(biphenyl-4-yl)propan-1-one (46)

2-Cyano-6-(2-(3-(biphenyl-4-yl)propanoyl)oxazol-5-yl)pyridine (30 mg, 0.075 mmol), sodium azide (1.1 equiv) and NH$_4$Cl (0.25 equiv) were dissolved in DMF (1 mL). The mixture was warmed at 110° C. in a sealed vial for 24 h. The solution was evaporated in vacuo and flash reverse phase chromatography (C18, 0-30% MeCN/H$_2$O) yielded the title compound as a yellow solid (18 mg, 58%): $^1$H NMR (DMSO-d$_6$, 600 MHz) δ 8.05-8.04 (m, 2H), 7.96 (t, 1H, J=7.8 Hz), 7.77 (d, 1H, J=7.8 Hz), 7.62 (d, 2H, J=7.8 Hz), 7.57 (d, 2H, J=7.8 Hz), 7.42 (t, 2H, J=7.8 Hz), 7.37-7.30 (m, 3H), 3.47 (t, 2H, J=7.2 Hz), 3.03 (t, 2H, J=7.2 Hz); HR ESI-TOF m/z 423.1556 (M+H$^+$, C$_{24}$H$_{19}$N$_6$O$_2$, requires 423.1564).

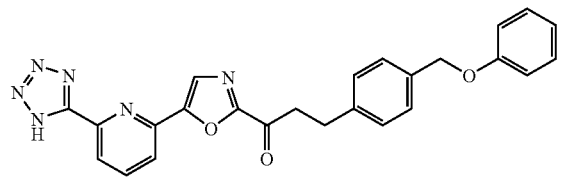 [SMILES: O=C(CCc1ccc(COc2ccccc2)cc1)c1ncc(-c2cccc(-c3nnn[nH]3)n2)o1]

Example 47

3-(4-Phenoxymethyl-phenyl)-1-{5-[6-(1H-tetrazol-5-yl)-pyridin-2-yl]-oxazol-2-yl}-propan-1-one, i.e., 1-(5-(6-(1H-Tetrazol-5-yl)pyridin-2-yl)oxazol-2-yl)-3-(4-(phenoxymethyl)phenyl)propan-1-one (47)

2-Cyano-6-(2-(3-(4-(phenoxymethyl)phenyl)propanoyl)oxazol-5-yl)pyridine (98 mg, 0.24 mmol), sodium azide (31 mg, 0.48 mmol), and zinc bromide (27 mg, 0.12 mmol) were dissolved in i-PrOH/H$_2$O (1:2, 2.1 mL) and warmed at reflux for 24 h. The reaction solution was allowed to cool to ambient temperature and was quenched with aqueous 1 N HCl. The solution was diluted with EtOAc and the organic phase was washed with saturated aqueous NaCl, dried over Na$_2$SO$_4$, and the solvent was removed in vacuo. The crude product was purified by tritration in 3% CH$_2$Cl$_2$/ether to provide 1-(5-(6-(1H-tetrazol-5-yl)pyridin-2-yl)oxazol-2-yl)-3-(4-(phenoxymethyl)phenyl)propan-1-one as a pale yellow solid (60 mg, 55%): NMR (DMSO-d$_6$, 600 MHz) δ 8.25-8.24 (m, 3H), 8.08-8.05 (m, 1H), 7.38 (d, 2H, J=8.0 Hz), 7.31-7.27 (m, 4H), 6.99 (d, 2H, J=8.7 Hz), 6.92 (t, 1H, J=7.3 Hz), 3.47 (t, 2H, J=7.5 Hz), 3.02 (t, 2H, J=7.5 Hz); $^{13}$C NMR (DMSO-d$_6$, 150 MHz) δ 207.8, 188.3, 159.7, 158.7, 153.0, 147.3, 141.6, 141.2, 136.2, 130.8, 129.7, 129.6, 129.2, 124.1, 123.3, 122.0, 116.1, 70.2, 32.0, 30.0; HR ESI-TOF m/z 453.1681 (M+H$^+$, C$_{25}$H$_{20}$N$_6$O$_3$, requires 453.1670).

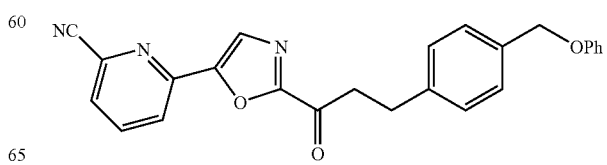

Example 48

2-Cyano-6-(2-(3-(4-(phenoxymethylphenyl)propanoyl)oxazol-5-yl)pyridine, i.e., 6-{2-[3-(4-Phenyoxymethyl)phenylpropionyl]oxazol-5-yl}pyridine-2-carbonitrile (48)

2-Cyano-6-(2-(1-hydroxy-3-(4-(phenoxymethyl)phenyl)propyl)oxazol-5-yl)pyridine (133 mg, 0.323 mmol) was dissolved in anhydrous $CH_2Cl_2$ (4 mL) and Dess-Martin periodinane (205 mg, 0.485 mmol) was added. The reaction solution was stirred at room temperature under an atmosphere of Ar for 2.5 h. The addition of saturated aqueous $NaHCO_3$ quenched the reaction and the organic layer was washed with saturated aqueous $Na_2S_2O_3$ and saturated aqueous NaCl. The organic layer was dried over $Na_2SO_4$ and the solvent was removed in vacuo. The crude product was purified by flash chromatography ($SiO_2$, 0-1% $MeOH/CH_2Cl_2$) to provide 2-cyano-6-(2-(3-(4-(phenoxymethyl)phenyl)propanoyl)oxazol-5-yl)pyridine as a yellow solid (98 mg, 74%): $^1H$ NMR ($CDCl_3$, 500 MHz) δ 8.04 (dd, 1H, J=8.1, 0.9 Hz), 7.98-7.95 (m, 2H), 7.68 (dd, 1H, J=7.7, 0.9 Hz), 7.37 (d, 2H, J=8.0 Hz), 7.30-7.26 (m, 4H), 6.97-6.94 (m, 3H), 5.03 (s, 2H), 3.74 (t, 2H, J=7.5 Hz), 3.12 (t, 2H, J=7.5 Hz); $^{13}C$ NMR ($CDCl_3$, 150 MHz) δ 187.3, 158.7, 157.5, 151.4, 147.8, 140.0, 138.4, 135.1, 134.3, 129.4, 128.5, 128.7, 128.1, 127.8, 123.0, 120.9, 116.5, 114.8, 69.7, 40.7, 29.3; HR ESI-TOF m/z 410.1501 ($M+H^+$, $C_{25}H_{19}N_3O_3$, requires 410.1499).

Biological Methods:

Enzyme assays were performed at 20-23° C. with purified recombinant rat FAAH expressed in *E. coli* (Patricelli, M. P.; Lashuel, H. A.; et al. *Biochemistry* 1998, 37, 15177-15187) (unless indicated otherwise) or with solubilized COS-7 membrane extracts from cells transiently transfected with human FAAH cDNA (Giang, D. K.; Cravatt, B. F. *Proc. Natl. Acad. Sci. U.S.A.* 1997, 94, 2238-2242) (where specifically indicated) in a buffer of 125 mM Tris/1 mM EDTA/0.2% glycerol/0.02% Triton X-100/0.4 mM Hepes, pH 9.0 buffer (Patricelli, M. P.; Patterson, J. P.; et al. *Bioorg. Med. Chem. Lett.* 1998, 8, 613-618). The initial rates of hydrolysis (≦10-20% reaction) were monitored using enzyme concentrations at least three times below the measured $K_i$ by following the breakdown of $^{14}C$-oleamide and $K_i$'s (standard deviations are provided in Supporting Information tables) were established as described (Dixon plot) (Boger, D. L. et al. *Proc. Natl. Acad. Sci. U.S.A.* 2000, 97, 5044-5049). Lineweaver-Burk analysis previously established reversible, competitive inhibition (Boger, D. L. et al. *J. Med. Chem.* 2005, 48, 1849-1856). Results for compounds tested are presented in Table 1. NT=no data available.

TABLE 1

| Ex. | Human $K_i$ (nM) | Rat $K_i$ (nM) |
|---|---|---|
| 11a | 0.45 | 1.3 |
| 11b | NT | 5300 |
| 11c | NT | 25 |
| 11d | NT | 2100 |
| 11e | 5 | 1 |
| 11f | NT | 3.4 |
| 11g | NT | 2 |
| 11h | NT | 3.2 |
| 11i | NT | 2.2 |
| 11j | 2.9 | 0.75 |
| 11k | 0.6 | 0.38 |
| 12 | NT | 13 |
| 13 | NT | 54 |
| 14 | NT | 65 |
| 15 | NT | 33 |
| 16 | NT | 2 |
| 17 | NT | 3.5 |
| 18 | NT | 6.1 |
| 19 | NT | 4.6 |
| 20 | NT | 3.0 |
| 21 | 1.2 | 1.2 |
| 22 | NT | 3 |
| 23 | NT | 2.2 |
| 24 | NT | 22 |
| 25 | NT | 14 |
| 26 | NT | 1.2 |
| 27 | NT | 1.5 |
| 28 | NT | 1.6 |
| 29 | NT | 50 |
| 30 | NT | 2.3 |
| 31 | NT | 1.1 |
| 32 | NT | 0.6 |
| 33 | NT | 44 |
| 34 | NT | 9 |
| 35 | NT | 31 |
| 36 | NT | 5 |
| 37 | NT | 18 |
| 38 | NT | 29 |
| 39 | NT | 200 |
| 40 | NT | 44 |
| 41 | NT | 150 |
| 42 | NT | 28 |
| 43 | NT | 127 |
| 44 | NT | 150 |
| 45 | NT | 1227 |
| 46 | NT | 27 |
| 47 | NT | 21 |
| 48 | NT | 3.0 |

$IC_{50}$ values were determined from the inhibition observed at 3-5 different test compound concentrations (from three or more trials at each concentration) using the formula $IC_{50}=[I]/[K_0/K_i)-1]$, where $K_0$ is the control reaction rate without inhibitor and $K_i$ is the rate with test compound at concentration [I] (Conde-Frieboes, K. et al. *J. Am. Chem. Soc.* 1996, 118, 5519-5525). Results are presented in Table 2. NT=no data available.

TABLE 2

| Ex. | Human $IC_{50}$ (nM) | Rat $IC_{50}$ (nM) |
|---|---|---|
| 11a | NT | NT |
| 11b | NT | NT |
| 11c | NT | NT |
| 11d | NT | NT |
| 11e | NT | NT |
| 11f | NT | NT |
| 11g | NT | NT |
| 11h | NT | NT |
| 11i | NT | NT |
| 11j | NT | NT |
| 11k | NT | NT |
| 12 | 2 | 5 |
| 13 | 3 | 6 |
| 14 | 2.7 | 1.5 |
| 15 | 0.3 | 0.2 |
| 16 | 1.2 | 1 |
| 17 | 0.8 | 2.5 |
| 18 | 1 | 0.5 |
| 19 | 0.8 | 2.5 |
| 20 | 11 | 2 |
| 21 | 3 | 0.5 |
| 22 | 2 | 2 |
| 23 | 5 | 8 |

TABLE 2-continued

| Ex. | Human IC$_{50}$ (nM) | Rat IC$_{50}$ (nM) |
|---|---|---|
| 24 | 2 | 0.6 |
| 25 | 0.5 | 0.3 |
| 26 | 2 | 0.5 |
| 27 | 0.4 | 0.5 |
| 28 | 29 | 1.5 |
| 29 | 7 | 3 |
| 30 | 16 | 3 |
| 31 | 22 | 2 |
| 32 | 500 | 17 |
| 33 | 580 | 44 |
| 34 | NT | NT |
| 35 | 21 | 2 |
| 36 | NT | NT |
| 37 | NT | NT |
| 38 | NT | NT |
| 39 | NT | NT |
| 40 | NT | NT |
| 41 | 9 | 3 |
| 42 | NT | NT |
| 43 | NT | NT |
| 44 | NT | NT |
| 45 | NT | NT |
| 46 | 83 | 9 |
| 47 | NT | NT |
| 48 | NT | NT |

All publications, patents, and patent applications are incorporated herein by reference. While in the foregoing specification this disclosed subject matter has been described in relation to certain preferred embodiments thereof, and many details have been set forth for purposes of illustration, it will be apparent to those skilled in the art that the disclosed subject matter is susceptible to additional embodiments and that certain of the details described herein may be varied considerably without departing from the basic principles of the disclosed subject matter. Moreover, it will be understood that the invention is not limited to the foregoing detailed description, but is recited by the appended claims as properly construed under principles of patent law.

What is claimed is:
1. A compound of Formula (I):

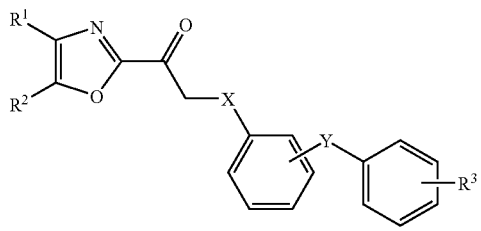

(I)

wherein
$R^1$ is H;
$R^2$ is pyridyl optionally substituted with $R^x$;
or $R^1$ and $R^2$ taken together with the oxazole to which they are attached form oxazolo[4,5-b]pyridin-2-yl;
where $R^x$ is —$C_{1-6}$alkyl; —$C_{3-6}$cycloalkyl; —$CF_3$; —CN; —C(O)$C_{1-4}$alkyl optionally substituted with one, two, or three fluoro substituents; —$CO_2C_{1-4}$alkyl; —$CO_2H$; —C(O)N($R^a$)$R^b$; —OH; —$OC_{1-6}$alkyl; halo; —$NO_2$; —$NR^aR^b$; —N($R^a$)C(O)$R^b$; —N($R^a$)$SO_2R^b$; —$SO_2N(R^a)R^b$; —S(O)$_{0-2}R^f$; or tetrazolyl;

where $R^a$ and $R^b$ are each independently —H, —$C_{1-6}$alkyl, or —$C_{3-6}$cycloalkyl; and
$R^f$ is —$C_{1-4}$alkyl optionally substituted with one, two, or three fluoro substituents;
$R^3$ is —H; —$C_{1-6}$alkyl; $C_{3-6}$cycloalkyl; —$CF_3$; —CN; —C(O)$C_{1-4}$alkyl optionally substituted with one, two, or three fluoro substituents; —$CO_2C_{1-4}$alkyl; —$CO_2H$; —C(O)N($R^c$)$R^d$; —OH; —$OC_{1-6}$alkyl; -halo; —$NO_2$; —$NR^cR^d$; —N($R^c$)C(O)$R^d$; —N($R^c$)$SO_2R^d$; —$SO_2N(R^c)R^d$; —S(O)$_{0-2}R^f$; or —$CH_2N(R^g)R^h$;
where $R^c$ and $R^d$ are each independently —H, —$C_{1-6}$alkyl, or —$C_{3-6}$cycloalkyl;
$R^f$ is —$C_{1-4}$alkyl optionally substituted with one, two, or three fluoro substituents; and
$R^g$ and $R^h$ are each independently H or $C_{1-4}$alkyl; or $R^g$ and $R^h$ taken together with the nitrogen to which they are attached form a monocyclic saturated heterocycloalkyl group;
X is —$CH_2$—, —O—, or —CH(OH)—; and
Y is absent or is —$CH_2$—, —O—, —$NR^i$—, —$CH_2O$—, or —$OCH_2$—;
wherein $R^i$ is —H or —$C_{1-6}$alkyl; and provided that when Y is absent, a single bond is present between the two phenyl rings of formula I or;
a pharmaceutically acceptable salt of a compound of Formula (I).

2. A compound according to claim 1 wherein $R^2$ is unsubstituted 2-pyridyl.
3. A compound according to claim 1 wherein $R^2$ is 2-pyridyl substituted with —CN, —$CO_2Me$, —$CO_2Et$, —$CO_2H$, or —$CONH_2$.
4. A compound according to claim 1 selected from the group consisting of compounds of Formula (I) wherein $R^3$ is —H.
5. A compound according to claim 1 wherein $R^3$ is —$CH_2N(R^g)R^h$.
6. A compound according to claim 5 wherein $R^g$ and $R^h$ are both methyl.
7. A compound according to claim 5 wherein $R^g$ and $R^h$ are taken together with the nitrogen to which they are attached to form piperidine, morpholine, thiomorpholine, pyrrolidine, or N-methylpiperazine.
8. A compound according to claim 1 wherein X is —$CH_2$— or —O—.
9. A compound according to claim 1 wherein X is —O—.
10. A compound according to claim 8 wherein X is —$CH_2$—.
11. A compound according to claim 1 wherein Y is absent or is selected from the group consisting of —$CH_2$—, —O—, or —$CH_2O$—.
12. A compound of claim 1 selected from the group consisting of:
1-Oxo-1-[5-(2-pyridyl)oxazol-2-yl]-3-(4-(benzyloxy)phenyl)propane;
2-(4-(Benzyloxy)phenoxy)-1-(5-(pyridin-2-yl)oxazol-2-yl)ethanone;
1-Oxo-1-[5-(2-pyridyl)oxazol-2-yl]-3-(3-(benzyloxy)phenyl)-propane;
2-(3-(Benzyloxy)phenoxy)-1-(5-(pyridin-2-yl)oxazol-2-yl)ethanone;
3-(4-(Phenoxymethyl)phenyl)-1-(5-(pyridin-2-yl)oxazol-2-yl)propan-1-one;
1-Oxo-1-[5-(2-pyridyl)oxazol-2-yl]-3-(4-phenoxyphenyl)propane;
1-Oxo-1-[5-(2-pyridyl)oxazol-2-yl]-3-(4-(phenylamino)phenyl)propane;

1-Oxo-1-[5-(2-pyridyl)oxazol-2-yl]-3-(4-benzylphenyl)propane;
1-Oxo-1-[5-(2-pyridyl)oxazol-2-yl]-3-(4-biphenyl)propane;
3-(4-(Benzyloxy)phenyl)-1-(oxazolo[4,5-b]pyridin-2-yl)propan-1-one;
6-{2-[3-(4-Phenoxy-phenyl)-propionyl]-oxazol-5-yl}-pyridine-2-carboxylic acid methyl ester;
6-{2-[3-(4-Phenoxy-phenyl)-propionyl]-oxazol-5-yl}-nicotinic acid methyl ester;
6-{2-[3-(4-Phenoxy-phenyl)-propionyl]-oxazol-5-yl}-pyridine-2-carboxylic acid;
6-{2-[3-(4-Phenoxy-phenyl)-propionyl]-oxazol-5-yl}-nicotinic acid;
6-{2-[3-(4-Phenoxymethyl-phenyl)-propionyl]-oxazol-5-yl}-pyridine-2-carboxylic acid methyl ester;
6-{2-[3-(4-Phenoxymethyl-phenyl)-propionyl]-oxazol-5-yl}-nicotinic acid methyl ester;
6-{2-[3-(4-Phenoxymethyl-phenyl)-propionyl]-oxazol-5-yl}-pyridine-2-carboxylic acid;
6-{2-[3-(4-Phenoxymethyl-phenyl)-propionyl]-oxazol-5-yl}-nicotinic acid;
6-[2-(3-Biphenyl-4-yl-propionyl)-oxazol-5-yl]-pyridine-2-carbonitrile;
6-[2-(3-Biphenyl-4-yl-propionyl)-oxazol-5-yl]-pyridine-2-carboxylic acid methyl ester;
6-[2-(3-Biphenyl-4-yl-propionyl)-oxazol-5-yl]-pyridine-2-carboxylic acid ethyl ester;
6-[2-(3-Biphenyl-4-yl-propionyl)-oxazol-5-yl]-nicotinic acid methyl ester;
6-[2-(3-Biphenyl-4-yl-propionyl)-oxazol-5-yl]-pyridine-2-carboxylic acid;
6-[2-(3-Biphenyl-4-yl-propionyl)-oxazol-5-yl]-nicotinic acid;
6-[2-(3-Biphenyl-4-yl-propionyl)-oxazol-5-yl]-pyridine-2-carboxylic acid amide;
6-[2-(3-Biphenyl-4-yl-propionyl)-oxazol-5-yl]-nicotinamide;
4-[2-(3-Biphenyl-4-yl-propionyl)-oxazol-5-yl]-pyridine-2-carboxylic acid methyl ester;
4-[2-(3-Biphenyl-4-yl-propionyl)-oxazol-5-yl]-pyridine-2-carboxylic acid;
3-Biphenyl-4-yl-1-(5-pyridin-4-yl-oxazol-2-yl)-propan-1-one;
3-Biphenyl-4-yl-1-(5-pyridin-3-yl-oxazol-2-yl)-propan-1-one;
5-[2-(3-Biphenyl-4-yl-propionyl)-oxazol-5-yl]-pyridine-2-carboxylic acid methyl ester;
5-[2-(3-Biphenyl-4-yl-propionyl)-oxazol-5-yl]-pyridine-2-carboxylic acid;
6-{2-[3-(4'-Piperidin-1-ylmethyl-biphenyl-4-yl)-propionyl]-oxazol-5-yl}-pyridine-2-carboxylic acid methyl ester;
6-{2-[3-(4'-Morpholin-4-ylmethyl-biphenyl-4-yl)-propionyl]-oxazol-5-yl}-pyridine-2-carboxylic acid methyl ester;
6-{2-[3-(4'-Thiomorpholin-4-ylmethyl-biphenyl-4-yl)-propionyl]-oxazol-5-yl}-pyridine-2-carboxylic acid methyl ester;
6-{2-[3-(4'-Pyrrolidin-1-ylmethyl-biphenyl-4-yl)-propionyl]-oxazol-5-yl}-pyridine-2-carboxylic acid methyl ester;
6-{2-[3-(4'-Dimethylaminomethyl-biphenyl-4-yl)-propionyl]-oxazol-5-yl}-pyridine-2-carboxylic acid methyl ester;
6-(2-{3-[4'-(4-Methyl-piperazin-1-ylmethyl)-biphenyl-4-yl]-propionyl}-oxazol-5-yl)-pyridine-2-carboxylic acid methyl ester;
6-{2-[3-(4'-Piperidin-1-ylmethyl-biphenyl-4-yl)-propionyl]-oxazol-5-yl}-pyridine-2-carboxylic acid;
6-{2-[3-(4'-Morpholin-4-ylmethyl-biphenyl-4-yl)-propionyl]-oxazol-5-yl}-pyridine-2-carboxylic acid;
6-{2-[3-(4'-Thiomorpholin-4-ylmethyl-biphenyl-4-yl)-propionyl]-oxazol-5-yl}-pyridine-2-carboxylic acid;
6-{2-[3-(4'-Pyrrolidin-1-ylmethyl-biphenyl-4-yl)-propionyl]-oxazol-5-yl}-pyridine-2-carboxylic acid;
6-{2-[3-(4'-Dimethylaminomethyl-biphenyl-4-yl)-propionyl]-oxazol-5-yl}-pyridine-2-carboxylic acid;
6-(2-{3-[4'-(4-Methyl-piperazin-1-ylmethyl)-biphenyl-4-yl]-propionyl}-oxazol-5-yl)-pyridine-2-carboxylic acid;
3-Biphenyl-4-yl-1-{5-[6-(1H-tetrazol-5-yl)-pyridin-2-yl]-oxazol-2-yl}-propan-1-one;
3-(4-Phenoxymethyl-phenyl)-1-{5-[6-(1H-tetrazol-5-yl)-pyridin-2-yl]-oxazol-2-yl}-propan-1-one; and
6-{2-[3-(4-phenoxymethylphenyl)-propionyl]-oxazol-5-yl}-pyridine-2-carbonitrile; or
a pharmaceutically acceptable salt thereof.

13. A pharmaceutical composition for arresting the development, relieving or diminishing the symptoms of a disease, disorder, or medical condition mediated by FAAH activity, comprising:
(a) an effective amount of at least one compound of Formula (I) of claim 1 or a pharmaceutically acceptable salt, a pharmaceutically acceptable prodrug, or an pharmaceutically active metabolite thereof, or any combination thereof; and
(b) a pharmaceutically acceptable excipient.

14. A pharmaceutical composition comprising an effective amount of a compound according to claim 12, and pharmaceutically acceptable excipient.

15. A pharmaceutical composition according to claim 13, further comprising: an analgesic selected from the group consisting of opioids and non-steroidal anti-inflammatory drugs.

16. A pharmaceutical composition according to claim 13, further comprising: an active ingredient selected from the group consisting of aspirin, acetaminophen, opioids, ibuprofen, naproxen, COX-2 inhibitors, gabapentin, pregabalin, and tramadol.

17. A compound of Formula (I):

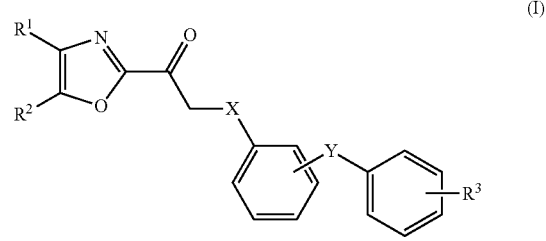

wherein
$R^1$ is H;
$R^2$ is pyridyl optionally substituted with $R^x$;
where $R^x$ is —$C_{1-6}$alkyl; —$C_{3-6}$cycloalkyl; —$CF_3$; —CN; —C(O)$C_{1-4}$alkyl optionally substituted with one, two, or three fluoro substituents; —$CO_2C_{1-4}$alkyl; —$CO_2H$; —C(O)N($R^a$)$R^b$; —OH; —$OC_{1-6}$ alkyl; halo; —NO$_2$; —NR$^a$R$^b$; —N(R$^a$)C(O)R$^b$; —N(R$^a$)SO$_2$R$^b$; —SO$_2$N(R$^a$)R$^b$; —S(O)$_{0-2}$R$^f$; or tetrazolyl;

where R$^a$ and R$^b$ are each independently —H, —C$_{1-6}$alkyl, or —C$_{3-6}$cycloalkyl; and R$^f$ is —C$_{1-4}$alkyl optionally substituted with one, two, or three fluoro substituents;

R$^3$ is —H; —C$_{1-6}$alkyl; C$_{3-6}$cycloalkyl; —CF$_3$; —CN; —C(O)C$_{1-4}$alkyl optionally substituted with one, two, or three fluoro substituents; —CO$_2$C$_{1-4}$alkyl; —CO$_2$H; —C(O)N(R$^c$)R$^d$; —OH; —OC$_{1-6}$alkyl; —halo; —NO$_2$; NR$^c$; R$^d$; —N(R$^c$)C(O)R$^d$; —N(R$^c$)SO$_2$R$^d$; —SO$_2$N(R$^c$)R$^d$; —S(O)$_{0-2}$R$^f$; or —CH$_2$N(R$^g$)R$^h$;

where R$^c$ and R$^d$ are each independently —H, —C$_{1-6}$alkyl, or —C$_{3-6}$cycloalkyl;

R$^f$ is —C$_{1-4}$ optionally substituted with one, two, or three fluoro substituents; and R$^g$ and R$^h$ are each independently H or C$_{1-4}$alkyl; or R$^g$ and R$^h$ taken together with the nitrogen to which they are attached form a monocyclic saturated heterocycloalkyl group;

X is —CH$_2$—, —O—, —S—, —S(O)$_2$—, —N(R$^i$)—, or —CH(OH)—; and

Y is absent or is —CH$_2$—, —O—, —S—, —S(O)$_2$—, —S(O)$_2$—, —NR$^i$—, —CH$_2$O—, or -OCH$_2$—;

wherein R$^i$ is —H or —C$_{1-6}$alkyl; and provided that when Y is absent, a single bond is present between the two phenyl rings of formula I; or a pharmaceutically acceptable salt thereof.

* * * * *

UNITED STATES PATENT AND TRADEMARK OFFICE
CERTIFICATE OF CORRECTION

PATENT NO. : 8,372,823 B2  
APPLICATION NO. : 12/600728  
DATED : February 12, 2013  
INVENTOR(S) : Dale L. Boger Page 1 of 3

It is certified that error appears in the above-identified patent and that said Letters Patent is hereby corrected as shown below:

In the Specifications

In column 1, line 9, delete "Al" and insert --A1--, therefor

In column 2, line 13, delete "J" and insert --J.--, therefor

In column 4, line 66, before "form", insert --to--, therefor

In column 5, line 13, delete "substitutent" and insert --substituent--, therefor In column 9, line 51, after "phosphorus", insert --sulphur--, therefor In column 9, line 52, after "chlorine", insert --iodine--, therefor In column 14, line 66, before "available", delete "that become", therefor In column 18, line 12, delete "Aryl" and insert --aryl--, therefor In column 18, line 13, delete "scheme" and insert --Scheme--, therefor In column 18, line 36, delete "required" and insert --requires--, therefor In column 18, line 48, before "stirred", insert --was--, therefor In column 19, line 50, after "3354)", insert --.--, therefor In column 21, line 30, after "P.", insert --,--, therefor In column 25, line 3, delete "(S34)" and insert --(S34--, therefor In column 25, line 16, delete "tent" and insert --tert--, therefor In column 30, line 40 (Approx.), delete "01" and insert --ol--, therefor Signed and Sealed this  
Twenty-eighth Day of January, 2014

Michelle K. Lee  
*Deputy Director of the United States Patent and Trademark Office*

In column 34, line 39, after "129.4", delete "128.7", therefor

In column 35, line 7, delete "tritration" and insert --titration--, therefor

In column 35, line 55, delete "tritration" and insert --titration--, therefor

In column 45, line 55, delete "6-{2-3-(4'" and insert --6-{2-[3-(4'--, therefor

In column 46, line 40, delete "6-{2-3-(4'" and insert --6-{2-[3-(4'--, therefor

In column 48, line 18 (Approx.), delete "tritration" and insert --titration--, therefor In column 48, line 24, delete "21-1" and insert --2H--, therefor In column 48, line 60, delete "tritration" and insert --titration--, therefor In column 49, line 20, delete "(Thiomorpholino methyl)" and insert --(Thiomorpholinomethyl)--, therefor In column 49, line 35, delete "tritration" and insert --titration--, therefor In column 50, line 11 (Approx.), delete "tritration" and insert --titration--, therefor In column 50, line 22, delete "2074." and insert --2074).--, therefor In column 50, line 64-65, delete "tritration" and insert --titration--, therefor In column 51, line 32, delete "tritration" and insert --titration--, therefor In column 52, line 47 (Approx.), delete "tritration" and insert --titration--, therefor In column 52, line 50 (Approx.), delete "NMR" and insert --$^1$H NMR--, therefor In column 53, line 35, after "F.", insert --,--, therefor In column 53, line 36, delete "U.S.A." and insert --, U.S.A.,--, therefor In column 53, line 46, delete "U.S.A." and insert --, U.S.A.,--, therefor In the Claims In column 56, line 18, in Claim 1, after "attached", insert --to--, therefor In column 58, line 31, in Claim 13, delete "an" and insert --a--, therefor In column 58, line 36, in Claim 14, after "and", insert --a--, therefor In column 59, line 12-13 (Approx.), in Claim 17, delete "N(R$^C$)" and insert --N(R$^c$)--, therefor In column 60, line 1, in Claim 17, delete "$C_{1-4}$" and insert --$C_{1-4}$alkyl--, therefor In column 60, line 5, in Claim 17, after "attached", insert --to--, therefor In column 60, line 7, in Claim 17, after "-S-", insert -- -S(O)- --, therefor In column 60, line 9, in Claim 17, after "-S-,", delete "$S(O)_2$" and insert --S(O)--, therefor

UNITED STATES PATENT AND TRADEMARK OFFICE
CERTIFICATE OF CORRECTION

PATENT NO. : 8,372,823 B2  Page 1 of 1
APPLICATION NO. : 12/600728
DATED : February 12, 2013
INVENTOR(S) : Dale L. Boger It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 425 days.

Signed and Sealed this
First Day of September, 2015

Michelle K. Lee
*Director of the United States Patent and Trademark Office*